(12) United States Patent
Bouchard et al.

(10) Patent No.: US 6,416,293 B1
(45) Date of Patent: Jul. 9, 2002

(54) PUMPING CARTRIDGE INCLUDING A BYPASS VALVE AND METHOD FOR DIRECTING FLOW IN A PUMPING CARTRIDGE

(75) Inventors: Clement D. Bouchard, Pembroke; Robert J. Bryant, Manchester; Lawrence B. Gray, Merrimack; Geoff P. Spencer, Manchester, all of NH (US)

(73) Assignee: Deka Products Limited Partnership, Manchester, NH (US)

( * ) Notice: Subject to any disclaimer, the term of this patent is extended or adjusted under 35 U.S.C. 154(b) by 0 days.

(21) Appl. No.: 09/357,610

(22) Filed: Jul. 20, 1999

(51) Int. Cl.$^7$ .................. F04B 53/00; A61M 37/00; F16L 58/00
(52) U.S. Cl. .................. 417/53; 417/313; 417/395; 137/599.14; 604/153; 604/131
(58) Field of Search .................. 417/53, 538, 392, 417/395, 313; 604/153, 151, 131, 246, 30, 403, 406, 407; 92/79, 78 R, 96; 137/599.14

(56) References Cited

U.S. PATENT DOCUMENTS

| | | | |
|---|---|---|---|
| 4,479,760 A | * | 10/1984 | Bilstad et al. ............... 417/395 |
| 4,479,761 A | * | 10/1984 | Bilstad et al. ............... 417/395 |
| 4,479,762 A | | 10/1984 | Bilstad et al. ............... 417/395 |
| 4,486,190 A | * | 12/1984 | Reinicke ....................... 604/67 |
| 4,634,430 A | * | 1/1987 | Polaschegg ................. 604/141 |
| 4,778,451 A | | 10/1988 | Kamen .......................... 604/67 |
| 4,808,161 A | * | 2/1989 | Kamen .......................... 604/67 |
| 4,826,482 A | | 5/1989 | Kamen .......................... 604/67 |
| 4,828,543 A | | 5/1989 | Weiss et al. |
| 4,833,922 A | * | 5/1989 | Frick et al. .................... 73/756 |
| 4,976,162 A | * | 12/1990 | Kamen ......................... 73/865.9 |
| 5,088,515 A | * | 2/1992 | Kamen .......................... 137/15 |
| 5,178,182 A | * | 1/1993 | Kamen ....................... 137/454.2 |
| D350,823 S | | 9/1994 | Lanigan ....................... D24/111 |
| 5,350,357 A | | 9/1994 | Kamen et al. ................ 604/29 |
| 5,351,686 A | | 10/1994 | Steuer et al. |
| 5,411,472 A | | 5/1995 | Steg, Jr. et al. |
| 5,421,823 A | | 6/1995 | Kamen et al. ................ 604/28 |
| 5,423,738 A | | 6/1995 | Robinson et al. ............ 604/4 |
| 5,429,485 A | | 7/1995 | Dodge |
| 5,431,626 A | | 7/1995 | Bryant et al. ................. 604/65 |
| 5,438,510 A | | 8/1995 | Bryant et al. ........... 364/413.11 |
| 5,474,683 A | | 12/1995 | Bryant et al. ................ 210/646 |
| 5,558,255 A | | 9/1996 | Sancoff et al. |
| 5,575,310 A | | 11/1996 | Kamen et al. ........... 137/614.11 |
| 5,578,012 A | | 11/1996 | Kamen et al. ............... 604/151 |
| 5,628,908 A | | 5/1997 | Kamen et al. ............... 210/646 |
| 5,634,896 A | | 6/1997 | Bryant et al. ................. 604/29 |
| 5,938,634 A | | 8/1999 | Packard ........................ 604/29 |
| 5,989,423 A | * | 11/1999 | Kamen et al. ............... 210/258 |
| 6,041,801 A | | 3/2000 | Gray et al. |
| 6,065,941 A | | 5/2000 | Gray et al. |
| 6,223,130 B1 | * | 4/2001 | Gray et al. .................. 700/282 |
| 6,302,653 B1 | | 10/2001 | Bryant et al. |

OTHER PUBLICATIONS

Therakos, Inc., The Uvar® XTS™ System sales brochure, printed and handed out to custtomers and potential customers in Europe more than one year before the filing date of the instant application.
U.S. application No. 09/108,528, Gray et al.
U.S. application No. 09/193,337, Gray et al.

* cited by examiner

Primary Examiner—Charles G. Freay
(74) Attorney, Agent, or Firm—Wolf, Greenfield & Sacks, P.C.

(57) ABSTRACT

Pumping cartridges are disclosed for use in pumping systems. One such cartridge includes a series of fluid flow paths therein and a bypass valve therein, the bypass valve can selectively block fluid flow along one or both of two fluid flow paths through the valve. In some embodiments, the pumping cartridges are removable from a reusable pump drive component. In some embodiments the pumping cartridges comprise a substantially rigid component having one or more channels and/or depressions therein covered by a membrane so that together the rigid component and the membrane define a series of fluid flow paths, pump chambers and fluidic valves, including a bypass valve.

33 Claims, 23 Drawing Sheets

PUMPING CARTRIDGE INCLUDING A BYPASS VALVE AND METHOD FOR DIRECTING FLOW IN A PUMPING CARTRIDGE

FIELD OF THE INVENTION

The present invention relates generally to systems and methods for metering and pumping fluids. In particular, in some embodiments, the invention relates to pumping systems utilizing removable pumping cartridges, and, more specifically to cartridges having valves and fluid flow paths therein. The pumping cartridges in some embodiments are especially useful for medical infusion and fluid-handling.

BACKGROUND OF THE INVENTION

A wide variety of applications in industrial and medical fields require fluid metering and pumping systems able to deliver precisely measured quantities of fluids at accurate flow rates to various destinations. In the medical field especially, precise and accurate fluid delivery is critical for many medical treatment protocols. Medical infusion and fluid-handling systems for use in the pumping or metering fluids to and/or from the body of a patient typically require a high degree of precision and accuracy in measuring and controlling fluid flow rates and volumes. For example, when pumping medicaments or other agents to the body of a patient, an infusion flow rate which is too low may prove ineffectual, while an infusion flow rate which is too high may prove detrimental or toxic to the patient.

Pumping and fluid metering systems for use in medical applications, for example in pumping fluids to and/or from the body of a patient, are known in the art. Many of such prior art systems comprise peristaltic or similar type pumping systems. Such prior art systems typically deliver fluid by compressing and/or collapsing a flexible tube or other flexible component containing the fluid to be pumped. While such known systems are sometimes adequate for certain applications, precise and accurate flow rates in such systems can be difficult to measure and control due to factors such as distortion of the walls of collapsible tubing or components of the systems, changes in relative heights of the patient and fluid supply, changes in fluid supply line or delivery line resistance, and other factors.

Another shortcoming of such prior art systems is that it is often difficult to determine and maintain accurate volumetric flow rates in real time during operation of the infusion system. Typically, many such prior art systems utilize volume and flow rate measurement techniques that, and difficult to implement and cannot be performed in real time as the system is operating. Some approaches which have been used in such prior art systems for measuring volumes and flow rates include optical drop counting, the weighing of chambers containing infusion liquids, and other approaches.

Many such prior art infusion systems also employ valving systems which comprise clamps, or other pinching devices, which open and close a line by pinching or collapsing the walls of tubing. Such valving arrangements can have several shortcomings for applications involving medical infusion including difficulties in obtaining a fluid-tight seal and distortion of the walls of the tubing, which can lead to undesirable fluid leakage and/or irregular flow rates.

In addition, many typical prior art infusion systems, such as those described above, are constrained to fairly simple fluid handling tasks, such as providing a single or, in some cases, several individual flow paths between one or more fluid sources and a patient. Such prior art systems are not well suited for performing complex, multi-functional fluid handling and pumping tasks and often do not have sufficient operating flexibility to be used for a wide variety of fluid handling applications, without significant rearranging or retooling of the components of the system.

Also, for medical infusion applications involving the pumping or metering of fluids to the body of a patient, it is important to detect air present in a line pumping fluid to the body of a patient and to prevent such air from entering the body of the patient. Typically, prior art infusion systems employed for such applications detect the presence of air in the system by relying only on external air detection components, for example ultrasonic detectors, which are typically downstream of a pump and immediately upstream of the patient. Also, for such systems, once air has been detected in the line, purging the air from the line before it reaches the patient may require manual intervention and, in some cases, disconnection of lines within the system.

For pumping and infusion systems utilized for pumping fluids to the body of a patient, it is also typically desirable to pass fluids through a filter or screen prior to their entering the body of the patient in order to remove any insoluble clumps, or aggregates of material therefrom that may be detrimental to the patient if infused into the body. Such filters are especially important when pumping blood or blood components to the body of a patient; in which case, the filters serve primarily as blood clot filters to remove clots or aggregated cells from the blood or blood components. Prior art infusion systems used for such applications can include blood clot/particulate filters outside the pumping component of the system, installed on the line providing infused fluid to the patient. Such assembly requires additional setup time and attention from an operator of the system and often results in another potential location of fluid leakage or site of contamination within the system.

While the above mentioned and other prior art pumping and fluid handling systems represent, in some instances, useful tools in the art of fluid handling and pumping there remains a need in the art to: (a) provide pumping and fluid metering systems which have an improved ability to control and measure volumes and flow rates; (b) provide improved valving systems; (c) provide increased flexibility for multiple uses; and (d) include air detection capability and integrated fluid filtration. Certain embodiments of the present invention address one or more of the above needs.

SUMMARY OF THE INVENTION

Certain embodiments of the present invention provide a series of pumping systems, methods for operating the systems, and components of the systems. These embodiments include, in one aspect, a series of systems for measuring the volume of a volumetric chamber, detecting the presence of a gas in a pump chamber, and/or pumping a liquid with a pump chamber. Some embodiments of the present invention include a series of methods for pumping a liquid at a desired average flow rate with a pumping cartridge of a pumping system. Some embodiments of the present invention provide a series of pumping cartridges and pump chambers, and methods for operating such cartridges and chambers.

According to one embodiment of the present invention, a method and corresponding system for detecting the presence of a gas in a pump chamber is disclosed. The pump chamber may be an isolatable pump chamber. According to this embodiment, the method includes the steps of: isolating the pump chamber; determining a first measured parameter related to the volume of the pump chamber with at least a first force supplied to a surface of the pump chamber; determining a second measured parameter related to the volume of the pump chamber with at least a second force applied to the surface of the pump chamber; and then comparing the first measured parameter and the second measured parameter.

In another embodiment, a method for detecting the presence of a gas in a pump chamber is disclosed, where the pump chamber is coupled to or contained within a control chamber. In this embodiment, the method comprises: supplying a measurement gas to the control chamber at a first measured pressure; changing the pressure of the measurement gas in the control chamber to a second measured pressure; supplying a measurement gas to the control chamber at a third measured pressure; changing the pressure of the measurement gas in the control chamber to a fourth measured pressure; and determining the presence of a gas in the pump chamber based at least in part on the measured pressures.

In yet another embodiment, a method for detecting the presence of gas in a pump chamber is disclosed, where the pump chamber is coupled to or contained within a control chamber. The method comprises determining a first measured parameter related to the volume of the pump chamber and/or the control chamber with a fluid supplied to the control chamber at a first pressure, determining a second measured parameter related to the volume of the pump chamber and/or the control chamber with a fluid supplied to the control chamber at a second pressure, and comparing the first measured parameter and the second measured parameter.

In yet another embodiment, a method for detecting the presence of gas in a pump chamber is disclosed, where the pump chamber is at least partially comprised of a movable surface. The method comprises determining a first measured parameter related to a volume of the pump chamber with at least a first force applied to the movable surface, where the first force creates a first level of stress in the movable surface. The method further comprises determining a second measured parameter related to the volume of the pump chamber with at least a second force applied to the movable surface, where the second force creates a second level of stress in the movable surface. The method further comprises comparing the first measured parameter and the second measured parameter.

In another embodiment, a method for detecting the presence of a gas in a pump chamber is disclosed, where the pump chamber is at least partially comprised of a movable surface and is coupled to or contained within a control chamber. The method comprises: supplying a measurement gas to the control chamber at a first measured pressure, where the first measured pressure creates a first difference in pressure between the pump chamber and the control chamber; supplying a measurement gas to the control chamber at a second measured pressure, where the second measured pressure creates a second difference in pressure between the pump chamber and the control chamber; and determining the presence of a gas in the pump chamber based at least in part on the measured pressures.

In another embodiment, a system for detecting the presence of a gas in an isolatable pump chamber is disclosed. In this embodiment, the system includes a force applicator that is constructed and arranged to apply a force to a surface of the pump chamber at at least a first level of force and a second level of force. The system further includes a comparer configured to determined the presence of a gas in the pump chamber based at least in part on a first measured parameter related to the volume of the pump chamber at a first condition, and a second measured parameter related to the volume of the pump chamber at a second condition.

In another embodiment, a system for detecting the presence of a gas in a pump chamber is disclosed. The system in this embodiment includes a control chamber that is coupled to or contains the pump chamber, a flexible membrane comprising at least a portion of the pump chamber, and at least one pressure measuring component able to measure a pressure in the control chamber. The system further includes a fluid supply system in fluid communication with the control chamber that is able to supply a fluid to the control chamber at at least a first and a second predetermined pressure, where the fluid pressure in the control chamber is measured with the pressure measuring component. The system in this embodiment also includes a comparer configured to determine the presence of a gas in the pump chamber based on a first measured parameter related to a volume of the control chamber at at least the first pressure and a second measured parameter related to the volume of a control chamber at at least the second pressure.

In yet another embodiment, a system for detecting the presence of a gas in a pump chamber is disclosed. The system in this embodiment includes a control chamber that is coupled to or contains the pump chamber, a pressure supply to pressurize the control chamber at at least a first pressure and a second pressure, and a comparer that is configured to determine the presence of gas in the pump chamber based at least in part on a first measured parameter related to a volume of the pump chamber and/or control chamber at a first condition, and a second measured parameter related to a volume of a pump chamber and/or control chamber at a second condition.

In another embodiment, a system for detecting the presence of a gas in a pump chamber is disclosed. The system in this embodiment comprises force applicator means for supplying a force to the surface of the pump chamber at a first level of force and a second level of force, and processor means for determining the presence of a gas in the pump chamber based at least in part on a first measured parameter related to the volume of the pump chamber at a first condition and a second measured parameter related to the volume of the pump chamber at a second condition.

In another embodiment, a pump chamber is disclosed. The pump chamber in this embodiment includes a wall and a movable surface comprising at least a portion of the wall. The pump chamber further includes at least one spacer positioned within the pump chamber to inhibit gas from being pumped through the pump chamber.

In yet another embodiment, a pump chamber including a wall and a flexible membrane disposed over at least a portion of the wall is disclosed. The pump chamber in this embodiment further includes at least one spacer positioned within the pump chamber to assist air to rise in the pump chamber.

In yet another embodiment, a pump chamber comprising a volumetric container is disclosed. The pump chamber in this embodiment includes a flexible membrane comprising at least a portion of a wall of the container, with at least one spacer positioned within the container to inhibit contact between internal surfaces of the container.

In another embodiment, a pump chamber is disclosed. The pump chamber is this embodiment comprises a first movable wall of the pump chamber, a second wall of the pump chamber, and at least one elongate spacer attached to the second wall and projecting towards the first movable wall.

In another embodiment, a method of pumping of fluid is disclosed. The method involves providing a pump chamber, which includes a flexible membrane, and preventing any gas contained within the pump chamber from being pumped from the pump chamber by providing at least one spacer element within the pump chamber. The spacer element in this embodiment prevents the flexible membrane from contacting an internal surface of the pump chamber during pumping.

In another aspect, a series of pumping systems is disclosed. In one embodiment, the system is for pumping a liquid with a pump chamber. The system in this embodiment includes at least one fluid source, containing a fluid at a first pressure, where the source is able to be placed in fluid communication with a control chamber that is coupled to the pump chamber when the system is in operation. The system in this embodiment further includes a variable sized orifice valve able to be placed in fluid communication with the fluid source and the control chamber. The system may also include a processor which controls the variable sized orifice valve to selectively allow the control chamber to be pressurized with a fluid from the fluid source to a desired pressure. In this embodiment, the processor also controls the pressure within the control chamber during filling of the pump chamber with a liquid or during discharge of a liquid from the pump chamber by selectively changing the size of an orifice within the variable sized orifice valve.

In another embodiment, a method for pumping a liquid using a pump chamber is disclosed. The method comprises: providing a first fluid source that supplies a fluid at a first pressure in fluid communication with an inlet of a variable sized orifice valve; providing a control chamber that is coupled to the pump chamber, where the control chamber is in fluid communication with an outlet of the variable sized orifice valve; selectively changing a size of an orifice within the variable sized orifice valve in order to pressurize the control chamber with the fluid to a desired pressure; and maintaining the desired pressure in the control chamber by selectively changing the size of the orifice.

In another embodiment, a system for measuring the volume of a volumetric chamber is disclosed. The system includes a reference chamber, a first fluid source supplying fluid at a first pressure, and a second fluid source supplying fluid at a second pressure. The system in this embodiment also includes a switch valve having a first and second inlet and an outlet. The first inlet of the switch valve is connected in fluid communication with the first fluid source, and the second inlet of the switch valve is connected in fluid communication with the second fluid source. The outlet of the switch valve is connected in fluid communication with at least one line able to be placed in fluid communication with the reference chamber and the volumetric chamber. The switch valve has a first position that provides fluid communication between the first fluid source and the reference chamber and volumetric chamber, and has a second position that provides fluid communication between the second fluid source and the reference chamber and volumetric chamber. The system may also include a processor which controls the switch valve to selectively allow the reference chamber and/or the volumetric chamber to be pressurized to a selected pressure with a fluid from either the first fluid source or the second fluid source. The processor also determines a volume of the volumetric chamber based at least in part on the selected pressure.

In another embodiment, a method for measuring a volume of a volumetric chamber is disclosed. The method comprises providing a first fluid source to supply fluid at a first pressure, a second fluid source to supply fluid at a second pressure, and a switch-valve having a first inlet, a second inlet, and an outlet, where the first inlet is connected in fluid communication with the first fluid source, the second inlet is connected in fluid communication with the second fluid source, and the outlet is connected in fluid communication with at least one line that is able to be placed in fluid communication with the volumetric chamber. The method further comprises positioning the switch valve to allow the volumetric chamber to be pressurized with the fluid from the first fluid source, determining a first pressure of the volumetric chamber, and determining a volume of the volumetric chamber based at least in part on the first pressure.

In yet another embodiment, a system for pumping a liquid with a pump chamber is disclosed. The system in this embodiment includes a first fluid source supplying fluid at a first pressure, and a second fluid source supplying fluid at a second pressure. The system in this embodiment also includes a switch valve having a first and a second inlet and an outlet. The first inlet is connected in fluid communication with the first fluid source, and the second inlet is connected in fluid communication with the second fluid source. The outlet of the switch valve is connected in fluid communication with at least one line able to be placed in fluid communication with a control chamber that is coupled to the pump chamber when the system is in operation. The switch valve has a first position that provides fluid communication between the first fluid source and the control chamber, and has a second position that provides fluid communication between the second fluid source and the control chamber.

In another embodiment, a method for pumping a liquid with a pump chamber is disclosed. The method comprises providing a first fluid source to supply fluid at a first pressure, a second fluid source to supply fluid at a second pressure, and a switch-valve having a first inlet, a second inlet, and an outlet, where the first inlet is connected in fluid communication with the first fluid source, the second inlet is connected in fluid communication with the second fluid source, and the outlet is connected in fluid communication with at least one line able to be placed in fluid communication with a control chamber to be coupled to a pump chamber when the system is in operation. The method further comprises positioning the switch-valve to provide fluid communication between the first fluid source and the control chamber so as to at least partially fill the pump chamber with a liquid, and positioning the switch-valve to provide fluid communication between the first fluid source and the control chamber for dispensing the liquid from the pump chamber.

In yet another aspect, a series of methods and systems for pumping a liquid at a desired average flow rate with a pumping cartridge is disclosed. In one embodiment, the method involves pumping a liquid at a desired average flow rate with a pumping cartridge, where the cartridge includes at least one pump chamber, at least a portion of which pump chamber includes a movable surface. The method of this embodiment involves: at least partially filling the pump chamber with a liquid; isolating the pump chamber; applying a force to the movable surface and regulating the flow of liquid from the pump chamber while maintaining the force on the surface.

In another embodiment, a method for pumping a liquid at a desired average flow rate with a pumping cartridge that includes at least one pump chamber, at least a portion of which pump chamber comprises a movable surface is disclosed. The method of this embodiment involves: closing a valve positioned on an outlet line of the pump chamber; at least partially filling the pump chamber with a liquid; closing a valve positioned on the inlet line of the pump chamber thereby isolating the pump chamber; and, while maintaining the inlet valve in a closed position, applying a force to the movable surface and opening the outlet valve for predetermined periods at predetermined intervals while maintaining the force on the movable surface. The predetermined time periods and intervals may be selected to yield a desired average flow rate.

In yet another embodiment, a fluid metering system is disclosed. The system of this embodiment comprises a reusable component that is constructed and arranged for operative association with a removable pumping cartridge by coupling to the pumping cartridge. The pumping cartridge of this embodiment includes at least one pump chamber and has an outlet line having an outlet valve therein. The fluid metering system in this embodiment includes a processor that is configured to control pulsing of the outlet valve to achieve a desired flow rate.

In yet another embodiment, a fluid metering system including a reusable component that is constructed and arranged for operative association with a removable pumping cartridge is disclosed. The pumping cartridge includes at least one pump chamber having an inlet line having a first valve therein and an outlet line having a second valve therein. The pump chamber is at least partially formed from a movable surface. The system further includes valve actuating means for operating the first valve and the second valve, and pump chamber actuating means for applying a force to the movable surface. The system further includes control means for controlling the valve actuating means and pump chamber actuating means to deliver fluid at a desired flow rate from the pump chamber by closing the first valve, applying a force to the movable surface, and pulsing the second valve.

In another embodiment, a series of pumping cartridges is disclosed. In one embodiment, the pumping cartridge includes a first liquid flow path, a second liquid flow path, and a bypass valve in fluid communication with the first liquid flow path and the second liquid flow path. The bypass valve is constructed and arranged to selectively permit liquid flow through the first liquid flow path or the second liquid flow path, or to prevent liquid flow through both the first liquid flow path and the second liquid flow path.

In another embodiment, a pumping cartridge including a first component and at least one membrane disposed on the first component is disclosed. The first component and the membrane define a bypass valving chamber. The bypass valving chamber in this embodiment includes three ports, two of which ports are occludable by the membrane. The pumping cartridge in this embodiment further includes a first fluid flow path entering the bypass valving chamber through a first port and exiting the bypass valving chamber through a third occludable port. The pumping cartridge in this embodiment further includes a second fluid flow path entering the bypass valving chamber through a second occludable port and exiting the bypass valving chamber through the first port.

In yet another embodiment, a reusable system is disclosed that is constructed and arranged for operative association with a removable pumping cartridge, where the pumping cartridge provides at least two fluid flow paths therein and includes a bypass valving chamber in fluid communication with a first fluid flow path and a second fluid flow path. The system in this embodiment includes a pump housing component that is constructed and arranged to couple to the pumping cartridge, and a valve actuator to actuate the bypass valving chamber. The valve actuator in this embodiment is disposed within the pump housing adjacent to and in operative association with the bypass valving chamber, when the pumping cartridge is coupled to the pump housing In yet another embodiment, a reusable system is disclosed that is constructed and arranged for operative association with a removable pumping cartridge, where the pumping cartridge provides at least two liquid flow paths therein and includes a first component, with at least one membrane disposed on the first component. The first component and the membrane define a bypass valving chamber. The reusable system in this embodiment includes a pump housing component that is constructed and arranged for operative association with the pumping cartridge by coupling to the pumping cartridge. The reusable system in this embodiment also includes a valve actuator to actuate the bypass valving chamber, which actuator is disposed adjacent to and in operative association with the bypass valving chamber when the pumping cartridge is coupled to the pump housing. The system may further include a force applicator forming at least a part of the valve actuator, where the force applicator is constructed and arranged to alternatively: apply a force to at least a portion of the membrane to restrict liquid flow through a first liquid flow path through the bypass valving chamber; apply a force to at least a portion of the membrane to restrict liquid flow through a second liquid flow path through the bypass valving chamber; and apply a force to at least a portion of the membrane to restrict liquid flow through both the first and the second liquid flow paths.

In another embodiment, a method for directing flow in a pumping cartridge is disclosed, where the pumping cartridge includes a bypass valving chamber having three ports therein and two liquid flow paths therethrough. At least a portion of the bypass valving chamber in this embodiment is formed from a membrane. The method in this embodiment comprises occluding a first port disposed in the bypass valving chamber with the membrane to restrict the flow of liquid through the bypass valving chamber along a first flow path, or occluding a second port disposed in the bypass valving chamber with the membrane to restrict the flow of liquid through the bypass valving chamber along a second flow path, and/or occluding both the first and second ports disposed in the bypass valving chamber with the membrane to restrict the flow of liquid along both the first and second flow paths.

In yet another aspect, pumping cartridges including filter elements and methods for filtering fluids are disclosed. In one embodiment, a removable pumping cartridge that is constructed and arranged for operative association with the reusable component is provided, the cartridge including at least one pump chamber, at least one valving chamber, and at least one fluid flow path constructed and positioned within the cartridge to provide fluid communication between the pump chamber and a body of a patient when pumping a fluid thereto. The cartridge in this embodiment further includes at least one filter element in fluid communication with the fluid flow path.

In another embodiment, a method for filtering a liquid supplied to the vasculature of a patient is disclosed. The method in this embodiment includes supplying a liquid to a pump chamber disposed in a removable pumping cartridge, where the pumping cartridge is constructed and arranged for operative association with a reusable component. The method further involves pumping the liquid to the patient through a filter element disposed in the pumping cartridge.

In yet another aspect, occluders for occluding collapsible tubing, and methods for occluding collapsible tubing using such occluders are disclosed. In one embodiment, an occluder for occluding at least one collapsible tube is disclosed. The occluder in this embodiment comprises an occluding member and a force actuator that is constructed and positioned to bend the occluding member.

In another embodiment, a method for occluding at least one collapsible tube is disclosed. The method comprises applying a force to bend the occluding member in order to open the collapsible tube to enable fluid to flow therethrough, and releasing the force in order to relax the occluding member and occlude the collapsible tube.

Each of the above disclosed inventions and embodiments may be useful and applied separately and independently, or may be applied in combination. Description of one aspect of the inventions are not intended to be limiting with respect to other aspects of the inventions.

Other advantages, novel features, and objects of the invention will become apparent from the following detailed description of the invention when considered in conjunction with the accompanying drawings, which are schematic and are not intended to be drawn to scale. In the figures, identical or substantially similar components that are illustrated in various figures may be represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 11b is a cross-sectional illustration of the pumping cartridge of FIG. 11a;

FIG. 11c is a partially-cutaway cross-sectional illustration of a valve provided by the pumping cartridge of FIG. 11a;

FIG. 11e is a partially-cutaway cross-sectional illustration of a bypass valving chamber of the pumping cartridge of FIG. 11a;

DETAILED DESCRIPTION

Figure 1:
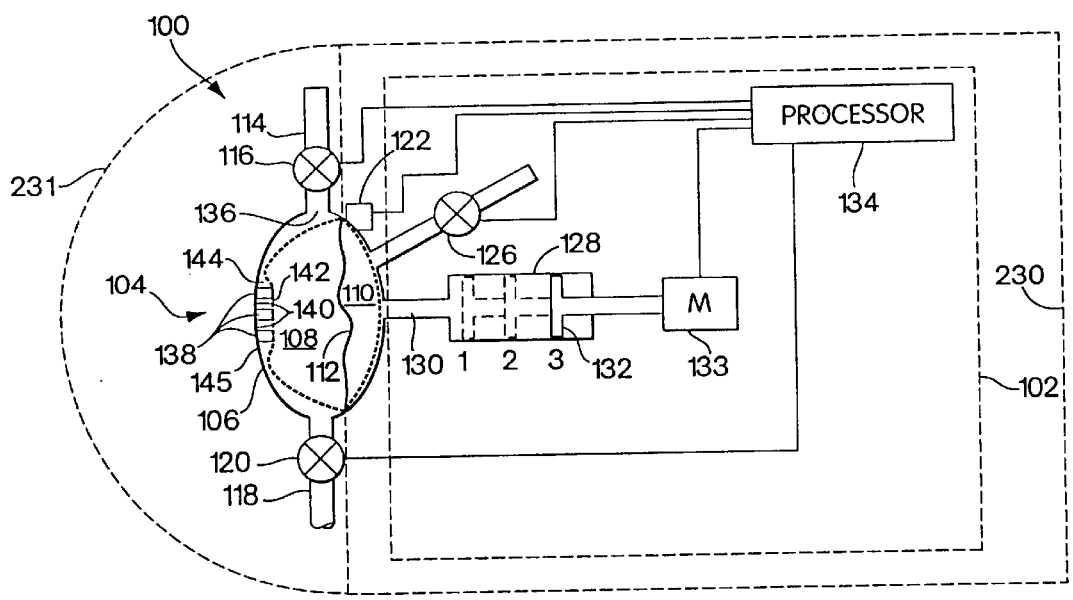
FIG. 1 is a schematic illustration of a pumping system according to one embodiment of the invention.

Certain embodiments of the present invention relate to a series of methods and systems useful in fluid pumping applications. Some embodiments of these methods and systems are especially useful for applications involving the pumping of liquids to and from the body of a patient during a medical treatment or procedure. The need for pumping liquids to and from the body of a patient arises in a wide variety of medical treatments and procedures including, for example, hemodialysis for the treatment of kidney failure, plasmapheresis for separating blood cells from plasma, general infusion of intervenous fluids and/or medicaments, and a wide variety of additional treatments and procedures apparent to those of ordinary skill in the art. The methods and systems of the current invention may be advantageously utilized for any of the above-mentioned liquid pumping applications, or any other fluid pumping application, including various industrial applications, as apparent to those of ordinary skill in the art.

Certain embodiments of the present invention relate to pumping systems and methods for operating the pumping systems for pumping liquids with a pump chamber. The term "pump" or "pumping" as used herein refers to the forcing, controlling or metering of the flow of a fluid through a line either by metering a flow of a fluid that is moving under the influence of a pre-existing pressure drop within the line, or by forcing a fluid through a line by increasing the pressure of the fluid within the line. Many embodiments, as described in more detail below, involve systems where the pressure of the fluid being pumped is increased (e.g., increased cyclically) by using a pump chamber and a source of mechanical force acting on one or more external surfaces of the pump chamber.

A "chamber" as used herein, for example in the context of a pump chamber, refers to a volumetric container having a constant or variable internal volume, which is able to contain a fluid. A "fluid" as used herein can refer to a material that is either a liquid or gas.

The methods and systems provided in some embodiments of the present invention, in preferred embodiments, include pumping systems with pump chambers having at least one moveable surface. A "moveable surface" as used herein in this context refers to a surface of a chamber that can be displaced by a force applied thereto, so as to change an internal volume of the chamber. A non-limiting list of pumping systems that employ pump chambers including at least one moveable surface include: diaphragm pumps, piston pumps, peristaltic pumps, flexible bulb pumps, collapsible bag pumps, and a wide variety of other pump configurations, as apparent to those of ordinary skill in the art.

Preferred embodiments of the invention involve pumping systems including a pump chamber which comprises an isolatable chamber. An "isolatable chamber" as used herein refers to a volumetric chamber or container for holding a fluid, which can isolate the fluid from fluid communication with fluids outside of the isolatable chamber (e.g., by sealing or closing inlets and outlets to the chamber). The term "fluid communication" as used herein refers to two chambers, or other components or regions containing a fluid, where the chambers, components, or regions are connected together (e.g., by a line, pipe, or tubing) so that a fluid can flow between the two chambers, components, or regions. Therefore, two chambers which are in "fluid communication" can, for example, be connected together by a line between the two chambers, such that a fluid can flow freely between the two chambers. For embodiments involving an isolatable chamber, for example an isolatable pump chamber, lines connecting the isolatable chamber to other chambers or regions of the pumping system may include at least one valve (or other device) therein which may be closed, or occluded, in order to block fluid communication between the chambers.

The term "valve" as used herein refers to a component of a pumping system disposed in, or adjacent to, a fluid line or fluid flow path within the system, which component is able to block the flow of a fluid therethrough. Valves, which may be utilized in various aspects of the invention, include, but are not limited to, ball valves, gate valves, needle valves, globe valves, solenoid-activated valves, mechanisms or components for applying an external force to a fluid flow path so as to block or occlude the flow path (for example, by pinching or collapsing a length of flexible tubing), and others, as would be apparent to those of ordinary skill in the art. Two or more chambers or regions of a pumping system which are connected together by a fluid flow path including one or more valves therein are able to be placed in fluid communication. "Able to be placed in fluid communication" as used herein refers to components, regions, or chambers within a pumping system, which components, regions, or chambers are either connected in unrestricted fluid communication or have at least one valve therebetween that can be selectively opened to place the components, regions, or chambers in fluid communication. Components, regions, or chambers connected together by a fluid flow path that includes no valves or obstructions therein are said to be in "unrestricted fluid communication" as used herein. The term "fluid communication" generally includes both unrestricted fluid communication and able to be placed in fluid communication.

In many pumping applications, e.g., pumping liquids to the body of a patient, it is critical to prevent gases, such as air, which may find their way into a pump chamber of the system from being pumped out (e.g., pumped into the body of the patient). Certain embodiments of the present invention include methods and systems for detecting the presence of a gas in an isolatable pump chamber. Such methods and systems may utilize pump chambers having at least one moveable surface, where, in some embodiments the moveable surface is a flexible membrane, which, in some such embodiments is elastic. The term "membrane" as used herein refers to a movable surface which comprises at least a portion of a wall of a pump chamber. The term "flexible membrane" as used herein refers to a moveable surface having at least a portion that is movable by bending and/or stretching when a force is applied thereto. A flexible membrane which is "elastic" or an "elastic membrane" as used herein refers to a flexible membrane that provides a resistance to bending and/or stretching by an applied force, which resistance is proportional to an amount of the displacement/stretching of the membrane from an equilibrium configuration without such force applied. A force applied to an elastic membrane that displaces the membrane from a relaxed equilibrium condition will tend to create a stress in the membrane which resists further displacement and creates a restoring force tending to return the membrane to its relaxed equilibrium condition. An "equilibrium condition" as used herein for elastic membranes or other movable surfaces refers to the configuration of the membrane/surface at a condition where there are no applied forces tending to move or displace the membrane/surface from a stationary position. A "relaxed equilibrium condition" as used herein refers to an equilibrium condition wherein a stress within a membrane/surface is at a minimum level allowed by the configuration of the pump chamber. For example, for a pump chamber including an elastic membrane as a portion thereof, a relaxed equilibrium condition could be the configuration of the membrane at its minimum level of strain (stretching) when forces on both sides of the membrane are essentially balanced and equal.

In one embodiment, a method for detecting the presence of a gas in an isolatable pump chamber having at least one moveable surface is used. The method involves isolating the pump chamber, which is at least partially filled with a liquid being pumped, for example by closing an inlet and an outlet valve in fluid communication with the pump chamber. The method of this embodiment further involves determining a measured parameter related to the volume of the pump chamber with a predetermined level of force is applied to a moveable surface of the pump chamber. The method further involves determining the measured parameter related to the volume of the pump chamber again, except this time with a different level of force applied to the moveable surface of the pump chamber. The method involves comparing the measured parameters determined at each condition of the pump chamber described, and detecting the presence of a gas within the pump chamber based on the values of the measured parameters.

This embodiment utilizes, at least in part, the compressibility of any gas within the pump chamber, as contrasted with the essentially incompressible nature of the liquid within the pump chamber, as a means for determining the presence of a gas. The presence of such gas in the pump chamber permits the movable surface to be able to undergo a displacement in response to an applied force thereto owing to the compressibility of the gas in the pump chamber. In some embodiments, the method can involve the determination of a measured parameter related to the volume of the pump chamber determined with at least two substantially differing levels of force applied to a moveable surface of the pump chamber. For example, a first determination of the measured parameter related to the volume of the pump chamber at a first condition can be made with a positive force applied to the moveable surface of the pump chamber, such force tending to decrease the volume of the pump chamber, and a second determination at a second condition can be made with a negative (or lesser) force to the moveable surface of the pump chamber, which force tending to increase the volume of the pump chamber. If the pump chamber is essentially completely filled with a liquid, because the liquid will be essentially incompressible, the measured parameter related to the volume of the pump chamber measured with the pump chamber at a first condition (e.g., with the positive force applied to the moveable surface of the pump chamber) will be nearly identical to the value of the measured parameter related to the volume of the pump chamber measured with the pump chamber at the second condition (e.g., with a negative force applied to the moveable surface of the pump chamber). In contrast, if the pump chamber also contains a quantity of a gas, such as air, because the air is compressible, the measured parameter related to the volume of the pump chamber measured at the first condition can differ from the value of the measured parameter measured with the pump chamber at the second condition by an amount proportional to the quantity of gas within the pump chamber. In short, when a gas is present within the pump chamber, the volume of the pump chamber measured utilizing a positive force applied to a moveable surface thereof can be measurably different than the volume of the pump chamber determined utilizing a negative force applied to a moveable surface thereof. By comparing the measured parameters related to the volume of the pump chamber determined at the first and second conditions above, it can be determined whether there is any gas present within the pump chamber and in some embodiments, roughly, the relative amount of such gas.

A "measured parameter related to a volume" as used herein refers either to a measure of the volume itself or to a measured parameter determined by the system that can be converted to the volume by arithmetic or mathematical transformations utilizing one or more additional parameters that are either constant conversion factors or variables which are not functions of the volume (e.g., unit conversion factors, calibration constants, curve-fit parameters, etc.). In other words, in some embodiments of the invention, the volume of the pump chamber itself need not be determined, but rather parameters from which the volume could be determined, which parameters are typically proportional to the volume, may be determined and compared. Depending on the embodiment, as discussed in more detail below, such measured parameters can include, for example, pressures and combinations of pressures, products of pressures and volumes of components of the pumping system, acoustical signals, temperatures, combinations of temperatures and pressures, values of linear displacement, etc. as apparent to those of ordinary skill in the art. A "condition" as used above in the context of the determination of a measured parameter related to the volume of a chamber, refers herein to a particular state of a pump chamber, or other chamber in which a measured parameter is being determined, which state is associated with at least one measurable parameter related to the volume of the chamber with a particular level of force or range of forces being applied to an external surface of the chamber during the volume measurement procedure.

As would be readily apparent to those of ordinary skill in the art from the disclosure provided herein, the method for determining the presence of a gas in a pump chamber may be utilized and find application in a wide variety of pumping systems known in the art, such pumping systems including a force applicator for applying a variable, or selectable, force and/or range of forces to a moveable surface of the pump chamber. A "force applicator" as used herein in this context refers to a component of a pumping system that is able to apply a force to an external surface of a chamber within the system. Force applicators in pumping systems which may be utilized according to the invention include, but are not limited to: moveable surfaces in contact with the external surface of the pump chamber (e.g. pistons, push rods, plungers, etc.), pressurized fluids in contact with the external surface of the pump chamber, magnetic or electrostatic fields that are able to exert a force on the external surface of the pump chamber, and many others.

Pumping systems utilizing the inventive methods for determining the presence of a gas in a pump chamber also preferably include a mechanism for determining a measured parameter related to the volume of the pump chamber with different levels of force or ranges of forces being applied to a moveable external surface of the pump chamber. For example, a pumping system which includes a moveable surface in contact with the external surface of the pump chamber can include a motor and linear actuator for moving the surface in contact with the pump chamber, so as to create a variable force on the surface of the pump chamber, and can further include a detector for measuring a linear displacement or position of the moveable surface, which linear displacement or position can act as the measured parameter related to the volume of the pump chamber. Similarly, systems which utilize a magnetic or electrostatic field that is able to exert a force on the external surface of the pump chamber can include detectors or measuring devices to determine either field strengths and/or displacements of the external surface of the pump chamber, which measurements can constitute a measured parameter related to the volume of the pump chamber. Other systems, and measurable parameters for determining the volume of the pump chamber for alternative systems may also be used.

One preferred embodiment of a pumping system able to employ the inventive method for detecting the presence of a gas in a pump chamber utilizes pressurized fluids in contact with a moveable, or flexible, surface of the pump chamber in order to apply a force to the surface. Preferred pumping systems according to the invention utilize fluid sources for providing a measuring fluid at different and selectable pressures, which fluid can be brought into contact with a moveable or flexible external surface of a pump chamber. As will be discussed in more detail below, some preferred embodiments of pumping systems utilizing measurement fluids for applying forces to moveable surfaces of pump chambers employ pump chambers having a moveable surface comprised, at least in part, by an elastic flexible membrane. The term "fluid source(s)" as used herein refers to one or more components of a pumping system that alone, or in combination, are able to supply or withdraw a quantity of fluid to another component, or components, of the pumping system with which they are, or are able to be placed, in fluid communication. As discussed below, examples include, but are not limited to, pumps, compressors, pressurized or evacuated tanks, and combinations thereof.

As discussed in more detail below, the fluids supplied by the fluid sources included in certain embodiments of pumping systems useful for practicing the invention provide a measurement gas, most preferably air, but in other embodiments, can also provide one or more liquids. Such fluids, which are provided by the fluid supply components of certain embodiments of the pumping systems according to the invention are hereinafter collectively referred to as "measurement fluids." "Measurement fluids" (e.g., measurement gases or measurements liquids) as used herein refer to fluids which are used to determine a volume, or a measured parameter related to a volume of a volumetric container within the pumping system, for example a pump chamber, or for other purposes within the pumping system, which, preferably, are not in fluid communication with a fluid being pumped or metered by a pump chamber of the system. The measurement fluid sources utilized by certain preferred embodiments of pumping systems according to the invention can comprise one or more components of a measurement fluid supply system that are constructed and arranged to pressurize one or more components of the pumping system. "Constructed and arranged to pressurize" a component, as used herein, refers to a system containing the necessary sources of fluid, together with the associated components (e.g., plumbing and pneumatic or other connections), which are necessary to enable the system to change the pressure of a fluid contained within the component.

One embodiment of a pumping system that utilizes a measurement gas for actuating a pump chamber to pump a liquid therethrough and for detecting the presence of a gas in the pump chamber is shown schematically in FIG. 1. Pumping system 100 includes a fluid supply system 102 containing a fixed quantity of a measurement gas and a mechanism for changing the volume of the measurement gas within the system.

Pumping system 100 includes a pump 104 comprising a substantially rigid container 106 that includes a pump chamber 108 and a control chamber 110 disposed therein. Pump chamber 108 and control chamber 110 are fluidically isolated (i.e., not able to be placed in fluid communication) from each other by a flexible membrane 112, disposed between the two chambers, such that pump chamber 108 is coupled to control chamber 110 and in operative association therewith. Such a membrane may (as just one example) be constructed of medical grade polyvinyl chloride.

"Substantially rigid" as used herein refers to a material, or a component constructed therefrom, that does not flex or move substantially under the application of forces applied by the pumping system. A "control chamber" as used herein refers to a chamber of a pumping system that is coupled to, or contains, a volumetric chamber, for example a pump chamber, for the purpose of exerting a force on the volumetric chamber and, in preferred embodiments, for determining a measured parameter related to the volume of the volumetric container. The term "coupled to" as used in this context with respect to chambers or other components of the pumping system, refers to the chambers or components being attached to, or interconnected with, another component of the pumping system, such that the other component is able to exert a force on an external surface of the chamber or component to which it is coupled.

Liquid to be pumped by pump system 100 enters pump chamber 108 via inlet line 114 including an inlet valve 116 therein. Liquid can be pumped from pump chamber 108 to a desired downstream destination through outlet line 118 including an outlet valve 120 therein.

Control chamber 110 includes a pressure measuring component 122 therein for determining the pressure of the measurement gas within the control chamber. A "pressure measuring component" as used herein refers to a device that is able to convert a fluid pressure into a measurable signal or parameter. Pressure measuring components that may be useful in this embodiment include but are not limited to: transducers; pressure gauges; manometers; piezoresistive elements; and others as apparent to those of ordinary skill in the art.

Preferred embodiments of control chamber 110 of pumping system 100 also include a vent line 124 including a vent valve 126 therein. Control chamber 110 is connected in fluid communication with a variable volume cylinder 128 via a measurement gas inlet line 130. Variable volume cylinder 128 which includes a piston 132 therein which is moved and actuated by motor 133 for compressing, or expanding the volume of the measurement gas contained within the system.

Pumping system 100 also preferably contains a processor 134 which is in electrical communication with the various valves, pressure transducers, motors, etc. of the system and is preferably configured to control such components according to a desired operating sequence or protocol. Reference to a processor being "configured" to perform certain tasks herein refers to such processor containing appropriate circuitry, programming, computer memory, electrical connections, and the like to perform a specified task. The processor may be implemented as a standard microprocessor with appropriate software, custom designed hardware, or any combination thereof. As discussed in more detail below, processor 134, in addition to including control circuitry for operating various components of the system, also preferably includes a comparer that is configured to determine a measured parameter related to the volume of pump chamber 108 and to detect the presence of any gas contained within pump chamber 108 during operation of pump 104. A "comparer" as used herein refers to a processor (e.g., with appropriate programming) or circuit or component thereof that is able to compare the values of two or more measured parameters or other parameters derived therefrom.

In embodiments where passing gas through the system is problematic, pump chamber 108 is oriented in an essentially vertical configuration during operation such that inlet line 114 is disposed above outlet line 118. The above-described orientation is advantageous for preventing any gas which may be present in pump chamber 108 during operation from being pumped from the pump chamber to a downstream destination through outlet line 118. Instead, any gas contained within pump chamber 108 will tend to rise towards the top of the pump chamber, for example the region adjacent to inlet port 136, and will be detected by the system, as described in more detail below, before being pumped from the pump chamber.

In some embodiments, pump chamber 108 includes the novel inclusion of a plurality of spacers 138 included therein. The spacers 138 function to prevent flexible membrane 112 from contacting an inner surface 140 of the pump chamber when the liquid contained within pump chamber 108 is being pumped through outlet line 118. During the pump stroke, the maximum displacement of flexible membrane 112 which is permitted by spacers 138 is shown in FIG. 1 by dashed line 142. It can be seen that even with flexible membrane 112 at its maximum displacement into pump chamber 108, as defined by dashed line 142, spacers 138 create a dead space 144 to contain any gas which may be present in pump chamber 108, thus inhibiting the gas from being pumped through the pump chamber. Spacers 138, in combination with the vertical orientation of pump chamber 108, also serve to assist any gas present in pump chamber 108 to rise to the top of the pump chamber so that it may more easily be purged from the pump chamber, as described in more detail below.

Figure 2:
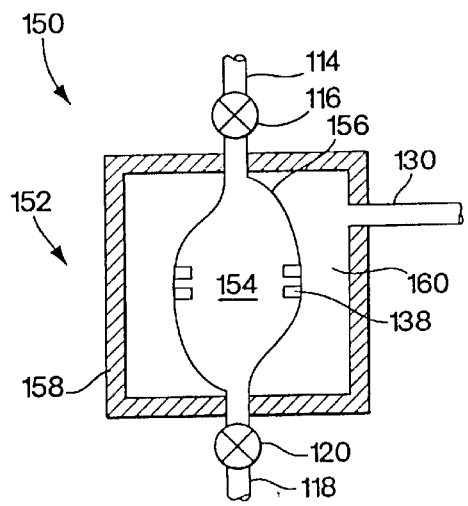
FIG. 2 is a schematic illustration of a fluid pump according to one embodiment of the invention.

Pump chamber 108 of pumping system 100 is essentially defined by a substantially rigid wall 145 (e.g., made of a rigid plastic such as a polyacrylate) having a flexible membrane 112 disposed over the wall, thus forming a volumetric chamber. An alternative embodiment for providing a pump chamber and a control chamber is shown in FIG. 2. Pump 152 of pumping system 150 includes a pump chamber 154 which comprises an essentially flexible container 156 disposed within a substantially rigid enclosure 158 having an interior volume surrounding pump chamber 154 which comprises a control chamber 160. In other embodiments (not shown), the pump chamber may be differently configured or disposed within the control chamber and may include substantially rigid, but moveable surfaces, as opposed to the flexible surfaces of pumping systems 100 and 150 described above.

Figure 3A:
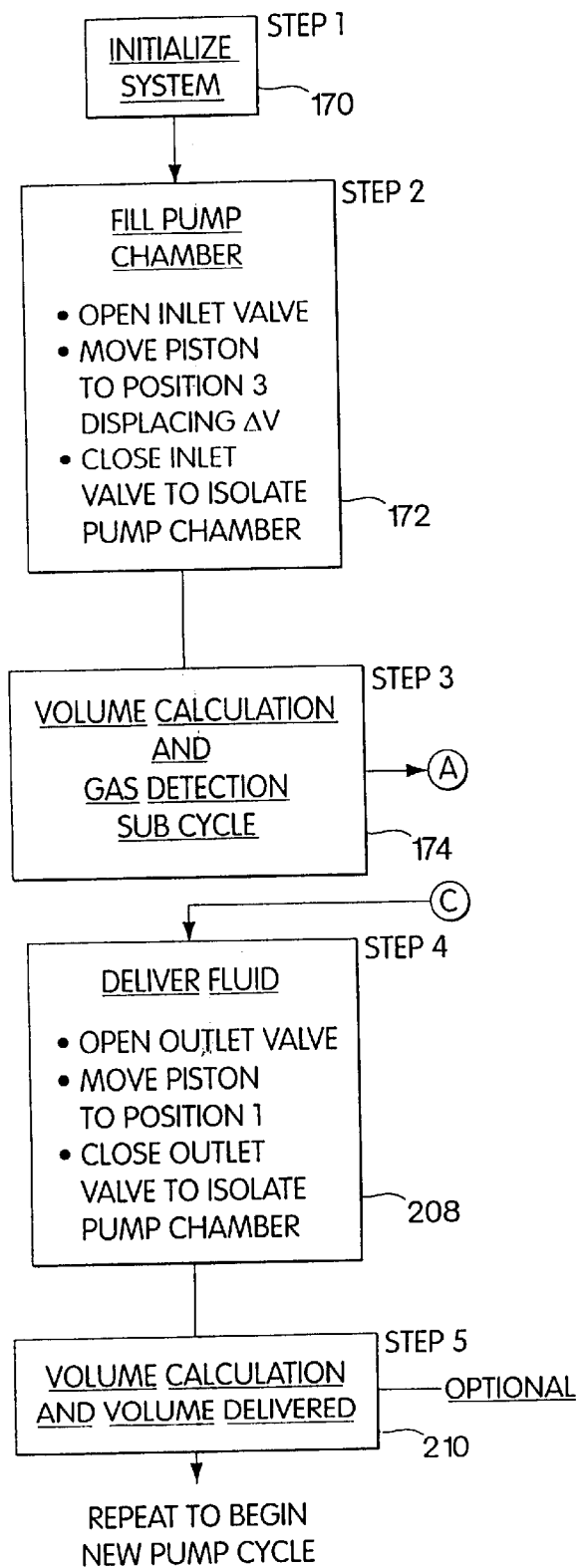
FIG. 3a is a flow chart illustrating a series of steps in a pumping cycle according to one embodiment of the invention.
Figure 3B:
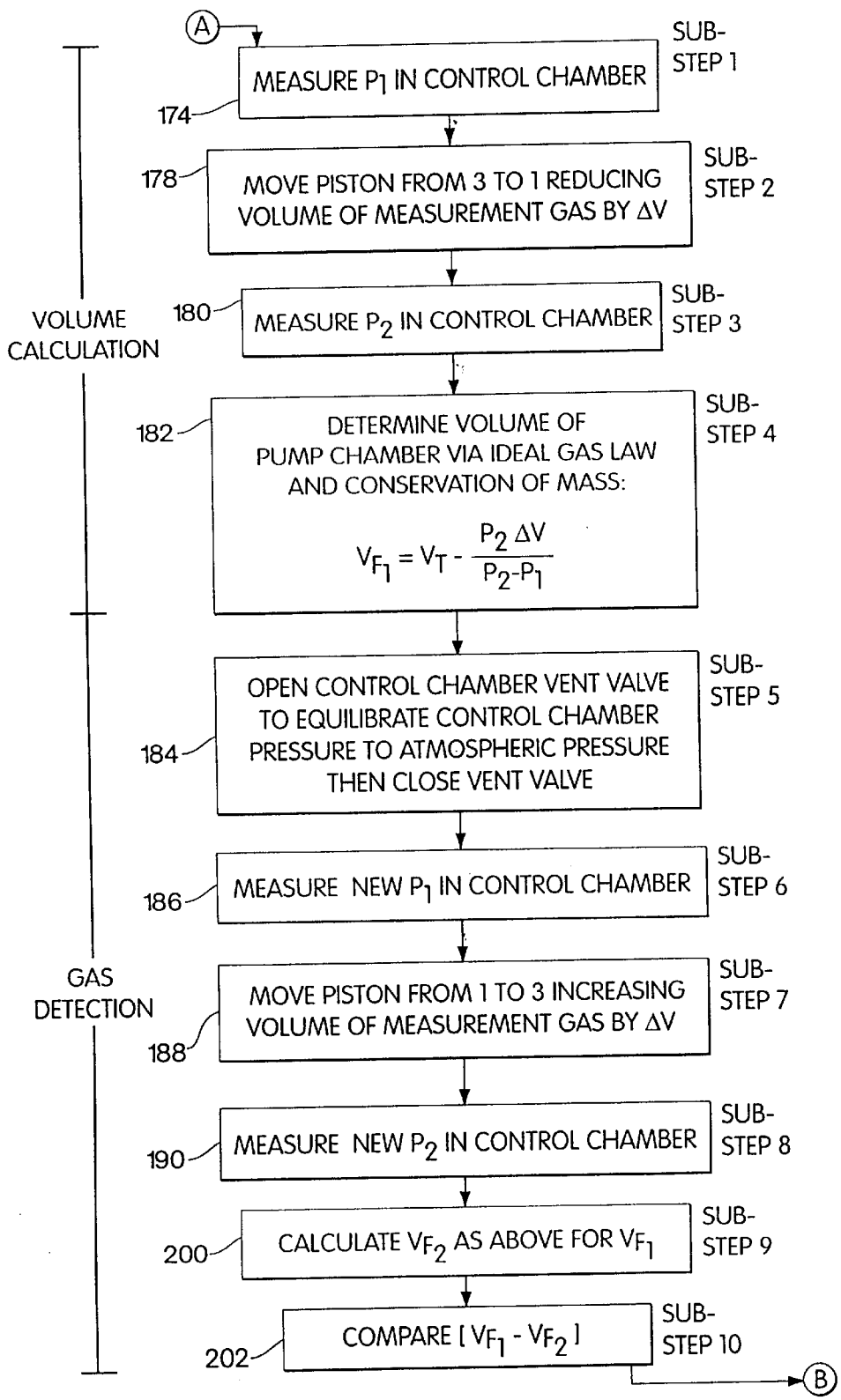
FIG. 3b is a flow chart illustrating a series of substeps of the pumping cycle of FIG. 3a for performing volume calculation and air detection.
Figure 3C:
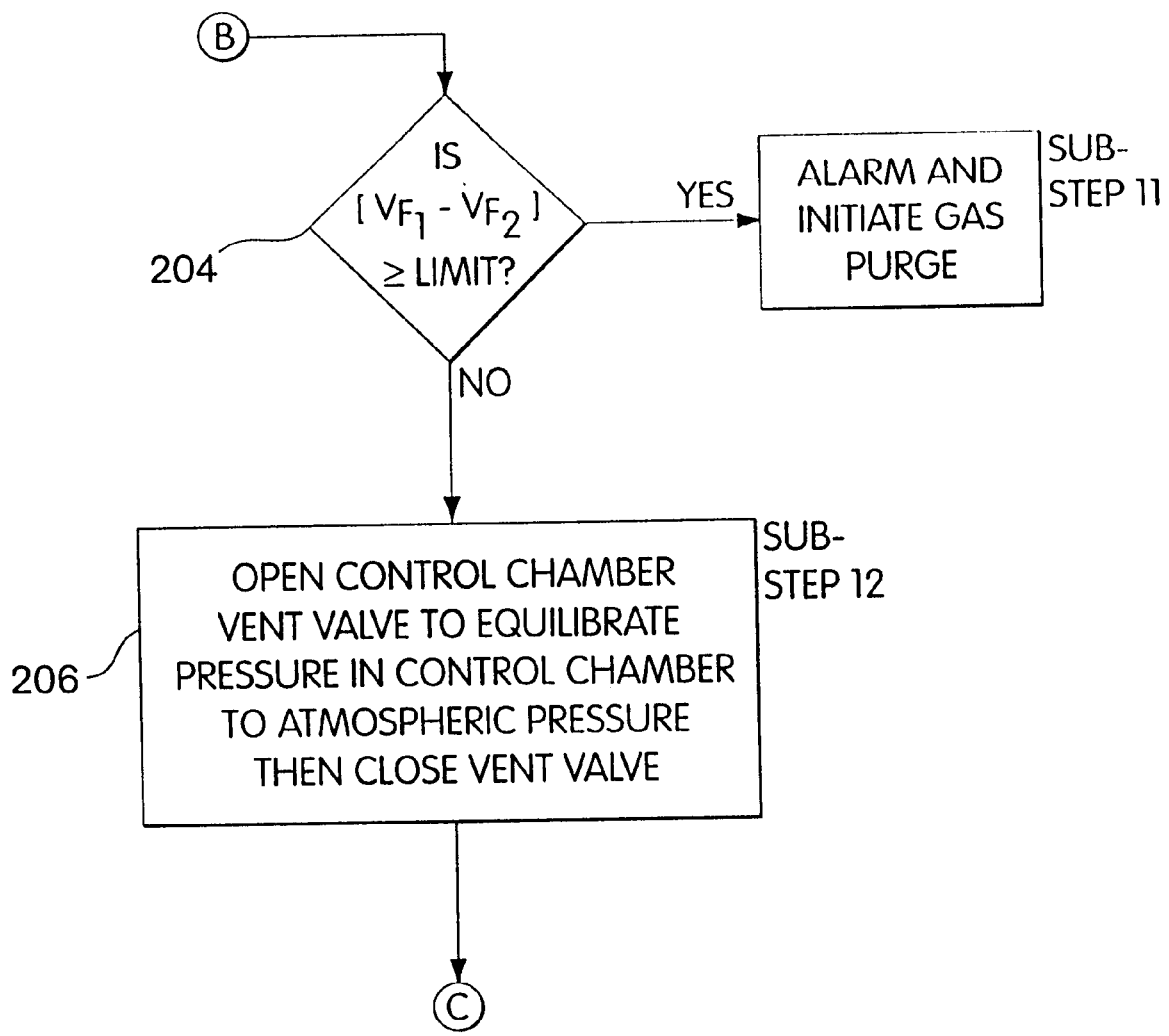
FIG. 3c is a flow chart illustrating a series of substeps of the pumping cycle of FIG. 3a for detecting the presence of a gas in a pump chamber.

One embodiment of a method for operating the pumping system 100 shown in FIG. 1 for pumping a liquid with pump chamber 108, and for detecting the presence of a gas in pump chamber 108, is shown in detail in the flow charts of FIGS. 3a–3c.

Referring to FIG. 3a, an exemplary pump cycle utilizing pumping system 100 will be described. The pump cycle illustrated utilizes changes in displacement of the piston to change the pressure of a measurement fluid within the system in order to apply selected forces to membrane 112 for pumping and air detection. The embodiment illustrated also utilizes an equation of state (e.g. the ideal gas law) in determining pump chamber volumes from measured or known values of pressure and volume.

For embodiments employing a protocol for detecting air/gas where pump and/or control chamber volumes are determined, at least in part, from measured pressures by utilizing an equation of state describing the pressure-volume behavior of a measurement gas, the pump chamber preferably includes a movable surface which comprises an elastic membrane. The restoring force of the elastic membrane, when stretched or displaced from a relaxed equilibrium condition, enables the pressure on each side of the membrane (i.e. in the pump chamber and control chamber) to be different, where the degree of difference in the pressures, and the resistance to further displacement/stretching (stress/elastic energy stored in the membrane), is a function of the degree of stretch or displacement from the relaxed equilibrium condition of the membrane. In such embodiments, it is also preferred that the measurement gas pressures applied to the elastic membrane during the determination of pump/control chamber volumes at the first and second conditions of applied force for detecting air/gas in the pump chamber discussed above, tend to stretch the elastic membrane (if air/gas is present in the pump chamber), from its equilibrium configuration before the pressure is applied, by a different extent for each condition, so that the stress in the membrane and its resistance to further displacement in response to a given level of applied pressure will be different for the first and second condition (or in other words, the force/displacement response of the elastic membrane for the first and second conditions will be asymmetrical). In such embodiments, the difference in the pressure in the control chamber versus the pressure in the pump chamber, at an equilibrium condition, will be different for the first condition of applied pressure versus the second condition of applied pressure. In such embodiments, without being tied to any particular physical mechanism, it is believed that the different level of stress and strain of the elastic membrane during measurements of pump/control volume determined at the first and second conditions above create, at least in part, deviations in the pressure-volume behavior of the measurement gas from that predicted for each condition by the equation of state, which deviations can create and/or enhance a difference in the volume of the pump/control chamber determined for each condition by using the equation of state.

Figure 4:
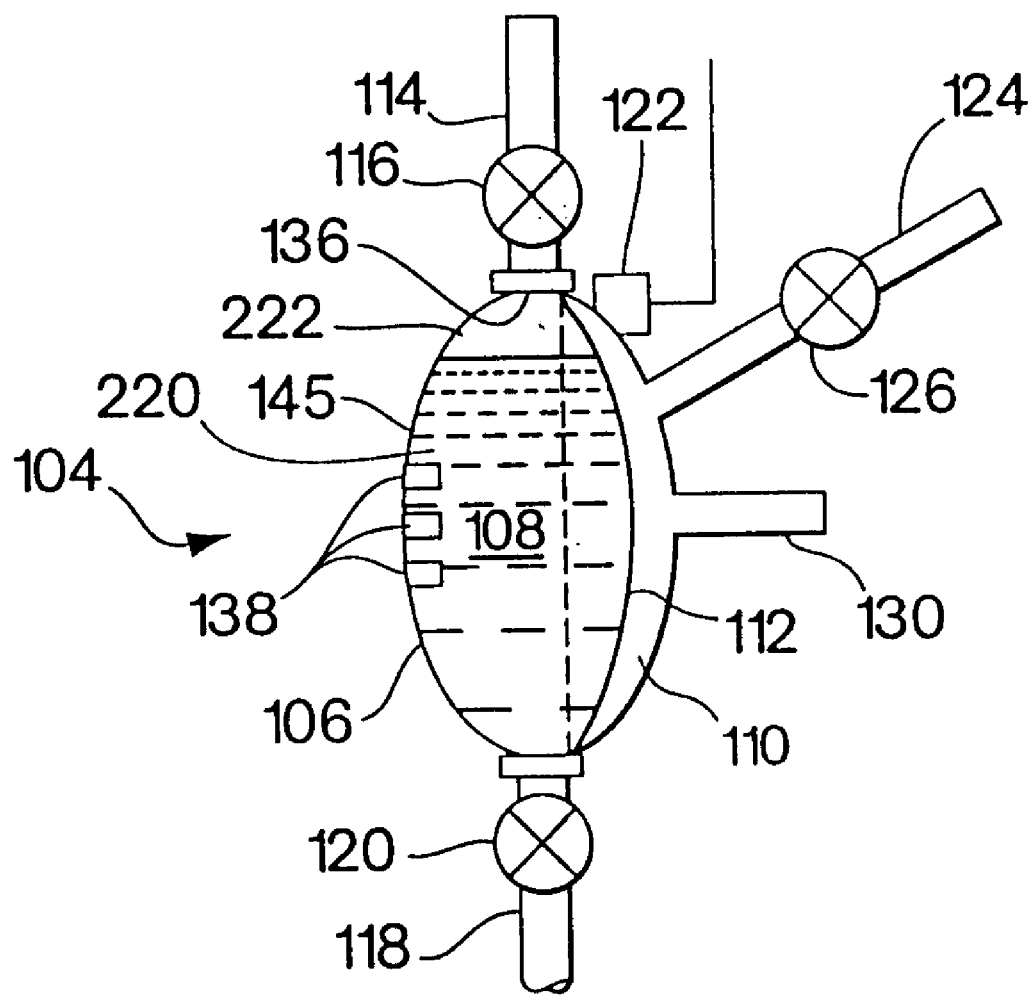
FIG. 4 is a schematic illustration of the pump of FIG. 1 at a first condition of fluid pressure in the control chamber.

In some embodiments, one way to achieve or enhance such asymmetry in the response of the elastic membrane to the applied measurement gas pressures utilized during volume determinations for gas detection is to perform the volume determination steps when the pump chamber flexible elastic membrane has already been stretched, from the configuration it has at a relaxed equilibrium condition, with essentially equal fluid pressures on each side of the membrane, before the application of pressurized measurement gas to the membrane for the purpose of volume measurement. This can be accomplished, for example, by performing the volume determinations related to air/gas detection after filling the pump chamber with sufficient liquid so that the elastic membrane is at least somewhat stretched, and preferably substantially stretched, by displacement of the membrane in the direction of the control chamber, and by using a positive measurement gas pressure during volume measurement at the first condition and a negative measurement gas pressure during volume measurement at the second condition (or vis versa). Such a condition of displacement of elastic membrane 112 for pump 104 is illustrated in FIG. 4, which shows pump chamber 108 after filling with a liquid 220 to be pumped and immediately before volumetric measurements performed (as described below) for detecting the presence of a gas 222 in the pump chamber. In alternative embodiments the desired asymmetry in the response of the elastic membrane during volume determinations involved in air/gas detection could also be achieved by utilizing levels of measurement gas pressures applied to the elastic membrane for volumetric determinations performed at the first and second conditions of measurement that are selected to impart a different, and preferably substantially different degree of elastic stretch to the membrane. While preferred embodiments of pump chambers for use when utilizing an equation of state based procedure for calculating pump/control chamber volumes include a moveable surface at least partially comprised of an elastic membrane, in alternative embodiments, non-elastic movable surfaces could potentially be used so long as the measurement fluid pressures applied to the surface during volume measurement at the first condition and second condition create a different a levels of stress in the surface and different differences in the equilibrium pressures within the control and pump chamber. Such embodiments could, for example, utilize a non-elastic movable surface or flacid membrane, where measurement fluid pressures applied during the first condition of volume determination tend to move the surface/membrane (if a gas is present in the pump chamber) to its maximum allowed displacement so that the surface is no longer free to move in response to the applied force, a stress is created in the surface/membrane, and a pressure difference exists between the pump and control chambers. Measurement of volume at a second condition for such embodiments could apply a different measurement fluid pressure to the surface, which pressure tends to move the surface/membrane (if a gas is present in the pump chamber) to reduce or substantially eliminate the stress within the surface/membrane so that at equilibrium, the difference in pressure in the pump and control chambers is reduced or essentially eliminated.

Referring again to the protocol of FIG. 3, initially, it will be assumed that pump chamber 108 has been emptied, and that elastic membrane 112 is extending into pump chamber 108 at its maximum allowable displacement defined by line 142. Piston 132 is assumed to be at its far left position of travel (shown as position I in FIG. 1). Referring to FIG. 3a, step 1 (170) involves initializing the system so that all valves are closed and piston 132 and flexible membrane 112 are in the positions described above.

Step 2 (172) involves filling the pump chamber 108 with a liquid to be pumped. The step involves first opening inlet valve 116, then actuating motor 133 so as to move piston 132 to position 3 shown in FIG. 1, thereby increasing the volume of pump chamber 108 by an amount defined as ΔV. Then, inlet valve 116 is closed in order to isolate pump chamber 108.

Step 3 (174) of the exemplary pumping cycle involves a series of sub-steps for determining the volume of control chamber 110 and/or pump chamber 108 and for detecting the presence of any gas contained within pump chamber 108. Step 3 (174) is described in greater detail in FIG. 3b.

Referring again to FIG. 3a, step 4 (208) of the pumping cycle involves delivering the liquid contained in pump chamber 108. First, outlet valve 120 is opened. Motor 134 is then actuated to move piston 132 from position 3 to position 1, thereby delivering a volume of fluid ΔV. Outlet valve 120 is then closed in order to isolate pump chamber 108. In some embodiments, where the accuracy of determining the volume delivered by pump chamber 108 is critical, the volume of pump chamber 108 after step 4 (208) may be determined (e.g., by repeating substeps 1–4 (176, 178, 180, 182) of the volume calculation and air detection subcycle of FIG. 3b described below). In which case, the volume delivered for the above described pump stroke can be determined by taking a difference in the volume of pump chamber 108 determined in step 3 (174) and in step 5 (210). Finally, if multiple pump strokes are desired, the entire pump cycle of FIG. 3a may be repeated.

Referring to FIGS. 3b–3c, one embodiment of a volume calculation and gas detection method, shown at step 3 (174) of FIG. 3a, is shown. Substep 1 (176) of subcycle 174 involves measuring the pressure $P_1$ of the measurement gas in control chamber 110 with pressure transducer 122 and recording or storing the pressure with processor 134. In substep 2 (178) piston 132 is moved from position 3 to position 1 thereby reducing the volume of the measurement gas contained within the system by ΔV. In substep 3 (180) the pressure of the measurement gas in control chamber 110 is measured again and recorded as $P_2$. It will be appreciated that $P_2$ will be greater than $P_1$ due to the compression of measurement gas within the system. The volume of fluid contained in pump chamber 108 is then determined in substep 4 (182), with the pump chamber at this first condition, using an appropriate equation of state for the measurement fluid being utilized. In the case of a measurement gas, such as air, for systems utilizing pumping pressures which are relatively low (typical pumping pressures utilized by pumping systems according to the invention range from abut −14 psig to about 15 psig) the ideal gas law can be employed. Recognizing that no measurement gas was added to or removed from the system, and utilizing the ideal gas law combined with conservation of mass, the volume of fluid contained in pump chamber 108 is determined by:

$$V_F = V_T - \frac{P_2 \Delta V}{P_2 - P_1} \quad (1)$$

Equation 1 assumes that any temperatures changes or differences caused by changing the volume of measurement gas are minimal and that the system is essentially isothermal. It will be appreciated that for systems where temperature changes may be significant, the temperature dependence of the measurement fluid, as defined by the equation of state being used, may be incorporated into the volume calculation of substep 4 (182) in a straightforward fashion, as apparent to those of ordinary skill in the art. $V_F$ in equation 1 refers to the internal volume of pump chamber 108 and $V_T$ refers to the known total volume of the system including pump chamber 108, control chamber 110, and the volumes contained within measurement fluid inlet line 130 and cylinder 128.

The remaining substeps of the volume calculation subcycle 174 involve redetermining the volume of the pump chamber 108 at a different condition and comparing the volumes determined at the first and second conditions. In substep 5 (184) of FIG. 3b, control chamber vent valve 126 is opened to equilibrate the pressure in control chamber 110 with the surrounding atmosphere. Vent valve 126 is then closed. A new pressure $P_1$ is measured with transducer 122 in control chamber 110 in substep 6 (186). In substep 7 (188) piston 132 is moved from position 1 to position 3 thereby increasing the volume of measurement gas within the system by ΔV. In substep 8 (190) the new pressure $P_2$ in control chamber 110, which pressure will be below atmospheric pressure, is measured and recorded. In substep 9 (200) the volume of pump chamber 108 $V_F$ is calculated as described above in substep 4 (182). Substep 10 (202) involves determining the difference between $V_F$ determined in substep.4 (182) and $V_F$ determined in substep 9 (200) and taking an absolute value of the difference. In substep 11 (204), shown in FIG. 3c, the above difference is compared to a predetermined limit that is proportional to a maximum allowable quantity of air or other gas which can be present in pump chamber 108 during operation. The predetermined limit is typically determined empirically, as discussed below, and chosen such that air volume exceeding dead space 144 volume will also exceed the predetermined limit. If the difference exceeds the predetermined limit the processor 134 will create an alarm condition and initiate an air purge, as described in more detail below.

If the difference in measured volumes is less than the allowable limit (204), the system will proceed to pump the liquid contained in pump chamber 108. In substep 12 (206) the system opens control chamber vent valve 126 in order to equilibrate the pressure in control chamber 110 and the surrounding atmosphere, and then closes vent valve 126. Pumping system 100 is now in condition to deliver the liquid contained in pump chamber 108.

As described above, the measured volumes at the two different conditions can be compared to detect the presence of gas in the pump chamber. If the presence of a gas is detected in the pump chamber and is of sufficient quantity to cause the system to set off an alarm, as described above in substep 11 (204) FIG. 3c, instead of proceeding to deliver the fluid to a desired downstream destination as described above, the pumping system 100 will instead initiate an air purge. During the air purge, instead of outlet valve 120 being opened while fluid is being pumped from pump chamber 108, inlet valve 116 is opened, and the fluid, including any gas in the pump chamber, is pumped from the pump chamber through inlet line 114 to a safe purge destination.

It should be appreciated that while the above described example of a pump stroke cycle for pumping system 100 was described as being fully controlled, and regulated by a processor, the method could equivalently be performed under manual operator control without utilizing such a processor or by using any other mechanism to control the operation. In addition, while the above described methods involve an essentially ideal gas as a measuring fluid, other embodiments of the invention may utilize non-ideal measurement gases, or liquids as measurement fluids. When such alternative measurement fluids are used, the ideal gas law may no longer be an appropriate equation of state to utilize for determining volumetric measurements but instead an equation of state appropriate for the measurement fluid being used may be utilized. In addition, as discussed earlier, a variety of other techniques for measuring the volume contained in a volumetric container can be used to determine a measured parameter related to the volume of a pump chamber having a movable surface or flexible membrane at a first and second condition of applied force, such alternative means of volumetric measurement being apparent based on the disclosure herein and are within the scope of the present invention. In addition, also as discussed previously, the skilled practitioner will envision many alternative mechanisms for applying a variable level of force to a moveable wall, for example flexible elastic membrane 112, or other movable wall configuration, of a pump chamber, which can be substituted for the pressurized gas pump drive system 230 described in FIG. 1. It should also be emphasized that the particular steps described as part of the exemplary pump cycle methods described herein may be performed in a different sequence, and certain steps may be substituted or eliminated, without effecting the overall performance of the methods. For example, when detecting the presence of a gas in the pump chamber, instead of applying a positive pressure to the flexible membrane of the pump chamber to calculate a first volume followed by applying a negative pressure to the flexible membrane of the pump chamber to calculate a second volume, these steps could easily be interchanged or both pressures may be positive or negative, so long as they differ by a sufficient amount to enable the detection of gas in the pump chamber.

Figure 5:
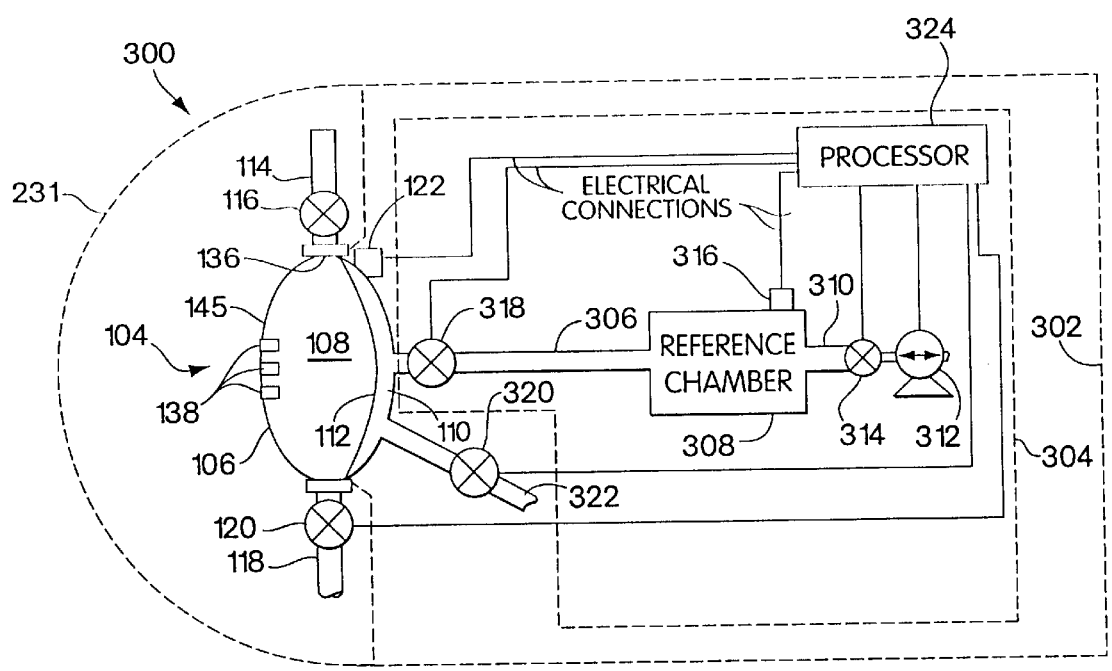
FIG. 5 is a schematic illustration of a pumping system according to one embodiment of the invention.

FIG. 5 shows a pumping system 300 utilizing an alternative pump drive system 302 including a measurement fluid supply system 304 which is a constant volume system. Fluid supply 304 is able to apply a force to flexible membrane 112 of pump chamber 108 by changing the quantity of a measurement gas contained within constant volume fluid supply system 304. Pump drive system 302 of pumping system 300 includes a control chamber 110 which is connected via measurement gas inlet line 306 to a reference chamber 308 having a known volume. Measurement gas is supplied to reference chamber 308 and control chamber 110 via pump 312. Pumping system 300 also includes a processor 324, similar to that described previously for pumping system 100 shown in FIG. 1, which is configured to control the operation of the various components of the system and perform determinations of measured parameters related to the volume of pump chamber 108, as described in more detail below.

Figure 6A:
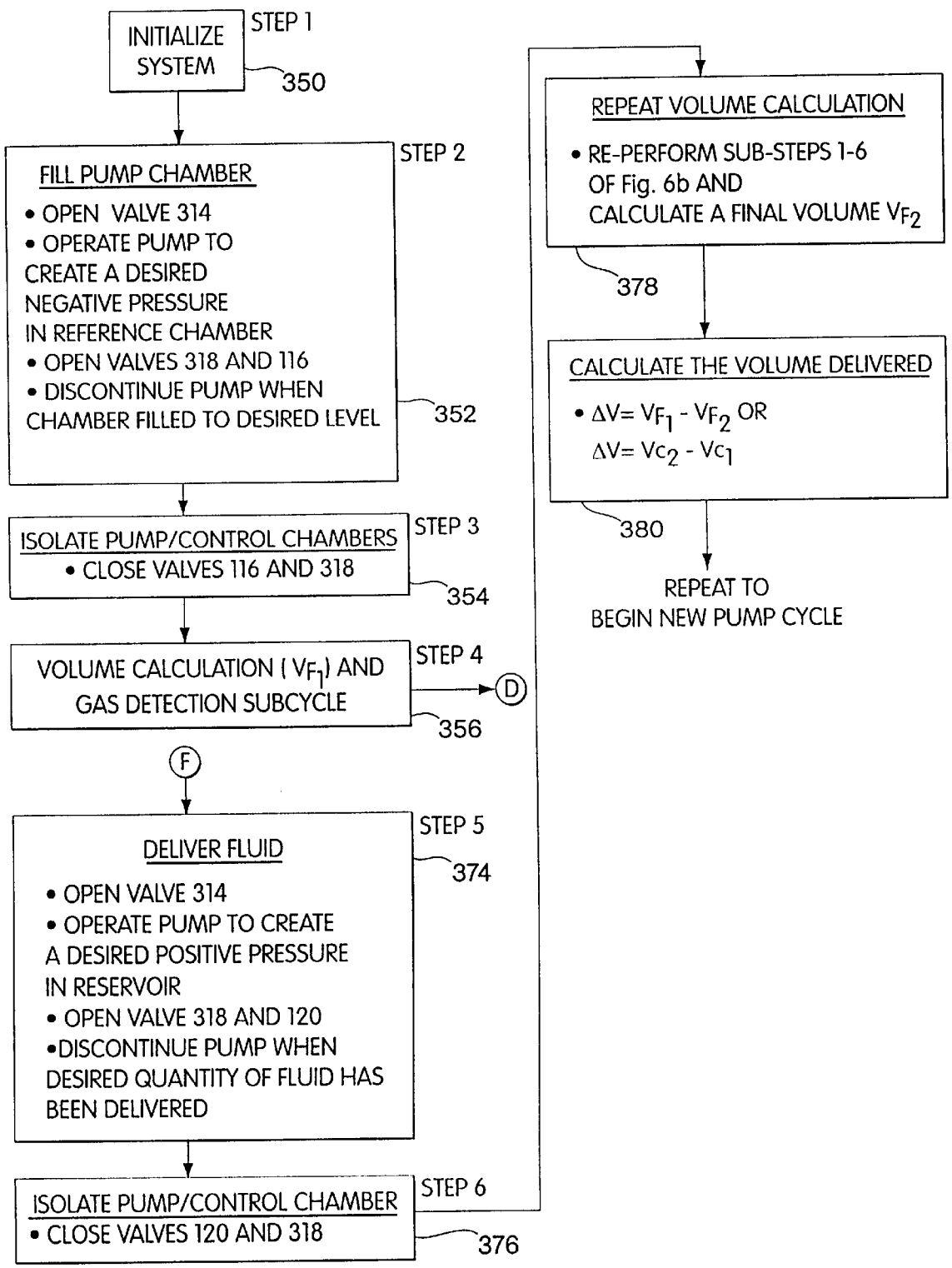
FIG. 6a is a flow chart illustrating a series of steps in a pumping cycle according to one embodiment of the invention.
Figure 6B:
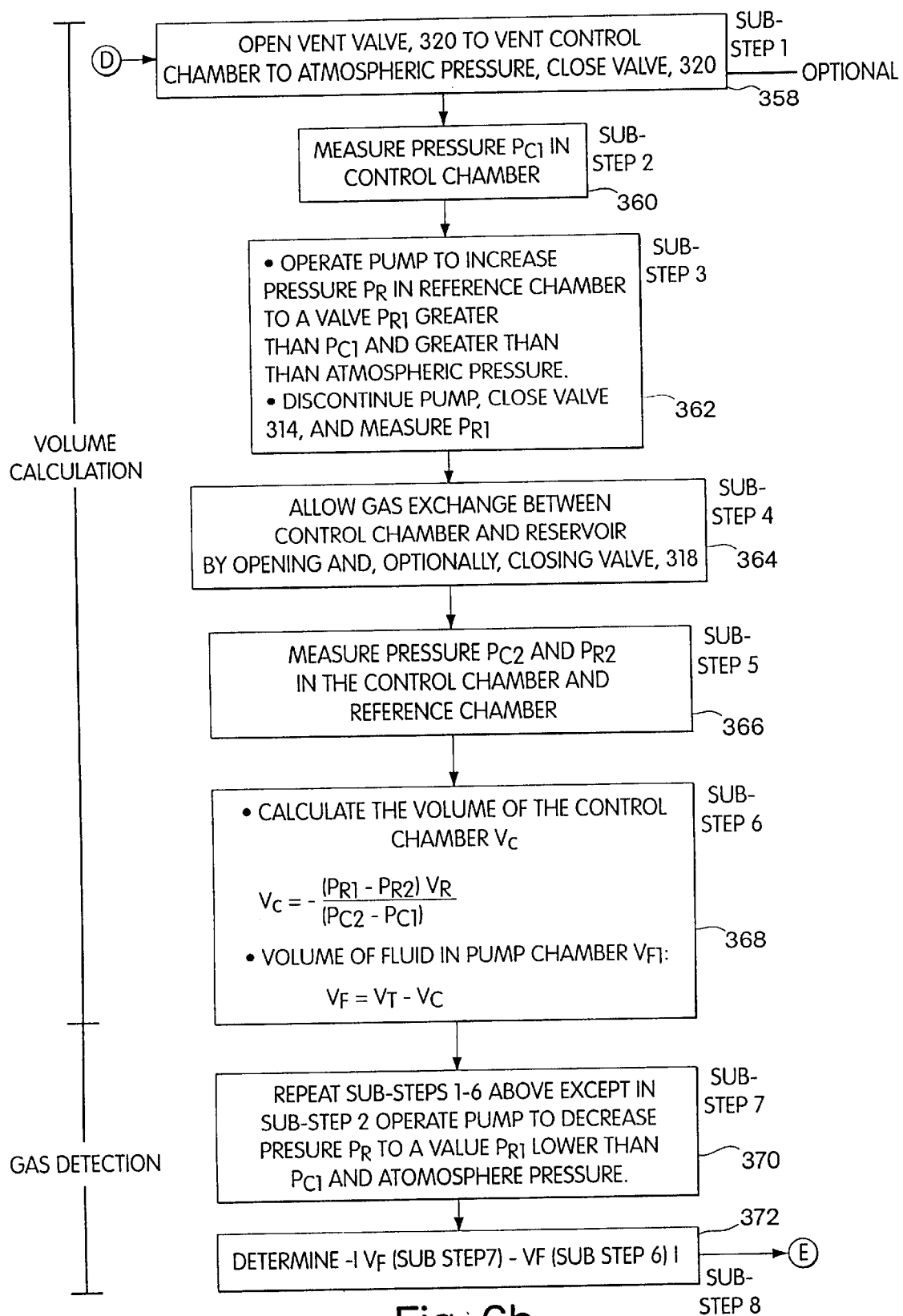
FIG. 6b is a flow chart illustrating a series of substeps of the pumping cycle of FIG. 6a for performing volume calculation and air detection.
Figure 6C:
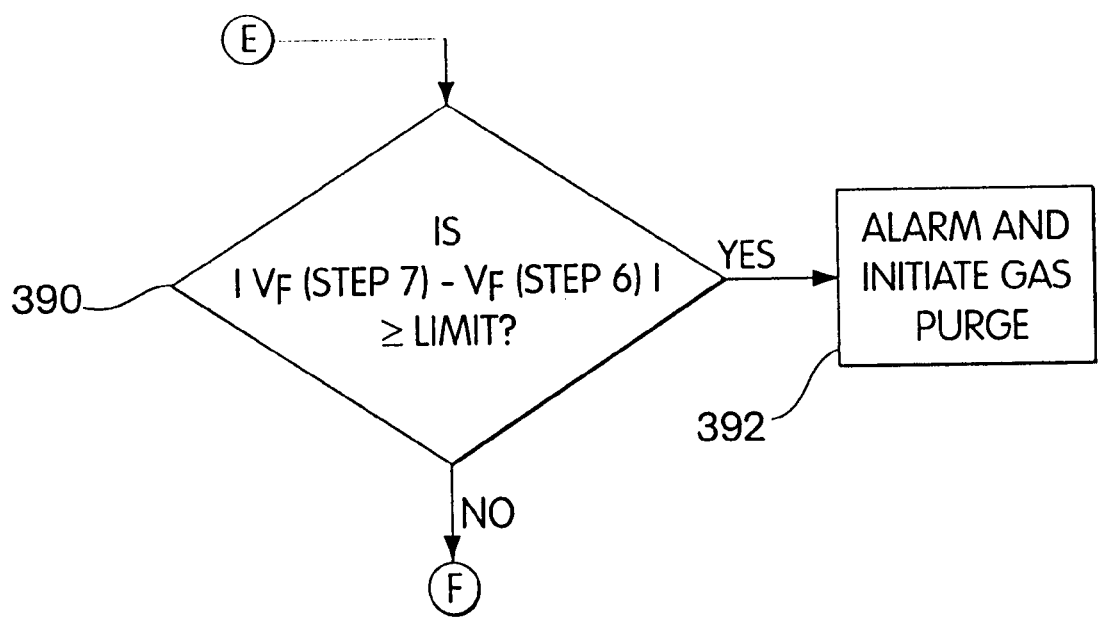
FIG. 6c is a flow chart illustrating a series of substeps of the pumping cycle of FIG. 6a for detecting the presence of a gas in a pump chamber.

An exemplary embodiment of a pump stroke cycle, including the detection of a gas in pump chamber 108 utilizing the ideal gas law in determining pump chamber volumes, which can be utilized for operating pumping system 300 is described in FIGS. 6a–6c. Referring to FIG. 6a, initially, it is assumed that pump chamber 108 has been emptied and flexible membrane 112, preferably an elastic membrane as previously discussed in the context of system 100 of FIG. 1, is displaced into pump chamber 108 as described previously with regard to FIG. 3a. In addition, in the initial state of the system in step 1 (350) it is assumed that all valves of the system are closed. Step 2 (352) of the method involves filling pump chamber 108 with a liquid through inlet line 114 and inlet valve 116. The step involves first opening valve 314 located on line 310 between reference chamber 308 and pump compressor 312, and operating pump 312 to create a desired negative pressure in reference chamber 308, as measured by pressure transducer 316. Next, valve 318 on line 306 and inlet valve 116 are opened. The operation of pump 312 can be discontinued when pump chamber 108 has filled with liquid to a desired extent. In step 3 (354) of the method, pump chamber 108 and control chamber 110 are isolated by closing inlet valve 116 and valve 318.

Step 4 (356) comprises a volume calculation and air detection subcycle described below in more detail with reference to FIG. 6b. The liquid contained in pump chamber 108 is delivered through outlet line 118 in step 5 (374). Step 5 (374) involves opening valve 314, operating pump 312 to create a desired positive pressure in reference chamber 308, opening valves 318 and outlet valve 120, and allowing the liquid contained in pump chamber 108 to flow through outlet line 118 until a desired quantity of liquid has been delivered. At which point, in step 6 (376), outlet valve 120 is closed, so as to isolate pump chamber 108, and valve 318 is closed to isolate control chamber 110. In step 7 (378) the final volume of pump chamber 108 is determined (e.g., by re-performing substeps 1–6 of FIG. 6b described below and calculating a final volume $V_{F2}$). The volume delivered by pump chamber 108 during the pump stroke is calculated in step 8 (380) by taking a difference between the pump chamber volume $V_{F1}$ determined in step 4 (356) and the pump chamber volume $V_{F2}$ determined in step 7 (378). For embodiments involving delivery of liquids via multiple pump stroke cycles, the steps described in FIG. 6a can be repeated.

FIG. 6b shows one embodiment of a method for determining gas volume in the method of FIG. 6a step 4 (356). Substep 1 (358) comprises an optional step whereby the pressure in control chamber 110 is equilibrated to the atmosphere by opening an optional vent valve 320 located on optional vent line 322 connected to control chamber 110. After equilibration with the atmosphere, vent valve 320 is closed. In substep 2 (360) pressure $P_{C1}$ in control chamber 110 is measured with pressure transducer 122 and stored by processor 324. In substep 3 (362), pump 312 is operated so as to increase the pressure $P_R$ in reference chamber 308 to a value $P_{R1}$ that is greater than $P_{C1}$ and also greater than atmospheric pressure. After such pressure in reference chamber 308 is obtained, the operation of pump 312 is discontinued, valve 314 is closed, and pressure $P_{R1}$ in reference chamber 308 is measured with pressure transducer 316 and stored by processor 324.

Substep 4 (364) involves allowing a quantity of measurement gas to be exchanged between control chamber 110 and reference chamber 308. This can be accomplished by opening and, optionally, closing valve 318. If desired, valve 318 may be opened for a sufficient time to allow the pressure in control chamber 110 and reference chamber 308 to equilibrate to a common value. For embodiments where the pressures in control chamber 10 and reference chamber 308 are allowed to equilibrate in substep 4, the system can compare the pressure signals obtained from pressure transducer 122 and pressure transducer 316 and can create an alarm condition indicating a system fault if the pressures do not essentially agree.

In substep 5 (366) the system determines pressure $P_{C2}$ in control chamber 110 and $P_{R2}$ in reference chamber 308 and records the pressures ($P_{C2\ and\ PR2}$ should be essentially the same if the pressures in control chamber 110 and reference chamber 308 were allowed to equilibrate in substep 4 above).

In substep 6 (368) the volume of the control chamber 110, (which also includes the volume of line 306 up to valve 318 and line 322 up to valve 320) is determined at this first set of conditions of measurement (or "first condition" as used herein) from the known volume of reference chamber 308 and the pressures determined above utilizing the ideal gas law equation of state and conservation of mass for the measurement gas exchanged during substep 4 (364) above. As described for the previous embodiment, equations of state other than the ideal gas law may be used for measurement fluids which do not simulate ideal gas behavior. Also, as before, the system is assumed to be isothermal, specifically, the temperature in reference chamber 308 is assumed to be equal to the temperature in control chamber 110 during pressurization and gas exchange. The volume of the control chamber described above $V_C$ is determined by:

$$V_C = \frac{(P_{R1} - P_{R2})V_R}{(P_{C2} - P_{C1})} \quad (2)$$

where $V_R$ is the known volume of reference chamber 308. The volume of fluid in pump chamber 108 may be explicitly determined, if desired, by subtracting $V_C$ from $V_T$, which is the known total volume of pump chamber 108 and control chamber 110.

In substep 7 (370) and substep 8 (372) the presence of any gas contained in pump chamber 108 is determined. In substep 7 (370), substeps 1–6 (358, 360, 362, 364, 366, 368) described above are repeated, except that in substep 2, pump 312 is operated so as to decrease the pressure in reference chamber 308 to a value lower than that of the pressure in control chamber 110 and atmospheric pressure. In substep 8 (372) the processor determines the difference between the volume of pump chamber 108 determined in substep 7 (370) (i.e. the volume determined at the second set of measurement conditions or "second condition" as used herein) and the volume of pump chamber 108 determined in substep 6 (368).

As shown in FIG. 6c, the value of the difference in the calculated volumes is compared to a predetermined threshold limit (step 390), and if the value exceeds the limit processor 324 creates an alarm condition and initiates an air purge (step 392), similar to that described previously. If the system fails to detect any gas in pump chamber 108 (i.e., the difference in the measure volumes is below the threshold limit) the system will proceed to deliver liquid contained in pump chamber 108, as described in more detail in FIG. 6a.

Figure 7:
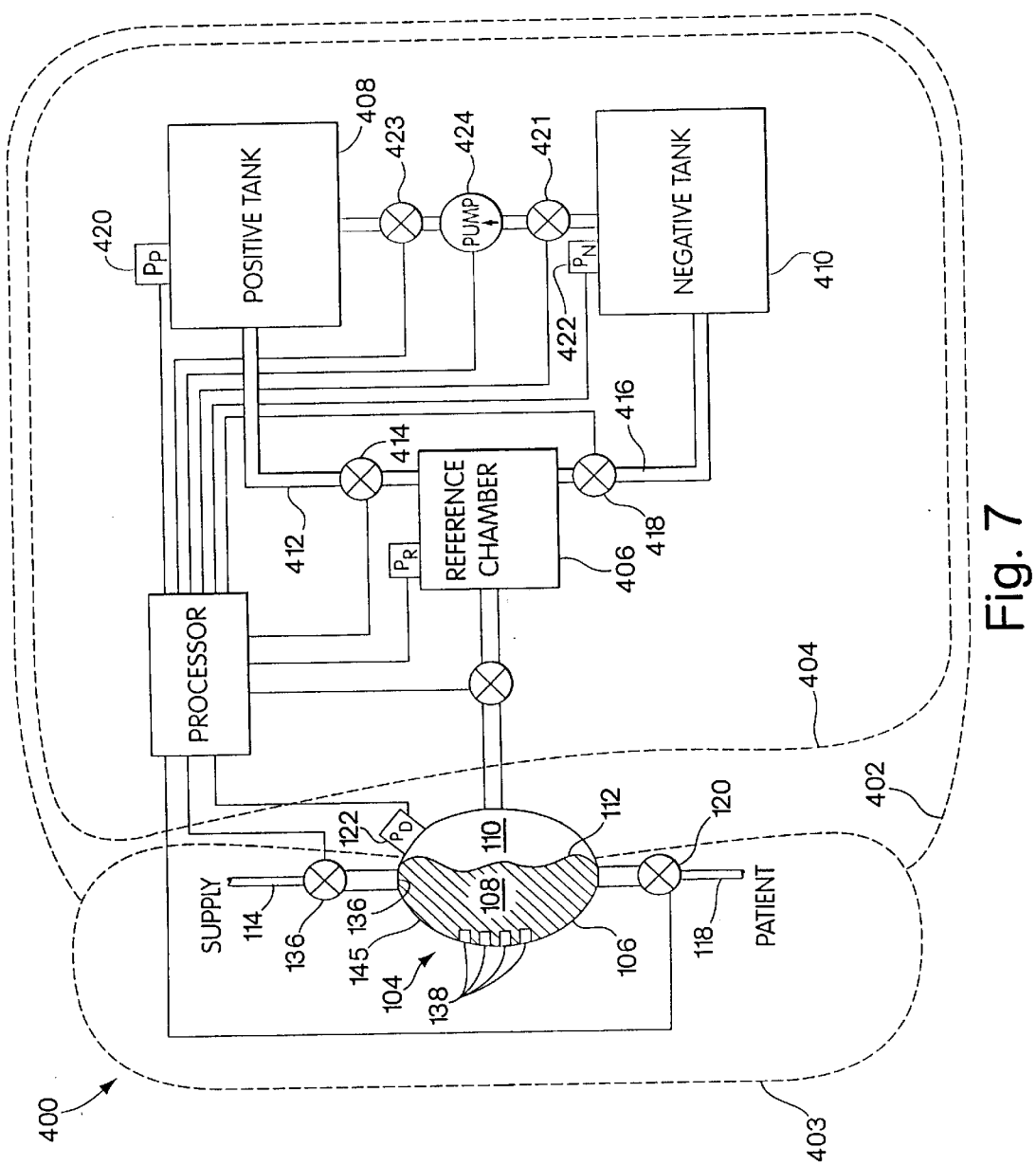
FIG. 7 is a schematic illustration of a pumping system according to one embodiment of the invention.

An alternative embodiment to the pump system 300 shown in FIG. 5, which also utilizes a pump drive system including a fluid supply system having a constant known volume, is shown in FIG. 7. A pumping system 400 having a pump drive system 402 including a fluid supply system 404 including a reference chamber 406 having a known volume. As opposed to system 300 shown in FIG. 5, where the measurement gas was supplied to reference chamber 308 by a pump 312, in pumping system 400, measurement gas is supplied to reference chamber 406 via a positive pressure storage tank 408 and a negative pressure storage tank 410. Positive pressure storage tank 408 is connected to reference chamber 406 via line 412 containing a valve 414 therein. Negative pressure tank 410 is connected to reference chamber 406 via line 416 containing a valve 418 therein. In preferred embodiments, positive pressure tank 408 and negative pressure tank 410 each include pressure transducers 420 and 422 for continuously monitoring the pressure of a measurement gas contained therein. As illustrated in the figure, fluid supply system 404 of pumping system 400 is a completely closed system wherein measurement gas is contained within the system without additional quantities of measurement gas being added to or removed from the system during the pump cycle. However, in alternative embodiments, the system can include one or more lines for fluid communication with the environment for venting or other purposes. In one such alternative embodiment, instead of pump 424 creating a pressure difference between tanks 408 and 410 by pumping measurement gas from tank 410 to 408, the pump could pump air from the surroundings to tank 408 and could pump air from tank 410 to the surroundings to create the pressure difference.

Before the beginning of a pump cycle which utilizes pumping system 400, a pressure differential between positive tank 408 and negative tank 410 is established by opening valves 421 and 423 and operating pump 424 to move measurement gas from negative tank 410 to positive tank 408. The pump cycle and volume measurement cycle utilizing system 400 is similar to that described for system 300 of FIG. 5, except that in order to create a positive pressure of measurement gas in reference chamber 406 and control chamber 110 and in order to create a different (in this example, negative) pressure in reference chamber 406 and control chamber 110 the chambers are placed in fluid communication with positive tank 408 and negative tank 410 respectively, instead of establishing the pressures by utilizing a pump.

Pumping system 400 enables a more constant and controllable pressure to be applied to control chamber 110 during the filling and emptying of pump chamber 108, as compared to pump system 300 shown in FIG. 5. Preferably, positive tank 408 and negative tank 410 have internal volumes that are substantially greater than the internal volume of reference chamber 406 and control chamber 110. In preferred embodiments, positive tank 408 and negative tank 410 have volumes that are sufficiently greater than those of reference chamber 406 and control chamber 110 so that the pressure of measurement gas in tanks 408 and 410 remain essentially constant throughout the pump cycle. Typically, tanks 408 and 410 will be at least 10 times larger, and are preferably at least 20 times larger in volume than reference chambers 406 and control chamber 110. In general, for pumping systems utilizing a control chamber and a reference chamber (for example the systems shown in FIG. 5 and FIG. 7 and described below in FIG. 8) the control chamber preferably has a volume similar to or on the same order of magnitude as the volume of the pump chamber, and the reference chamber has a volume that is from about 1–10 times that of the control chamber.

It should be appreciated that the particular ways in which the various tanks, valves, pumps, and chambers of the various pumping systems described herein are arranged, configured, and interconnected can be varied considerably without changing the overall performance or operation of the pump drive system. A variety of alternative configurations for the pumping systems described herein have been previously described in U.S. Pat. Nos. 4,778,451, 4,808,161, 4,826,482, 4,976,162, 5,088,515, and 5,178,182, each of which is commonly owned and which are incorporated herein by reference in its entirety.

Figure 8:
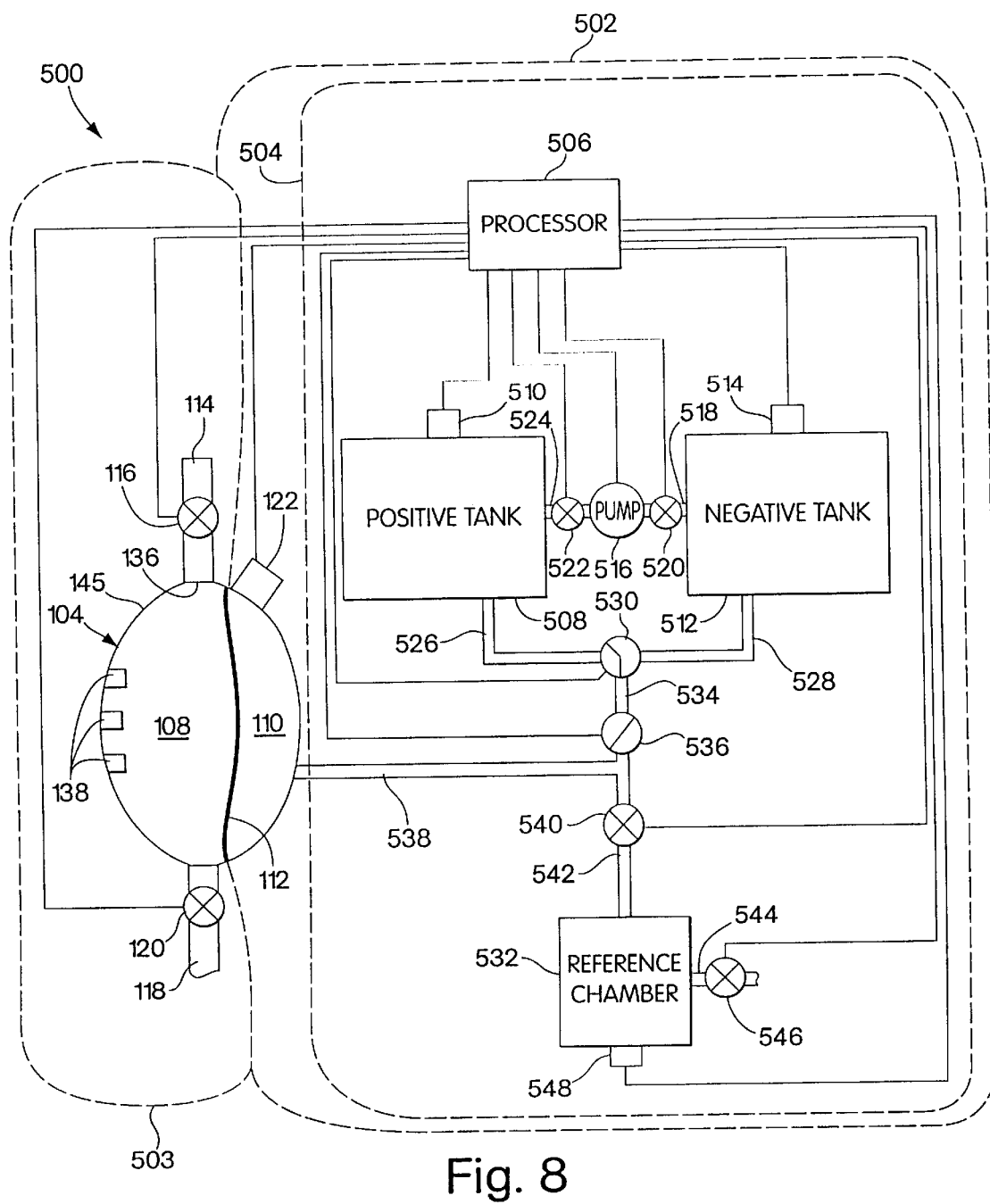
FIG. 8 is a schematic illustration of a pumping system according to one embodiment of the invention.

A preferred arrangement of components for providing a pump drive system according to the invention is shown in FIG. 8. Pumping system 500 includes a pump 104 including a pump chamber 108 separated from a control chamber 110 by a flexible membrane 112 disposed therebetween, similar to that described previously. Pumping system 500 includes a pump drive system 502 including a fluid supply system 504 connected in fluid communication with control chamber 110. Pump drive system 502 includes a processor 506 configured for controlling the various components of the system for pumping a liquid with pump chamber 108, and including a comparer for determining the presence of a gas in pump chamber 108 from measured parameters related to the volume of pump chamber 108, as described previously. Fluid supply system 504 includes a positive pressure source comprising a positive pressure tank 508 with a measurement gas having a positive pressure contained therein. Positive pressure tank 508 includes a pressure transducer 510 configured to measure the pressure of the measurement gas and send a signal to processor 506. Fluid supply system 504 also includes a negative pressure source comprising a negative pressure tank 512 having a measurement gas at a negative pressure contained therein. Negative pressure tank 512 includes a pressure transducer 514 for measuring the pressure of a measurement gas contained therein.

Fluid supply system 504 also contains a pump 516 positioned and configured to pump measurement gas from negative tank 512 through line 518, valve 520, valve 522 and line 524 to positive pressure tank 508, so as to establish a pressure difference between the measurement gas contained in positive pressure tank 508 and negative pressure tank 512. Positive pressure tank 508 has an outlet line 526 and negative pressure tank 512 has an outlet line 528, each of which lines are in fluid communication with a switch valve 530. The outlet of switch valve 530 is able to be placed in fluid communication with both control chamber 110 and reference chamber 532 of the system. Switch valve 530 is preferably a solenoid-operated three-way type valve which is controlled by processor 506 so that in a first position, positive pressure tank 508 is placed in fluid communication with control chamber 110 and/or reference chamber 532, and in a second position negative pressure tank 512 is placed in fluid communication with control chamber 110 and/or reference chamber 532.

Outlet line 534 from switch valve 530 includes a variable-sized orifice valve 536 therein, which valve comprises, in preferred embodiments, a valve having an orifice for fluid flow therethrough, where the size of the orifice is selectively adjustable over an essentially continuous range of values in order to control a flow rate of fluid therethrough. The size of the orifice in variable size orifice valve 536 is controlled, in preferred embodiments, by processor 506 in order to selectively vary the pressure of the measurement gas downstream of variable size orifice valve 536. Variable size orifice valves for use in the invention are known in the art and have been utilized for other purposes. Such valves are available, for example, from Parker Hannifin Corp., Pneutronics Division.

One embodiment of the present invention involves the novel incorporation of such a variable size orifice valve in a fluid supply system for measuring the volume of a volumetric chamber and, in some embodiments, for providing a pressurized fluid in contact with the moveable surface of a pump chamber.

The outlet of variable size orifice valve 536 is in fluid communication with measurement fluid inlet line 538, which provides measurement gas to control chamber 110. The outlet of variable size orifice valve 536 is also in fluid communication with valve 540 on inlet line 542 of reference chamber 532. Reference chamber 532, in preferred embodiments, also includes a vent line 544 through which measurement gas can be vented to the atmosphere by opening valve 546. Reference chamber 532 also includes a pressure transducer 548 in fluid communication therewith, which measures the pressure of a measurement gas in the reference chamber.

Figure 9A:
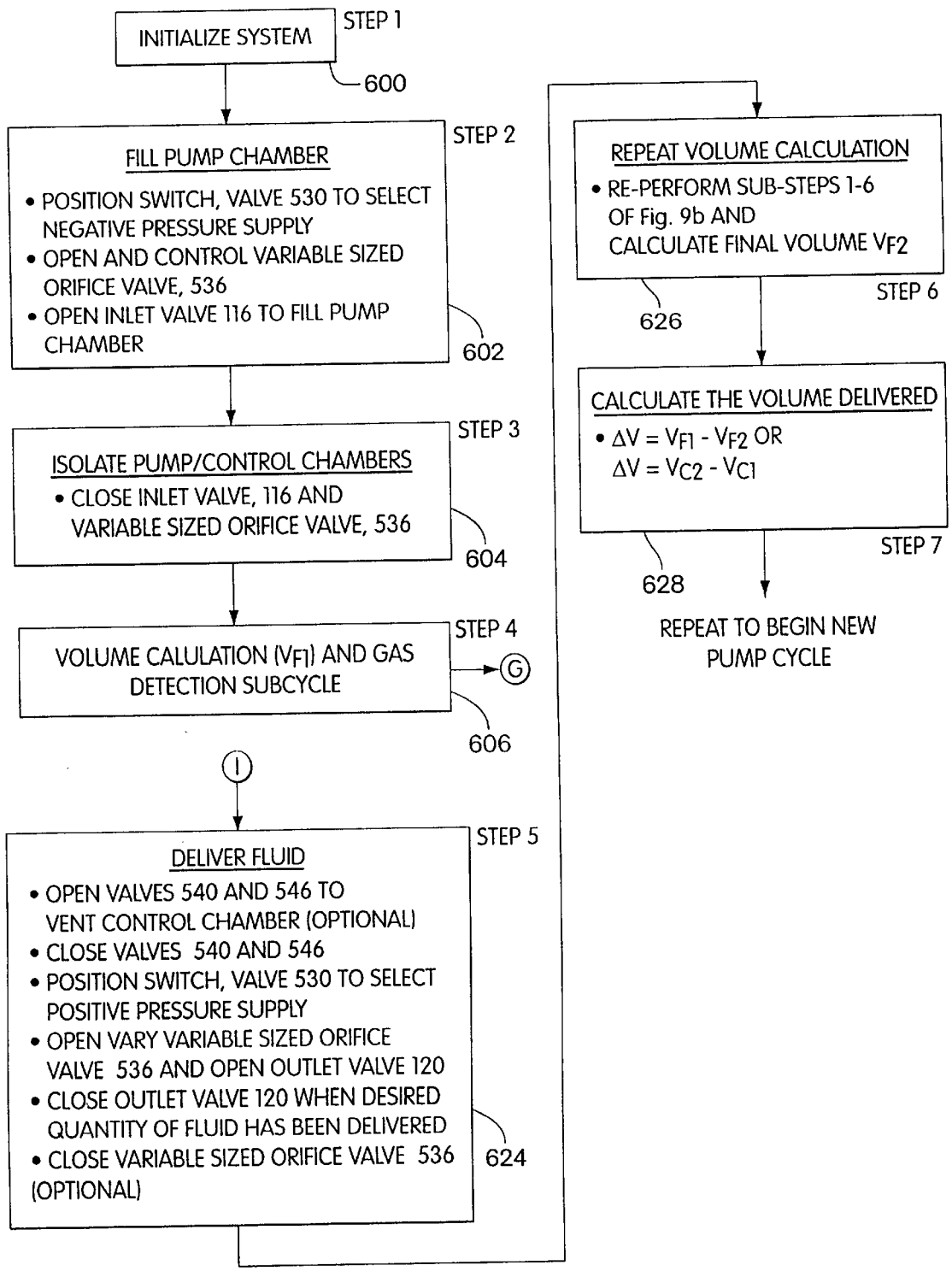
FIG. 9a is a flow chart illustrating a series of steps in a pumping cycle according to one embodiment of the invention.
Figure 9B:
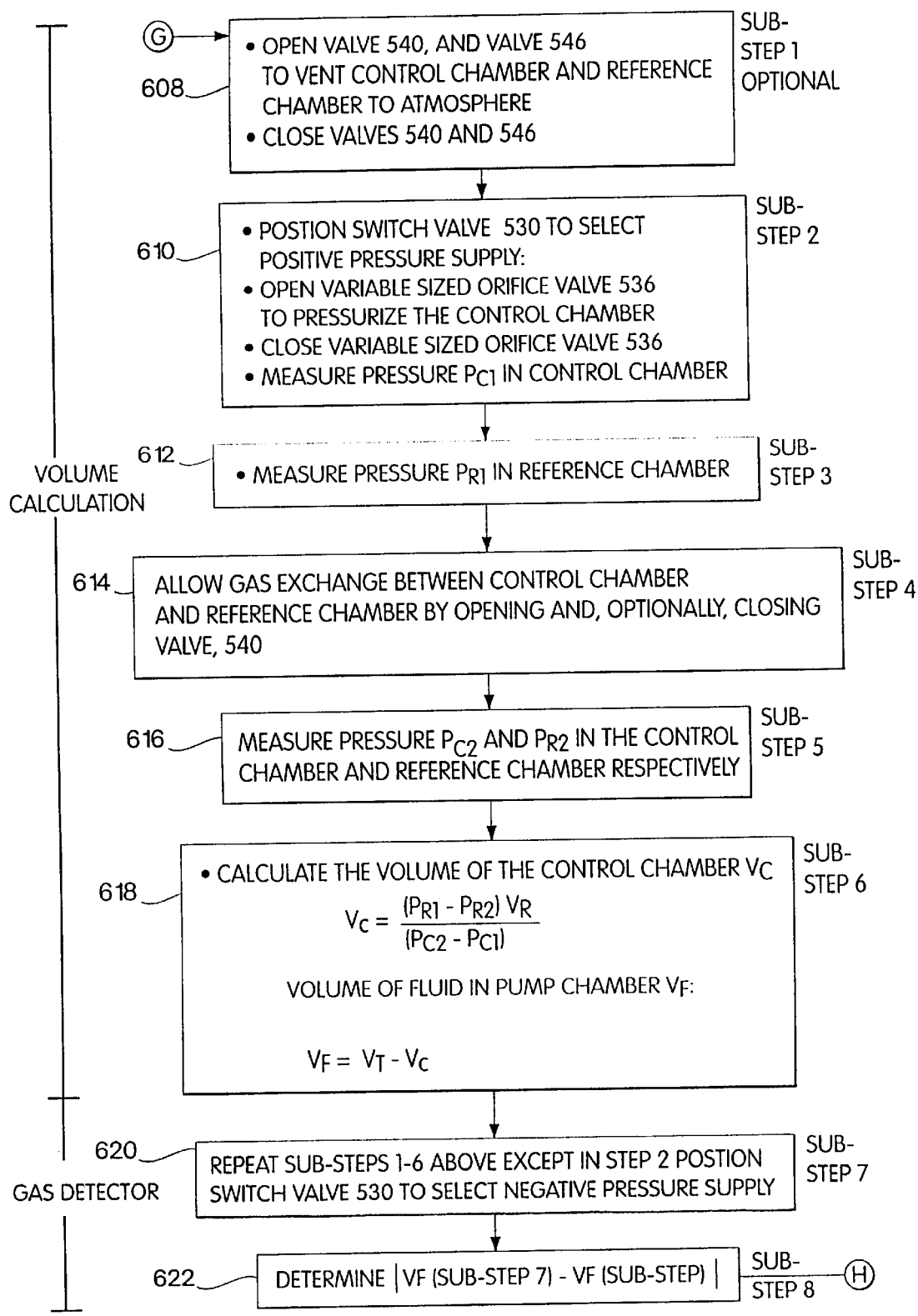
FIG. 9b is a flow chart illustrating a series of substeps of the pumping cycle of FIG. 9a for performing volume calculation and air detection.
Figure 9C:
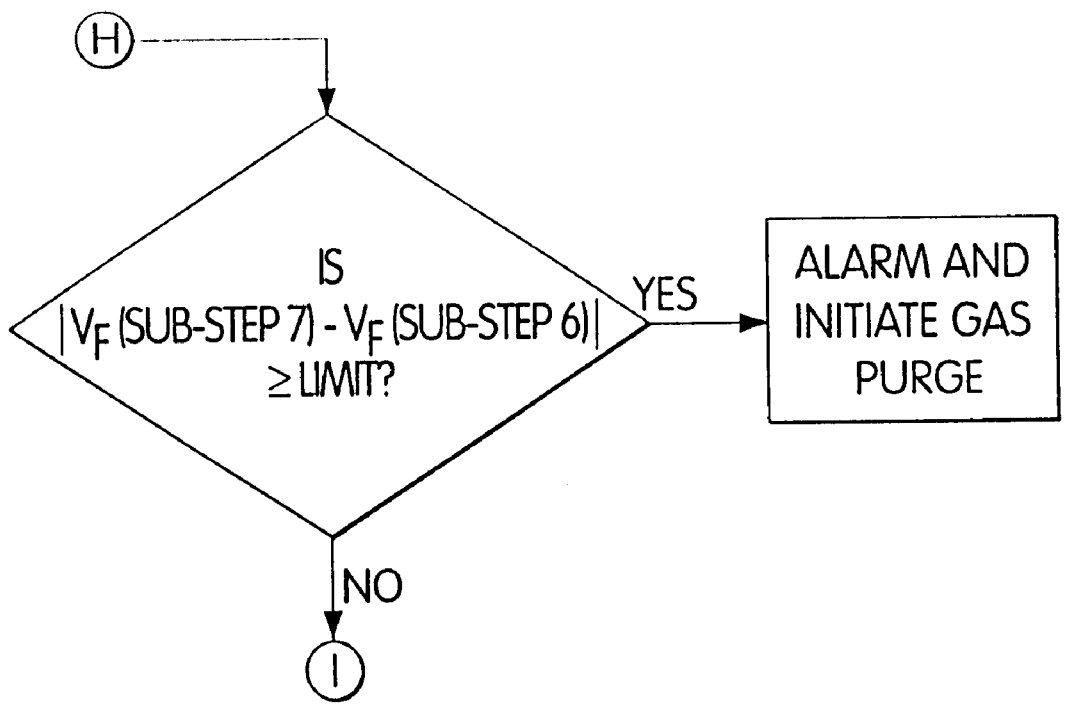
FIG. 9c is a flow chart illustrating a series of substeps of the pumping cycle of FIG. 9a for detecting the presence of a gas in a pump chamber.

One embodiment of a method for operating pumping system 500 is shown in FIGS. 9a–9c. The preferred pump stroke cycle includes steps for filling and dispensing a liquid from pump chamber 108, as well as steps for determining the volume of a volumetric container using the ideal gas law equation of state and conservation of mass, so as to determine a volume of liquid pumped and to detect the presence of any gas in pump chamber 108. As above, it is assumed initially that pump chamber 108 has been emptied of liquid and that flexible membrane 112, preferably an elastic membrane when, as here, pump chamber volumes are determined using the ideal gas law or other equation of state (as previously discussed), is extending to the maximum permissible extent allowed by spacers 138 into pump chamber 108. Step 1 (600) involves initializing the system. The initialization of the system involves opening valves 520 and 522 and operating pump 516 to create a desired pressure of measurement gas in positive pressure tank 508 and negative pressure tank 512, followed by discontinuing the operation of pump 516 and closing valves 520 and 522. It is also assumed as an initial condition that all valves of the system are closed and that switch valve 530 is positioned so that its outlet is in fluid communication with positive pressure tank 508.

Step 2 (602) involves filling pump chamber 108 with liquid through inlet line 114 and inlet valve 116. First, switch valve 530 is positioned to select negative pressure tank 512. Next, inlet valve 116 is opened and variable size orifice valve 536 is opened until pump chamber 108 has filled with liquid. In preferred embodiments, variable size orifice valve 536 is also selectively controlled during filling so as to provide an essentially constant negative pressure in control chamber 110, as described in more detail below. As will also be described in more detail below, the ability to vary the pressure in control chamber 110 via control of variable size orifice valve 536 enables system 500 to detect when flexible membrane 112 is distended into control chamber 110 to its maximum permissible extent indicating that pump chamber 108 is completely full of liquid. Thus, in preferred embodiments, system 500 can detect when pump 104 has reached the end of a stroke, either in the filling or emptying of pump chamber 108. This end of stroke detection method of preferred embodiments for operating pump system 500 is described in more detail below.

In step 3 (604) pump chamber 108 and control chamber 110 are isolated by closing inlet valve 116 and variable size orifice valve 536 respectively. Step 4 (606) comprises a subcycle which determines the volume of the volumetric container comprising pump chamber 108 and/or the volumetric container comprising control chamber 110, and determines the presence of any gas in pump chamber 108 utilizing the determined volumes. The various substeps of step 4 (606) are outlined in detail in FIGS. 9b and 9c.

Referring to FIG. 9b, substep 1 (608), which is optional, involves equilibrating the pressure in control chamber 110 and reference chamber 532 with the atmosphere by opening valve 540 and valve 546 in order to vent the control chamber and the reference chamber through vent line 544. Substep 2 (610) involves positioning switch valve 530 to select positive pressure supply tank 508, and opening variable size orifice valve 536 in order to pressurize control chamber 110. In some embodiments, variable size orifice valve 536 can be opened for a sufficient period of time so that the pressure of measurement gas in positive pressure supply tank 508 in control chamber 110 is allowed to equilibrate. In such embodiments, the pressure measured by transducer 122 on control chamber 110 should be essentially the same as that measured with pressure transducer 510 on the positive pressure tank. If these pressures do not agree, processor 506 can be configured to indicate that there is a system fault and can shut down operation of the system. After pressurizing control chamber 10, variable size orifice valve 536 is closed and the measured pressure $P_{C1}$ in control chamber 110 is recorded. In substep 3 (612) the pressure $P_{R1}$ in reference chamber 532, as measured with pressure transducer 548 (which will be different from that in control chamber 110) is stored by processor 506.

Substep 4 (614) involves allowing for measurement gas exchange between control chamber 110 and reference chamber 532. The gas exchange is enabled by opening and, optionally, closing valve 540. In some embodiments, valve 540 may be opened for a sufficient period of time to equilibrate the pressures in reference chamber 532 and control chamber 110 to essentially the same value. For such embodiments, it should be appreciated that pressure transducer 122 in fluid communication with control chamber 110 is optional since the measurement gas pressures in control chamber 110 can be determined, for various steps of the method, with pressure transducers 548, 510, or 514. In substep 5 (616), after allowing gas exchange, pressure $P_{C2}$ and $P_{R2}$ in control chamber 110 and reference chamber 532 respectively are measured and stored by processor 506. The volume $V_C$ of the control chamber and, optionally, the volume $V_F$ of pump chamber 108 at this first condition can be calculated from the known volume $V_R$ of reference chamber 532 and the above-measured pressures utilizing the ideal gas equation of state and conservation of mass, as described previously, from equation 2 shown previously.

In order to detect the presence of any gas in pump chamber 108, in substep 7 (620), substeps 1–6 (608, 610, 612, 614, 616, 618) are repeated as described above except that in substep 2 (610) switch valve 530 is positioned to select negative pressure supply tank 512. In substep 8 (622) processor 506 determines an absolute value of the difference between volume measurements determined in substep 7 (620) (i.e. at the second condition) and substep 6 (618) above and, as shown in FIG. 9c, compares this difference to a predetermined permissible limit and creates an alarm condition and initiates an air purge from pump chamber 108, in a manner substantially similar to that previously described, if the value exceeds the limit. If the value does not exceed the predetermined limit, the system proceeds to deliver the liquid in pump chamber 108, as described in FIG. 9a, steps 5–7.

Referring again to FIG. 9a, in step 5 (624), liquid is delivered from pump chamber 108 by, optionally, opening valves 546 and 540 to vent control chamber 110, followed by closing valves 540 and 546, positioning switch valve 530 to select positive pressure tank 508, and opening outlet valve 120 on outlet line 118 of pump chamber 108 while opening and controlling the orifice size of variable size orifice valve 536 to yield a desired pressure in control chamber 110 for pumping the liquid from the pump chamber. In preferred embodiments, variable size orifice valve 536 is controlled by processor 506 to maintain the pumping pressure in control chamber 110 at a desired value during the pump chamber emptying stroke. In such embodiments, processor 506 preferably includes a controller, for example a PID closed loop control system, which allows the processor to selectively change the size of the orifice within the variable size orifice valve 536 based, at least in part, on a difference between a pressure measured within control chamber 110 by transducer 122, and a desired predetermined pumping pressure. As discussed above in the context of filling pump chamber 108, pumping system 500 also preferably includes a method for controlling variable size orifice valve 536 so that the system is able to determine when flexible membrane 112 has stopped moving into pump chamber 108 indicating that liquid flowing from pump chamber 108 has stopped. This end of stroke detection method is described in more detail below. After a desired quantity of fluid has been delivered from pump chamber 108 or after an end of stroke condition has been determined as discussed above, outlet valve 120 downstream of pump chamber 108 is closed and, optionally, variable size orifice valve 536 is closed in order to isolate the pump chamber and control chamber.

Step 6 (626) of the pump cycle involves repeating the volume calculation routine by re-performing substeps 1–6 (608, 610, 612, 614, 616, 618) shown in FIG. 9b to calculate a final volume $V_{F2}$ of pump chamber 108 after delivery of the liquid. Finally, in step 7 (628) the volume delivered by pump 104 during the pump cycle $\Delta V$ can be determined by taking a difference in the pump chamber or control chamber volume determined after filling pump chamber 108 (determined in step 4) and the volume determined after pumping the liquid from pump chamber 108 (determined in step 6). If desired, a new pump cycle can be initiated by repeating the steps outlined in FIG. 9a.

The flow rate of the liquid delivered from the pump chamber for each pump stroke will be a function of the force applied to the flexible membrane of the pump chamber during the filling steps and delivery steps discussed above, and a function of the upstream and downstream liquid pressures in fluid communication with the pump chamber inlet line and outlet line respectively during filling and delivery. Typically, the forces applied to the flexible membrane, for example due to the pressure of the measurement gas in the control chamber, during the filling and delivery steps are chosen to yield a desired liquid flow rate for a given pump stroke cycle. For applications where the pumping system is being utilized to pump a liquid to the body of a patient, the fill and delivery pressures are preferably chosen to be compatible with acceptable pressures for infusion of liquid to a patient. Typically, for delivery of liquids to the vasculature of a patient, the maximum measurement gas pressure in the pumping system will not exceed about 8 psig and the minimum measurement gas pressure in the pumping system will not exceed about −8 psig.

When liquid delivery involves performing a multiple number of pump stroke cycles, as described above, over a period of time, in addition to determining a liquid flow rate for a given stroke, preferred pumping systems will include a processor that also is configured to determine an average pump flow rate over the entire period of operation. An average pump flow rate or average liquid flow rate is defined as the volume of liquid dispensed by the pump during multiple pump stroke cycles divided by the total time elapsed during the cycles. For applications involving multiple pump stroke cycles, in addition to controlling liquid flow rate via selection and control of the force applied to the pump chamber membrane, the system can also control the average liquid flow rate by selectively varying the length of a dwell period that can be inserted between individual pump stroke cycles prior to filling and/or delivering liquids from the pump chamber. The pumping systems according to the invention can also be configured to deliver a desired total liquid volume during operation, as well as to deliver a desired liquid flow rate as described above.

The predetermined limit to which the differences in measured volumes, or measured parameters related to volumes, of the pump chamber are compared for determining when the amount of gas in the pump chamber has exceeded an acceptable value can be determined in a variety of ways. The predetermined value may be chosen, for example, to be reflect the difference in volumes determined for an amount of gas present in the pump chamber that is equal to or somewhat less than the volume of the dead space in the pump chamber created by spacers, discussed above, therein. For applications where preventing air from being pumped from the pump chamber is critical, for example, when pumping liquid to the body of a patient, the predetermined threshold limit may be chosen to be less than that discussed above for safety reasons. In some embodiments, a predetermined limit can be determined by injecting a maximum permissible quantity of gas into the pump chamber, the remainder of which is filled with a liquid, and determining with the pumping system the difference in measured volume of the pump chamber at a first condition of applied force/pressures to the flexible membrane and a second condition of applied force/pressures to the flexible membrane, as described in detail in the above embodiments.

As discussed above in the context of FIGS. 8 and 9, a preferred pump drive system according to the invention includes a variable size orifice valve which can be controlled by the processor of the system in order to more precisely control the pressure of measurement gas applied to the control chamber during filling and dispensing of liquid from the pump chamber.

As discussed above, for such embodiments preferred systems will also include an end of stroke detection procedure to determine when liquid has stopped flowing into the pump chamber and when liquid has stopped flowing out of the pump chamber during filling and delivery strokes respectively. This end of stroke detection methodology is described in detail in commonly owned copending application Ser. No. 09/108,528, which is hereby incorporated by reference in its entirety. Briefly, in preferred embodiments, pump drive system 502 of FIG. 8 continuously monitors and controls the pressure of measurement gas in control chamber 110 during filling and dispensing of liquid from pump chamber 108. The system can detect the end of stroke as follows. During the filling or delivery step, processor 506 controls variable size orifice valve 536 so that the pressure of measurement gas in control chamber 110 has an average value essentially equal to the desired delivery or fill pressure and, in addition, includes a cyclically varying, low-amplitude variation in the pressure that is superimposed thereupon. For example, for a fill or delivery pressure in the range of a few psig, the variable component superimposed can have an amplitude that differs from the average target pressure by, for example, +/- about 0.05 psig, varying at a frequency of, for example, about 1 Hz. While the pump chamber 108 is filling or emptying, flexible membrane 112 will be in motion, and the system will detect the cyclical variations in pressure discussed above. However, at the end of a stroke, when the membrane is essentially no longer free to move in at least one direction and when liquid flow into or out of the pump chamber has essentially stopped, the pressure in control chamber 110 will no longer be able to be cyclically varied as described above. The system can detect this condition by continuously monitoring the pressure signal, for example, from transducer 122 on control chamber 110, differentiating the pressure signal with respect to time, taking an absolute value of the differentiated signal, and comparing the absolute value of the differentiated pressure signal to a minimum threshold value. At the end of the stroke, when the pressure in control chamber 110 is no longer cyclically varying, a derivative of the pressure with respect to time will approach zero and, therefore, by comparing the time derivative to a minimum threshold value, the system can determine when flexible membrane 112 has reached the end of its stroke, and can then discontinue filling or dispensing. In preferred embodiments, before comparing to the threshold value, the absolute value of the derivative of the pressure signal with respect to time is first subjected to a low pass filter in order to smooth the signal and derive a more stable value therefore.

Preferred pumping systems according to the invention are also able to detect a line blockage or occlusion in the inlet or outlet line of pump chamber 108 during operation, and are able to create an alarm condition and, in some embodiments, shut down the pumping cycle, when such blockage or occlusion is detected. Such a no-flow condition is detected by the system by comparing the volume of liquid delivered during the pump delivery stroke and the volume of liquid filling the pump chamber during the pump chamber filling stroke and comparing the volume, determined as described above, to the known minimum and maximum volumes for the pump chamber respectively. The system can then determine if the volume of liquid delivered by the pump chamber or the volume of liquid entering the pump chamber differs significantly from the volumes expected for a full stroke. If so, the system can create an alarm condition indicating a no/low flow condition or occlusion in the line exists. The no/low flow condition threshold value can be set based on the needs of the various applications of the inventive pumping systems and can be, in some embodiments, about one half of the maximum stroke volume of the pump chamber.

Certain embodiments provide an alternative way of operating a pump chamber for delivering a liquid therefrom, which is useful for generally, and especially useful when delivering very small quantities of liquid, liquid at very low average flow rates, and where precise measurement is needed. The basic steps of an example embodiment of this method include filling the pump chamber with a liquid, isolating the pump chamber, applying a force to the flexible membrane or moveable surface of the pump chamber, and regulating the flow of liquid from the pump chamber while maintaining the force on the membrane or surface. For example, in the context of pumping system 500 shown in FIG. 8, the method may involve first filling pump chamber 108 with a liquid as described previously with respect to FIG. 9, closing inlet valve 116 and taking an initial volume measurement of the pump chamber, placing control chamber 110 in fluid communication with the positive pressure tank 508 and controlling the pressure in control chamber 110 at a desired value utilizing variable size orifice valve 536, and then selectively actuating outlet valve 120 on the outlet line 118 of the pump chamber 108 to open and close the valve for predetermined time periods at predetermined intervals while maintaining the desired delivery pressure in control chamber 110. Volume measurements of pump chamber 108 can be performed either after each pulse (opening and subsequent closing) of outlet valve 120, or, alternatively, can be performed after a series of pulses of the outlet valve over a measured cumulative time interval. In this fashion, the volume delivered per pulse or the average liquid flow rate over a series of pulses can be determined, and the system can be configured to adjust the length of the time periods during which outlet valve 120 is opened and to adjust the time intervals between the pulsed openings of outlet valve 120 in order to achieve a desired predetermined average liquid flow rate. While the pulsed delivery mode of delivering a liquid from a pump chamber has been described in the context of FIG. 8, any of the other systems previously described (and other systems, as well) can also be used to perform a pulsed delivery of liquid from a pump chamber.

For certain embodiments of pumping systems, it is preferred that the systems be comprised of two separable components, one component being reusable and including the pump drive system, and the other component being removable from the reusable component. Such systems may be particularly useful for medical applications for pumping fluids to and/or from the body of a patient. In many embodiments, the reusable component may be disposable and designed for a single use.

The removable/disposable portion of the system may include the pump chamber and the pump chamber inlet and outlet lines, including the valves therein, and the other components which are in contact with the liquid being pumped with the pumping system. The removable/disposable component of such a system is referred to herein as the "pumping cartridge," which pumping cartridge can be configured and designed with a plurality of pump chambers, flow paths, valves, etc., specifically designed for a particular application. An exemplary pumping cartridge for use in one particular medical application is described in more detail below.

For example, considering the example pumping systems previously discussed, pumping system 100 shown in FIG. 1 may comprise a reusable pumping system component 230 coupled to a disposable pumping cartridge 231, including the disposable pump chamber 108, inlet line 114, inlet valve 116, outlet line 118, and outlet valve 120. For pumping system 300 shown previously in FIG. 5, the reusable component may comprise reusable system 302, which would be coupled in operative association with a pumping cartridge 305, when the pumping system is in operation. Similarly, pumping system 400 of FIG. 7 would comprise a reusable component 402 coupled to pumping cartridge 403, and pumping system 500 shown in FIG. 8 would include reusable component 502 coupled to a pumping cartridge 503.

For embodiments involving removable/disposable pumping cartridges and reusable pump drive systems, the pumping cartridge and the reusable component are constructed and arranged to be couplable to each other. "Constructed and arranged to be couplable" as used herein indicates that the separable components are shaped and sized to be attachable to and/or mateable with each other so that the two components can be joined together in an operative association. Those of ordinary skill in the art would understand and envision a variety of ways to construct and arrange pumping cartridges and components of reusable systems to be couplable in operative association. A variety of such systems which may be employed in the present invention have been described previously in commonly owned U.S. Pat. Nos. 4,808,161, 4,976,162, 5,088,515, and 5,178,182.

Typically, the pumping cartridge and reusable component will be coupled together with an interface therebetween, where the reusable component adjacent to the interface will have a series of depressions formed in a surface of the interface, which depressions are sized and positioned to mate with similar depressions in the pumping cartridge, when the pumping cartridge and the reusable component are coupled together, so that upon coupling, the depressions in the pumping cartridge and the reusable components together form the various chambers utilized by the pumping system. Also, when coupled together, the pumping cartridge and the reusable component preferably interact at an interface therebetween such that the interface creates a fluid impermeable/fluid-tight seal between the components, so that the measurement fluid contained by the reusable component and the liquid present in the pumping cartridge are not in fluid communication with each other during operation of the system. Those of ordinary skill in the art would readily envision a variety of means and mechanisms for coupling together the pumping cartridges and reusable components to achieve the above requirements. For example, the components may be held together in operative association by clips, bolts, screws, clamps, other fasteners, etc., or the reusable component may include slots, channels, doors, or other components as part of a housing for holding the pumping cartridge in operative association with the reusable component. Such techniques for coupling together disposable/reusable pumping cartridges and reusable pump drive systems are well known in the art, and any such systems are potentially useful in the context of the present invention.

Figure 10:
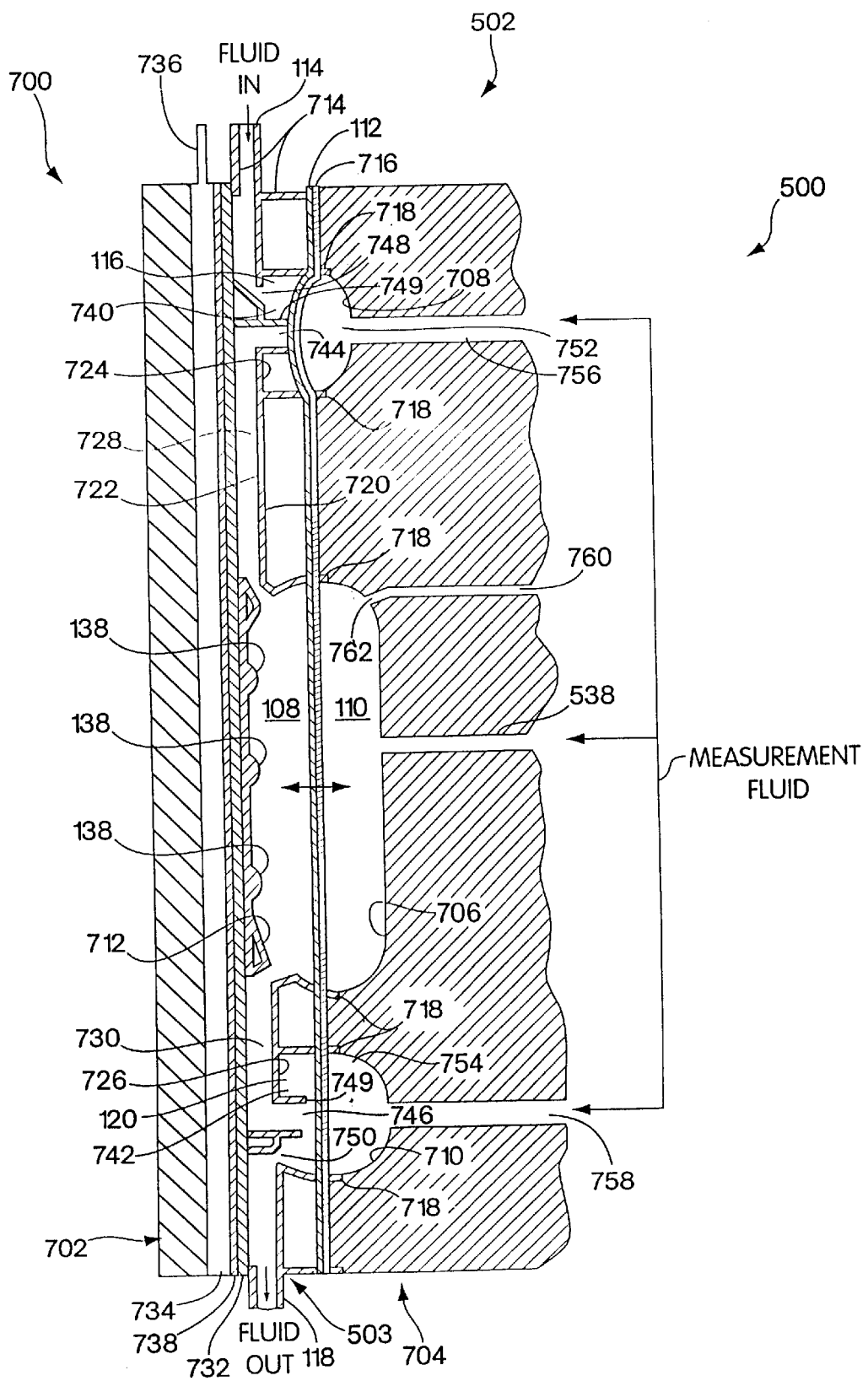
FIG. 10 is a partially-cutaway cross-sectional illustration of a removable pumping cartridge and pump housing component according to one embodiment of the invention.

FIG. 10 shows a preferred embodiment of the interface between pumping cartridge 503 and reusable pump drive system 502 of pumping system 500 shown previously in FIG. 8. FIG. 10 is a cut-a-way view showing only the portion of reusable component 502 which mates with and is in contact with pumping cartridge 503 when the components are coupled together in operative association. Such portion of the reusable component will hereinafter be referred to as the "pump housing component." Also shown in FIG. 10 is a preferred arrangement for providing valves in fluid communication with the liquid flow paths of the pumping cartridge, which valves are described in more detail below.

Pump housing component 700 includes a door 702 and a mating block 704 the surface of which forms an interface when pumping cartridge 503 is coupled to pump housing component 700. Mating block 704 has a generally planar surface in contact with the pumping cartridge having a variety of depressions 706, 708, 710 therein which mate with complementary depressions contained within pumping cartridge 503 for forming various chambers of the pumping system when the components are coupled together. For example, depression 706 in mating block 704 is coupled to depression 712 in pumping cartridge 503 thus forming a pump chamber 108 in pumping cartridge 503 and an adjacent control chamber 110 in mating block 704, when the components are coupled together.

As will be described in more detail below, pumping cartridge 503 comprises a substantially rigid component 714 covered, on at least one side thereof, by a flexible membrane, which in preferred embodiments is an elastic membrane. In a preferred embodiment shown, mating block 704 is also covered by a flexible membrane 716 which is in contact with flexible membrane 112 covering pumping cartridge 503, when the components are coupled together. Flexible membrane 716 is an optional component which provides an additional layer of safeguarding against potential leakage of fluids between pumping cartridge 503 and the reusable component thus preventing contamination of the reusable component by the liquids in the pumping cartridge.

Upon coupling, a fluid-tight seal should be made between the flexible membranes and the surfaces of mating block 704 and pumping cartridge rigid component 714 forming the various chambers. In order to obtain such a seal, there should be some degree of compression between pumping cartridge 503 and mating block 704 when the components are coupled together. In addition, seals 718 may be provided around the periphery of the depression within mating block 704, which seals are positioned adjacent to the periphery of complementary depressions in pumping cartridge 503 in order to create additional compression of the flexible membranes for forming a leak-tight seal. Alternatively, such seals could be provided around the perimeter of the depressions in pumping cartridge 503 in addition to, or instead of, mating block 704. Such seals may be provided by a variety of materials, as apparent to those of ordinary skill in the art, for example, properly sized rubber or elastomer O-rings can be used which fit into complementary grooves within mating block 704 or, alternatively, are affixed to the mating block by adhesives, etc.

As discussed above, pumping cartridge 503, in the embodiment shown, includes a substantially rigid component 714 that is preferably constructed of a substantially rigid medical grade material, such as rigid plastic or metal. In preferred embodiments, substantially rigid component 714 is constructed from a biocompatible medical grade polyacrylate plastic. As will be described in more detail below, substantially rigid component 714 is molded into a generally planar shape having a variety of depressions and grooves or channels therein forming, when coupled to the reusable component, the various chambers and flow paths provided by the pumping cartridge.

In some embodiments, the substantially rigid component of the pumping cartridge can include a first side, which mates with the mating block, which first side contains various depressions and channels therein for forming flow paths and chambers within the pumping cartridge upon coupling to the reusable component. This first side of such pumping cartridges is covered with a flexible, an preferably elastic membrane, which can be bonded to the first side of the substantially rigid component at the periphery thereof and/or at other locations on the first side. Alternatively, instead of being a single continuous sheet, the flexible membrane may comprise a plurality of individual membranes which are bonded to the substantially rigid component only in regions comprising chambers, or other components, in operative association with the reusable component.

FIG. 10 shows such an embodiment of a pumping cartridge 503 which has a first side 720, facing mating block 704, and a second side 722, facing door 702 of pump housing component 700, each of which sides is covered by a flexible membrane. First side 720 of pumping cartridge 503, as shown, includes depressions 712, 724, and 726 and is covered by flexible membrane 112. The second side 722 of pump cartridge 503 includes a variety of channels 728, 730 formed therein, which channels are covered by flexible membrane 732, which is disposed on the second side 722 of pump cartridge 503, the combination of which channels and flexible membrane provide fluid-tight liquid flow paths within pumping cartridge 503, upon coupling to the reusable component.

The flexible membranes for use in pumping cartridge 503 and, in some embodiments, mating block 704, can be comprised of a variety of flexible materials known in the art, such as flexible plastics, rubber, etc. Preferably, the material comprising the flexible membranes used for the pumping cartridge is an elastic material that is biocompatible and designed for medical use, when used for applications where the pumping cartridge is used for pumping liquid to and from the body of a patient. The material comprising the flexible membranes should also be selected based on its ability to form a fluid-tight seal with the substantially rigid component 714 of pumping cartridge 503 and with mating block 704 of the reusable component. In a preferred embodiment, where rigid component 714 of pumping cartridge 503 is formed of a clear acrylic plastic, elastic membrane 112 is comprised of polyvinyl chloride sheeting, which is about 0.014 in thick and which is hermetically sealed to the first side 720 of rigid component 714 of pumping cartridge 503. Since the elasticity of membrane 712 disposed on the second side 722 of pumping cartridge 503 does not substantially contribute to its performance, it is not necessarily preferred to use an elastic material for membrane 712. However, for convenience and ease of fabrication, membrane 712 can be comprised of the same material as membrane 112, and can be hermetically sealed the second side 722 of rigid component 714 of pumping cartridge 503 in a similar fashion as membrane 112.

In the embodiment illustrated, door 702 is hinged to the body of the reusable component and can be opened or closed by an operator of the system, either manually, or in some embodiments, under computer control of the processor controlling the system, so that pumping cartridge 503 can be properly inserted and mated with mating block 704. Preferably, pumping cartridge 503, mating block 704, and door 702 are shaped and configured so that pumping cartridge 503 can only mate with the reusable component in the proper orientation for operative association. In preferred embodiments, door 702 latches to the reusable component when closed. In some embodiments, the pumping system may include detectors and circuitry for determining the position of the door and is configured to allow operation of the system only when pumping cartridge 503 has been properly installed and door 702 has been properly closed. Also, in preferred embodiments, the pumping system is configured to prevent the door from being opened during operation of the system, so that the fluid-tight seal that is formed between pumping cartridge 503 and the reusable system is not compromised while the system is in operation. Door 702 also, in preferred embodiments, includes an inflatable piston bladder 734 having an inlet line 736 which is in fluid communication with a fluid supply of the pumping system when the system is in operation. Also, in preferred embodiments, adjacent to piston bladder 734 and pumping cartridge 503 is an essentially planar piston surface 738. After inserting pumping cartridge 503 and closing door 702, but before operating pumping cartridge 503, the system supplies pressurized fluid to piston bladder 734 to create a compressive force against pumping cartridge 503 so as to create fluid-tight seals within the system, as described previously.

As discussed above, pumping cartridge 503 and reusable component 502, as shown in FIG. 10, together provide a unique means of operating the valves within pumping cartridge 503. Inlet valve 116 and outlet valve 120 include valving chambers 740 and 742 which are formed from the combination of depressions 724 and 726 within rigid component 714 and flexible membrane 112. Each valving chamber includes at least one occludable port 744, 746 and at least one other port 748, 750. In the embodiment shown, ports 748, 750 are not occludable by flexible membrane 112. In other embodiments, ports 748 and 750 may be occludable and similar in construction to occludable ports 744 and 746. As shown, ports 744 and 750 comprise holes within rigid component 714 of pumping cartridge 503 allowing fluid communication between liquid flow paths 114 and 118 present on the second side 722 of pumping cartridge 503 and valving chambers 740 and 742 located on the first side 720 of pumping cartridge 503. Occludable ports 744 and 746 also provide fluid communication between the valving chambers and liquid flow paths within the pumping cartridge. Occludable ports 744 and 746 are constructed so that holes through which a liquid flows are located on members 749 that protrude from the base of the depression forming the valving chambers. In preferred embodiments, protruding members 749 have a truncated conical shape, wherein ports 744 and 746 comprise holes in the truncated apex of the conical protruding members.

Mated to valving chambers 740 and 742, when the pumping cartridge is in operative association with the reusable component, are valve actuating chambers 752 and 754 formed from depressions 708 and 710 within mating block 704. In order to close the valves to restrict or block flow therethrough, pumping system 500 includes valve actuators (provided in this embodiment by the valve actuating chambers as shown) configured to selectively and controllably apply a force to flexible membrane 112 tending to force the flexible membrane against an adjacent occludable port, thus occluding the port. Inlet valve 116 is shown in such a closed configuration. To open a valve, the pumping system can release the positive force applied to flexible membrane 112 and, in some embodiments, can apply a negative force to flexible membrane 112 tending to move the membrane into the valve actuating chamber. Outlet valve 120 is shown in FIG. 10 in such an open configuration. Pumping system 500 is configured as shown to open and close the valves within pumping cartridge 503 by selectively applying a measurement gas to the valve actuating chambers at a pressure sufficient to occlude the occludable ports contained within the valving chambers. Such pressure will exceed the pressure of any liquid contained in the valving chamber.

Gas inlet lines 756 and 758 supplying valve actuating chambers 752 and 754 are connected so that they are able to be placed in fluid communication with a pressurized measurement gas supply source(s) contained in pumping system 500. It should be understood that in other embodiments not shown, pumping system 500 may include valve actuators using alternative means as a force applicator for applying a force to flexible membrane 112 in order to occlude occludable ports 744 and 746. In alternative embodiments, the system may include a valve actuator that includes a force applicator comprising, for example, a mechanically actuated piston, rod, surface, etc., or some other force applicator using an electrical or magnetic component, disposed adjacent to the flexible membrane. In preferred embodiments, as shown, the system comprises a valve actuator comprising a valve actuating chamber, where the force applicator for applying a force to the flexible membrane comprises a pressurized gas or other fluid.

As with other particular features described above, this valve and mechanism for operating the valve is particularly advantageous. Use of such valves are not, however, required in all embodiments of the present invention and, in the context of a system design, any other valve and valve actuator may be used.

Also shown in FIG. 10 is a preferred mechanism for providing a pressure measuring component for determining the pressure in control chamber 110, which may be used in some (but not all) embodiments of the present invention. Pumping system 500 as shown in FIG. 10 is configured so that pressure transducers are resident on a circuit board contained within processor 506 (not shown in FIG. 10), which transducers are connected in fluid communication with various chambers and components in the system via tubing or channels. For example, pressure transducer 122 (not shown) for measuring the pressure in control chamber 110 is connected in fluid communication with control chamber 110 via line 760 and port 762 in fluid communication with control chamber 110.

Preferably, after mating pumping cartridge 503 to the reusable component and before commencement of operation, pumping system 500 is configured to perform a variety of integrity tests on pumping cartridge 503 to assure the proper operation of the pumping system. In such embodiments, pumping system 500 includes an inlet and outlet tube occluder (not shown) for blocking the flow of fluid to and from pumping cartridge 503 and for isolating the chambers and flow paths of pumping cartridge 503. After coupling pumping cartridge 503 to the reusable component but before priming pumping cartridge 503 with liquid, a dry pumping cartridge integrity test can be performed. The test involves opening the inlet and outlet line occluding means so that pumping cartridge 503 is not isolated from the surroundings and supplying all of the control chambers and valve actuating chambers in the system with a measurement gas at a predetermined positive or negative pressure. The system then continuously monitors the measurement gas pressure within the various chambers of the reusable component over a predetermined period of time. If the change in pressure exceeds a maximum allowable predetermined limit, the system will indicate a fault condition and terminate operation. This dry pumping cartridge integrity test is useful for detecting holes or other leaks within flexible membrane 112. The dry pumping cartridge integrity test integrity test briefly described above is discussed in more detail in commonly owned copending application Ser. No. 09/193,337 incorporated by reference herein in its entirety.

After performing the dry pumping cartridge integrity test above, but before operation, a wet pumping cartridge integrity test can also be performed. The test involves first priming all of the chambers and flow paths of pumping cartridge 503 with liquid and then performing the following two tests. First, the integrity of the valves within the pumping cartridge is tested by applying positive pressure to valve actuating chambers 752 and 754 to close valves 116 and 120 within the pumping cartridge, and then applying the maximum system measurement gas pressure to the control chamber 110 coupled to the pump chamber 108. The system is configured to measure the volume of the pump chamber 108 within the pumping cartridge, as described previously, before the application of pressure, and again after the pressure has been applied to the pump chamber for a predetermined period of time. The system then determines the difference between the measured volumes and creates an alarm condition if the difference exceeds an acceptable predetermined limit. The second test involves determining the fluid tightness of the various fluid flow paths in chambers within pumping cartridge 503. This test is designed to prevent the system from operating when a cartridge has been manufactured so that there may be leakage between flow paths and undesirable mixing of liquids within the pumping cartridge. The test is performed in a similar fashion as that described immediately above except that the valves within pumping cartridge 503 are maintained in an open configuration with the inlet and outlet line occlusion means being actuated by the system to isolate the pumping cartridge from its surroundings. As before, a maximum measurement gas pressure is applied to the control chamber of the reusable component, and the volume contained in the pump chamber is determined before and after application of pressure. Again, the system is configured to create an alarm condition and discontinue operation if the differences in measured volume exceed an allowable predetermined limit. It should be understood that while the various integrity tests and preferred modes of operating a pumping cartridge have been described in the context of system 500 and pumping cartridge 503 illustrated in FIG. 10, the methods and tests can also be applied and employed for other configurations of the pumping cartridge and reusable system.

Figure 11A:
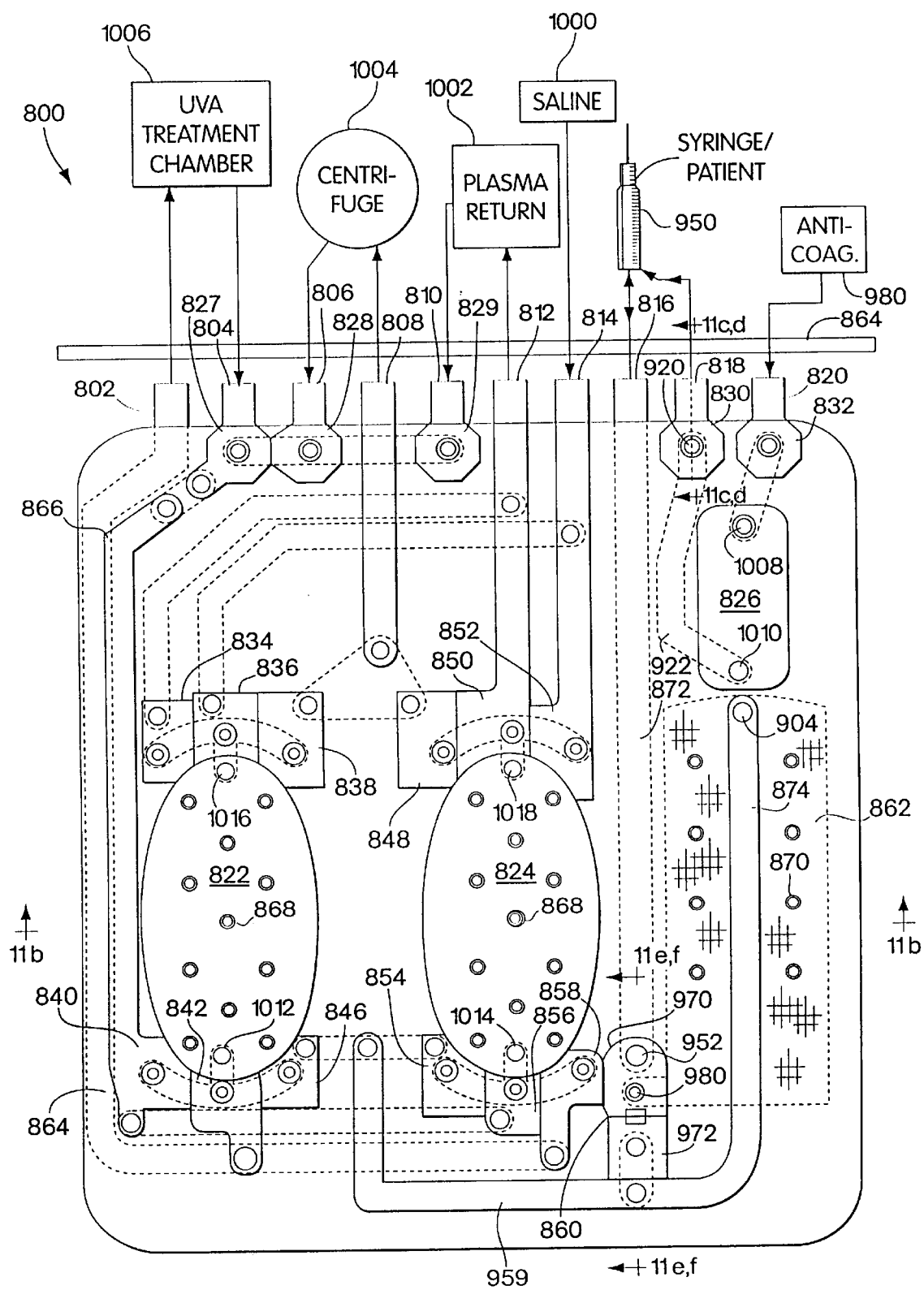
FIG. 11a is a schematic illustration of a pumping cartridge according to one embodiment of the invention.

FIGS. 11*a*–11*f* show various views and features of one particular embodiment of a multi-functional pumping cartridge according to the invention which includes a plurality of pump chambers, valving chambers, and fluid flow paths therein. The pumping cartridge shown in FIGS. 11*a*–11*f* is similar in construction to pumping cartridge 503 shown in FIG. 10, in that the pumping cartridge includes a substantially rigid component with various depressions and channels/grooves therein covered on each side with a flexible membrane that is hermetically sealed thereto. FIG. 11*a* is an en face view of the first side of pumping cartridge 800, which first side is coupled to and in contact with an interface of a mating block on a complementary reusable system when the pumping cartridge is in operation. As discussed below, except for the particular arrangement and number of components, pumping cartridge 800 is similar in overall design to that described previously in the context pumping cartridge 503 of FIG. 10.

Pumping cartridge 800 includes a plurality of inlet and outlet lines 802, 804, 806, 808, 810, 812, 814, 816, 818, and 820 for connecting the various flow paths of the pumping cartridge in fluid communication with lines external to the pumping cartridge. In one preferred embodiment, pumping cartridge 800 is utilized for pumping blood from the body of a patient, treating the blood, or components thereof, and returning treated blood and other fluids to the body of the patient. For such embodiments, pumping cartridge 800 is preferably disposable and designed for a single use, and is also preferably biocompatible and sterilizable so that it may be provided to the user as part of a sterile, single-use package.

As shown in FIG. 11*a*, pumping cartridge 800 includes two large pump chambers 822 and 824 and a third smaller pump chamber 826. Pumping cartridge 800 also includes a plurality of valving chambers 827, 828, 829, 830, 832, 834, 836, 838, 840, 842, 846, 848, 850, 852, 854, 856, and 858 for controlling and directing the flow of liquid through the various liquid flow paths and pump chambers provided within pumping cartridge 800. The construction of each of the pump chambers and valving chambers above is similar to that shown previously for pumping cartridge 503 shown in FIG. 10. Pumping cartridge 800 also includes the novel inclusion of a bypass valve provided by a bypass valving chamber 860 and an integrated filter element 862, the function and structure of which components are explained in more detail below.

In operation, pumping cartridge 800 is coupled in operative association with a complimentary mating block of a reusable component having depressions and pneumatic (in appropriate embodiments) connections therein for actuating the various pump chambers and valving chambers of the pumping cartridge in a similar fashion as that previously described. The reusable component also preferably includes an occluder 864 included therein, disposed adjacent to tubing in fluid communication with the various inlet/outlet ports of the pumping cartridge, for occluding the various inlet and outlet lines in fluid communication with the pumping cartridge when performing various integrity tests as described previously and/or for other purposes where it is desirable to fluidically isolate the pumping cartridge. In preferred embodiments, the occluder is constructed as described below and is configured to occlude the tubing unless a force is applied to the occluder, for example by supplying a pressurized fluid to a bladder tending to move the occluder to unocclude the various tubing. In such embodiments, in a fail safe condition (e.g. during a power failure) the occluder will be configured to occlude the tubing, thus preventing undesirable liquid flow to and/or from a source or destination (especially when such source or destination is the body of a patient.

As described below, the reusable system that is constructed and arranged for operative association with pumping cartridge 800 will also include various processors (or a single processor configured to perform multiple functions, or other suitable hardware or software mechanisms) to selectively control and operate the various components of pumping cartridge 800 for performing various user designated pumping applications. It will be understood by those of ordinary skill in the art that pumping cartridge 800 can be used for an extremely wide variety of potential pumping and fluid metering applications depending on the manner in which the various components contained therein are operated and controlled. Each of such uses and applications are deemed to be within the scope of the present invention.

The flow paths within pumping cartridge 800 which are comprised of channels formed on the first side of the pumping cartridge (the side facing the viewer), for example flow path 866, are shown as solid lines. Flow paths that are formed from channels disposed on the second (opposite) side of pumping cartridge 800, for example flow path 872, are shown in FIG. 11*a* by dashed lines. As can be seen in FIG. 1*a*, in the embodiment shown, filter element 862 is also disposed on the second side of pumping cartridge 800. As will be described in more detail below, a preferred function of filter element 862 is to filter fluids being pumped from pumping cartridge 800 to the body of a patient to remove any blood clots or aggregated material therefrom.

Figure 11B:
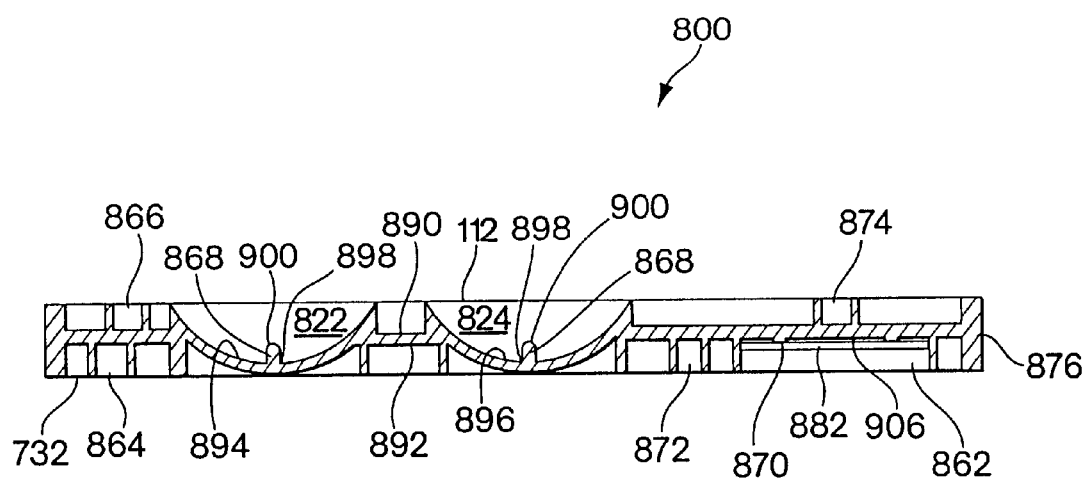

The structure of pumping cartridge 800 can be seen more clearly from the cross-sectional view of FIG. 11*b*. Pumping cartridge 800 includes a substantially rigid component 876 having a series of depressions and channels therein forming the various chambers and flow paths of the pumping cartridge. Pumping cartridge 800 has a first side 890, which is disposed against a mating block of the reusable component in operation, and a second side 892, which is disposed against the door of the pump housing component when in operation. First side 890 is covered by flexible membrane 112 hermetically sealed around the periphery of rigid component 876. Second side 892 is similarly covered by flexible membrane 732. Clearly visible are liquid flow paths 866 and 874, both of which are disposed on first side 890 of pumping cartridge 800 and liquid flow paths 864 and 872 disposed on second side 892 of pumping cartridge 800. Pump chambers 822 and 824 are formed from curved depressions 894 and 896 in first side 890 of rigid component 876. Clearly visible are spacers 868 which comprise elongated protuberances having bases 898 attached within the pump chambers to rigid component 876 and ends 900 extending into pump chambers 822 and 824 toward flexible membrane 112. As previously described, these spacers prevent contact of flexible membrane 112 with the base of depressions 894 and 896 in rigid component 876 during pumping and provide a dead space which inhibits pumping of gas from the pump chambers during operation. In this embodiment, the spacers are small, evenly spaced bumps located on a wall of the pump chamber. The size, shape and positions of the spacers can be changed and still serve the purpose of reducing risk of passing gas through the pump chamber.

Referring to FIG. 11b, filter element 862 includes a filter 882 disposed on second side 892 of rigid component 876. Filter 882 is preferably substantially planar and is disposed adjacent to second side 892, spaced apart therefrom by spacers 870, so that the filter and the region of second side 892 to which it is attached are essentially coplanar. During operation of the pumping cartridge for pumping liquid to a patient, fluid to be pumped to the patient is directed along flow path 874 to the inlet port 904 of filter element 862 (see FIG. 11a) into space 906 separating filter 882 from second side 892, through filter 882, and out of filter element 862 through occludable port 980 (see FIG. 11a). In order to prevent fluid from bypassing filter 882 within filter element 862, filter element 862 should be sealed to second side 892 of rigid component 876 along its periphery in a fluid-tight fashion. Also, for embodiments where filter element 862 is functioning as a blood clot filter, filter 882 preferably has pores therein which are larger in diameter than the diameter of a typical human blood cell, but which are small enough to remove a substantial fraction of clotted blood or aggregated blood cells that may be present in a liquid pumped therethrough. In preferred embodiments, filter 882 comprises a polyester screen, in one embodiment having pore sizes of about 200 $\mu$m with about a 43% open area.

Figure 11C:
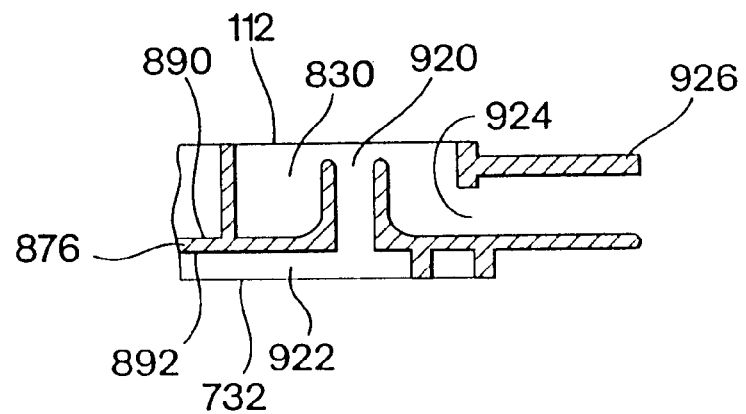
Figure 11D:
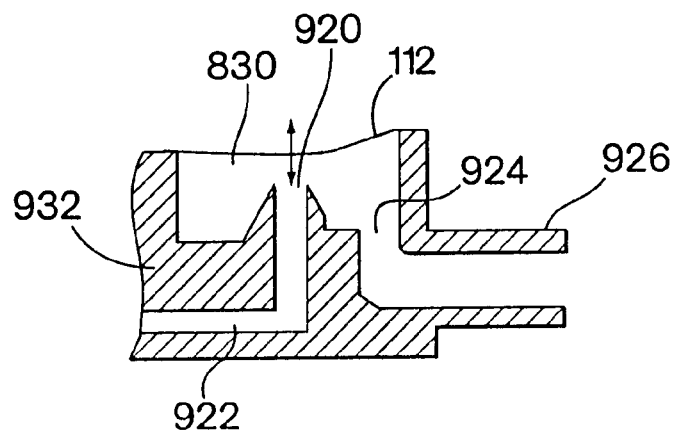
FIG. 11d is a partially-cutaway cross-sectional illustration of the valve of FIG. 11c, according to an alternative embodiment of the invention.

FIG. 11c is a cross-sectional view of outlet valving chamber 830. Outlet valve 830 has a structure which is representative of the valving chambers provided in pumping cartridge 800. The structure of valving chamber 830 is substantially similar to the structure of the valving chambers in pumping cartridge 503 shown in FIG. 10 previously. Valving chamber 830 is formed in first side 890 of rigid component 876 of pumping cartridge 800 and includes one occludable port 920 in fluid communication with liquid flow path 922 on second side 892 of the pumping cartridge and a non-occludable port 924 in fluid communication with outlet line 926. FIG. 11d shows an essentially equivalent valving chamber for an alternative embodiment of a pumping cartridge having an essentially rigid component 932 covered on only a single side by a flexible membrane. Analogous components of the alternative valve embodiment of FIG. 11d are given the same figure labels as in FIG. 11c for comparison.

Referring again to FIG. 11a, the function of bypass valving chamber 860 and filter element 862, as well as the flexibility of operation of pumping cartridge 800, will be explained in the context of a particular embodiment involving an application utilizing pumping cartridge 800 that includes removing blood from the body of a patient, pumping the blood to various selectable destinations with pumping cartridge 800, and returning treated blood or other fluids to the body of a patient. As will be described in detail below, it is desirable, in such an embodiment, to pump fluids which are being returned to the body of a patient through filter element 862 to remove any clots or aggregates therefrom, and to bypass filter element 862 when withdrawing blood from a patient with pumping cartridge 800. When in operation, pumping cartridge 800 is preferably coupled to a reusable component such that pumping cartridge 800 is oriented essentially vertically with the various inlet and outlet lines pointing up. As illustrated, inlet/outlet port 816 is in fluid communication with a syringe or shunt 950 inserted into the vasculature of a patient. Blood withdrawn from the patient and fluid returned to the patient flows through inlet/outlet 816 and along liquid flow path 872 within pumping cartridge 800. Liquid flow path 872 is in fluid communication with bypass valving chamber 860 via a first port 952. Also in the illustrated embodiment, inlet valve 832 of small pump chamber 826 is in fluid communication with a supply of anticoagulant 980, and outlet valve 830 of pump chamber 826 is in fluid communication with the syringe/shunt 950 inserted into the body of a patient. In this configuration, small pump chamber 826 can be utilized as an anticoagulant delivery pump for pumping an anticoagulant to an injection site of a patient in order to keep the injection site from blocking and in order to provide anticoagulant to blood removed from the patient.

As explained in greater detail below, the function of bypass valving chamber 860 is to selectively permit liquid flow along a first liquid flow path bypassing filter element 862, or alternatively, to block flow along the first fluid flow path and direct flow along a second liquid flow path, which second liquid flow path directs the liquid so that it flows through filter element 862. Also, as discussed below, valving chamber 860 also permits liquid flow along both liquid flow paths above to be simultaneously blocked if desired. For the present embodiment where blood is being removed from a patient and, subsequently, liquids are being returned to a patient, the first liquid flow path described above will be selected by the system, by utilizing bypass valving chamber 860, when removing blood from the patient, and the second liquid flow path described above will be selected by the system, utilizing bypass valving chamber 860, when liquids are being pumped from the pumping cartridge to the patient.

Bypass valving chamber 860 is comprised of two adjacent subchambers 970, 972 separated by a partition 974 therebetween, which has an aperture therethrough permitting unrestricted fluid communications between the two subchambers. "Subchamber(s)" as used herein refers to regions of a chamber within a pumping cartridge, which region includes an internal partition, that are adjacent and are separated one from the other by the internal partition, where the internal partition allows unrestricted fluid communication between the regions.

Figure 11E:
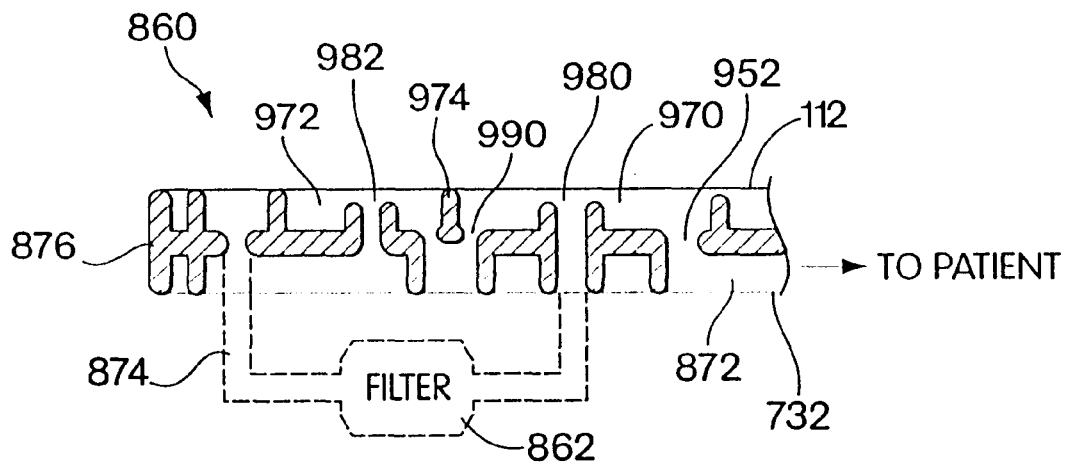

The structure of bypass valving chamber 860 is shown in greater detail in the cross-sectional view of FIG. 11e. Referring to FIG. 11e, partition 974 separates the bypass valving chamber into subchambers 970 and 972 and is in fluid-tight contact with flexible membrane 112 when the pumping cartridge is coupled to a reusable component. When coupled with a reusable component, subchamber 970 and subchamber 972 can each be coupled adjacent to and in operative association with a separate and independently controllable valve actuating chamber in the reusable component, which is each disposed adjacent to the subchamber. The valve actuating chambers can be independently operated to selectively occlude and open occludable port 980 in subchamber 970 and occludable port 982 in subchamber 972.

Also shown in FIG. 11e, for the purposes of illustrating the function of bypassing valving chamber 860, is a schematic representation of a second liquid flow path through the bypass 25 valving chamber where the liquid is forced through filter element 862. Referring to both FIGS. 11a and 11e together, consider a first step in a pumping method using the pumping cartridge during which blood is withdrawn from the patient by filling pump chamber 822 and/or 824. During this step, as discussed above, it is desirable to flow blood from the patient through bypass valving chamber 860 along a first liquid flow path which bypasses filter element 862. This can be accomplished by occluding occludable port 980 in subchamber 970 while leaving occludable port 982 in subchamber 972 non-occluded. In such a situation, blood will flow from the patient, along liquid flow path 872 into subchamber 970 through port 952, from subchamber 970 to subchamber 972 through opening 990 in partition 974, and will exit subchamber 972 through occludable port 982. For a situation where treated blood or another liquid such as plasma or saline is being pumped with pump chamber 822 and/or 824 through line 959 to bypass valving chamber 860 to be reinfused into a patient, as discussed above, it is desirable to operate the bypass valving chamber so that the liquid flows along the second liquid flow path, which passes the liquid through filter element 862 prior to returning it to the patient. In such a situation, the second liquid flow path can be selected by occluding occludable port 982 in subchamber 972 and leaving non-occluded occludable port 980 in subchamber 970. In which case fluid will flow along liquid flow path 959 and subsequently along liquid flow path 874 to the inlet port 904 of filter element 862. Liquid will not be able to enter subchamber 972 due to the occlusion of occludable port 982. The liquid, after entering filter element 862, will pass through filter 882 and exit filter element 862 by entering subchamber 970 through occludable port 980. The liquid will then exit subchamber 970 through port 952 and flow along liquid path 872 for return to the patient.

Figure 11F:
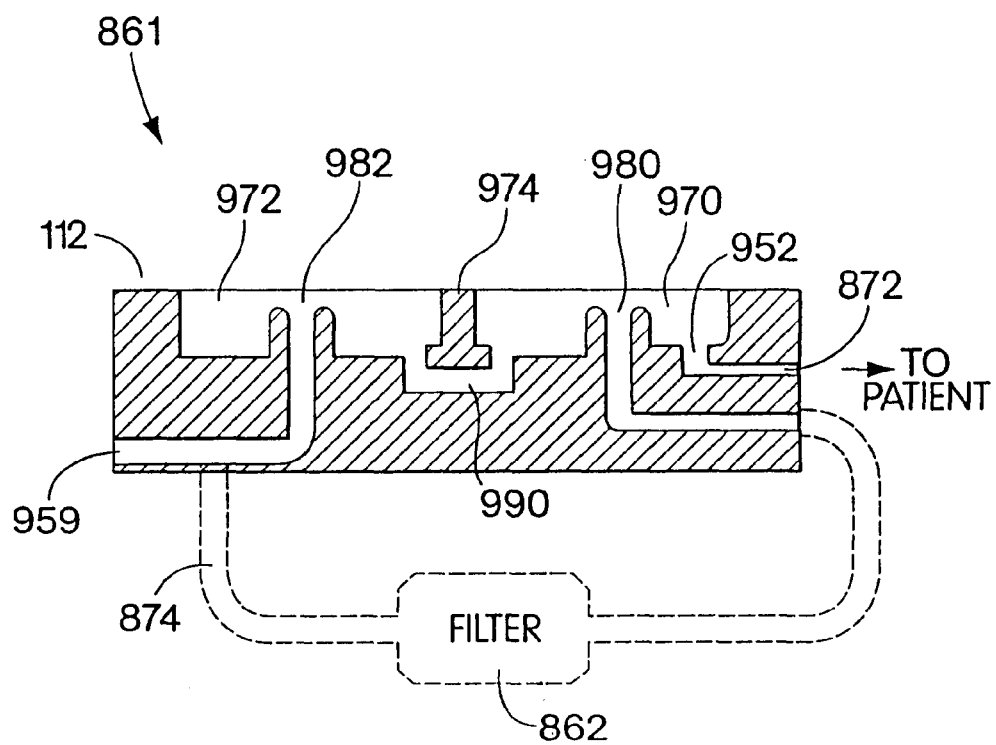
FIG. 11f is a partially-cutaway cross-sectional illustration of the bypass valving chamber of FIG. 11e, according to an alternative embodiment of the invention.

FIG. 11f shows an essentially equivalent bypass valving chamber 861 for an alternative embodiment of a pumping cartridge having an essentially rigid component 932 covered on only a single side by a flexible membrane. Analogous components of the alternative bypass valve embodiment of FIG. 11f are given the same figure labels as in FIG. 11e for comparison.

During other operations utilizing pumping cartridge 800, it may be desirable to operate bypass valving chamber in order to block liquid flow along both the first liquid flow path (bypassing the filter element) and along the second liquid flow path (wherein the liquid is passed through the filter element). Flow can be blocked along both the above-mentioned liquid flow paths utilizing bypass valving chamber 860 simply by occluding both occludable port 980 and 982 simultaneously.

It should be understood that while the operation of bypass valving chamber has been described in the context of pumping blood and liquids to and from a patient and for the purpose of selectively passing such liquids through a filter or bypassing the filter, the bypass valving chamber provided by the invention can be used for a wide variety of other purposes, wherein it is desirable to selectively choose liquid flow along a first and second liquid flow path. It should also be understood that while in the above-mentioned embodiment liquids flowing along a first and second liquid flow path through bypass valving chamber 860 flow through the chamber in a particular direction, in other embodiments, the direction of liquid flows along the first and second liquid flow path could be reversed or could be co-directional in either direction.

Referring again to FIG. 11a, a variety of exemplary sources and destinations in fluid communication with pumping cartridge 800 are illustrated in the exemplary embodiment shown, in addition to anticoagulant source 980 and syringe/port 950, pumping cartridge 800 is also connected to a source of saline 1000, a plasma storage container 1002, a centrifuge 1004 for separating blood cells from plasma and/or certain blood cells from each other, and a treatment chamber 1006 for performing a treatment on blood, plasma, or blood cells. By selectively operating the various pump chambers and valving chambers within the pumping cartridge, liquids can be pumped to and from various sources and destinations for a variety of purposes and treatments as would be apparent to those of ordinary skill in the art.

In one particular embodiment, pumping cartridge is utilized as part of a system designed for use in photopheresis treatment to the blood components of a patient as part of a therapy for the treatment of various blood disorders and treatments such as in the treatment of HIV infection, to prevent the rejection of transplants, or for treatment of various autoimmune disorders, for example scleroderma. In this embodiment, the patient is first given a dose of the drug psoralen about 30 min. prior to blood treatment. The psoralen molecules attach to specific undesirable blood components. In this embodiment, treatment chamber 1006 is configured to expose the fractionated blood components of a patient to ultraviolet A (UVA) light to activate the psoralen molecules which in turn modify the blood components to which they are bound so that upon reinfusion into the patient, the modified blood components are either recognized by the patient's immune system and eliminated, or they are immobilized and prevented from harming the patient (for guidance in performing the UVA treatment and configuring a UVA treatment chamber reference is made to U.S. Pat. No. 5,147,289 to Edelson, incorporated herein by reference in its entirety). Pumping cartridge 800, for this embodiment, can be operated to initially remove blood from the patient, pump the blood to centrifuge 1004 to fractionate the various components according to the needs of the particular treatment protocol, direct one or more blood components to treatment chamber 1006 for UVA activation and, if desired one or more other components back to the patient or to a storage container, such as plasma return 1002, and finally pump the UVA-treated blood components back to the patient, as well as, if desired or required, saline from saline container 1000 and/or any blood components contained in plasma return container 1002. It will be apparent to those of ordinary skill in the art that the above outlined protocol may be modified in a variety of ways and customized for specific procedures without departing from the scope of the invention.

In general, pump chambers 822, 824 and 826 of pumping cartridge 800 can be operated utilizing a reusable component including a pump drive system constructed according to any of the embodiments previously described for such systems. Pump chambers 822, 824, and 826, when pumping a liquid to the body of a patient, preferably are operated utilizing pump stroke cycles including air detection and purging steps, as described previously. FIG. 11a illustrates that pumping cartridge 800 includes several additional design safeguards for preventing air, or other gas, from being pumped to the body of a patient. For example, pump chamber 826, which is configured in this example to pump an anticoagulant to the injection port of a patient for certain embodiments where the pumping cartridge is utilized for blood pumping, has an inlet port 1008 located at the top of the pump chamber and an outlet port 1010 located at the bottom of the pump chamber. This configuration results in any air in the pump chamber rising toward the top of the pump chamber so that it is less likely to be pumped through the outlet port before being detected by the system.

Similarly, all liquid pumped to the patient by pump chambers 822 and 824 are pumped along liquid flow path 959, which is in fluid communication with valving chambers 846 and 854 which, in turn, are in fluid communication with ports 1012 and 1014 located at the bottom of pump chamber 822 and 824, respectively. Thus, as with pump chamber 826, any liquid pumped to the body of a patient using pump chambers 822 or 824 must exit the pump chambers through the bottom port. Similarly, filter element 862 is constructed so that its inlet 904 is located near the top of the filter element, and its outlet 980 is located near the bottom. This arrangement provides an additional layer of protection in that any liquids being pumped to the patient from pump chambers 822 or 824 are first diverted through filter element 862 by bypass valving chamber 860, and any gases contained in such liquids will tend to collect near the top of the filter element and will be inhibited from being pumped to the patient. In contrast, FIG. 11*a* shows that the majority of liquid flow paths in fluid communication with destinations other than the body of a patient, for example plasma return 1002 and centrifuge 1004, are, in turn, in fluid communication with ports 1016 and 1018 located at the top of pump chambers 822 and 824, respectively. When pumping to such destinations, it is typically not critical if air is present in the pumped liquid. During operation, these destinations, for example port 808 and 812, may be used by the system as locations to which to purge any air that is detected in pump chambers 822 and 824 during pump cycles in which a liquid is being pumped to the body of a patient. Any air detected in pump chamber 826 during operation may similarly by purged to port 820 in fluid communication with the anticoagulant supply.

FIG. 11*a* also shows that both pump chambers 822 and 824 contain similar fluidic connections to all of the sources and destinations provided by a pumping cartridge 800 (except ports 818 and 820 utilized solely by pump chamber 826). Accordingly, pump chambers 822 and 824 may be operated individually and independently of each other, in some embodiments, so that liquids pumped with each chamber have a different source and destination or, in other embodiments, pump chambers 822 and 824 may be operated so that their inlet and outlet ports are in fluid communication with common sources and destinations. In the latter embodiments, the pumping system utilizing pumping cartridge 800 can be operated so that the fill and pump strokes of pump chambers 822 and 824 are synchronized so that as one chamber is filling the other chamber is dispensing, and vice versa. Utilizing such an operating protocol, it is possible to operate pump chambers 822 and 824 to achieve a nearly continuous, uninterrupted flow between a desired source and destination.

For embodiments where pump chamber 826 is utilized as an anticoagulant pump, the desired average flow rate to be delivered by the pump chamber may be quite low. In such embodiments, it may be preferable to operate pump chamber 826 utilizing the pulsed delivery protocol described previously. As described previously, in such embodiments, pump chamber 826 is first filled with anticoagulant, inlet valve 832 is closed, a force is applied to flexible membrane 112 adjacent to the pump chamber, and outlet valve 830 is pulsed by selectively opening and closing the outlet valve for predetermined periods of time at predetermined intervals, which intervals and predetermined periods of time are controlled to yield a desired average liquid flow rate. Anticoagulant pump chamber 826 is typically operated to deliver anticoagulant only while either pump chamber 822 or 824 is being filled with blood withdrawn from the body of the patient. Additionally, anticoagulant pump chamber 826 may also be advantageously utilized to dispense anticoagulant when pump chambers 822 and 824 are not pumping liquids to or from the body of the patient but are being utilized for other purposes. In such cases, it may be desirable to continuously, or intermittently dispense a small quantity of anticoagulant with pump chamber 826 in order to assure that syringe/port 950 remains unoccluded. A pulsed delivery, as described above, may be utilized for operating the anticoagulant pump in such applications. For such applications, it is believed that the pulsed delivery of anticoagulant to the injection can have beneficial effects for keeping the site from clotting and dislodging small clots when compared to a continuous delivery of anti coagulant to the site. In addition, preferred embodiments of systems configured to provide pulsed delivery of anticoagulant are configured to continuously monitor the quantity/flow rate of anticoagulant to the patient and can adjust the flow rate by changing and controlling the positive pressure applied to the pump chamber during pulsed delivery as well as by changing the pulse duration and interval between pulses. Such capability allows for improved flow rate delivery volume control for applications where the anticoagulant is being delivered to a site at variable pressure, for example an artery of a patient.

When anticoagulant pump 826 is being utilized to dispense anticoagulant while pump chambers 822 and/or 824 are filling with blood from the patient, the pulse duration and interval between pulses of outlet valve 830 for delivering anticoagulant from pump chamber 826 can be selected, in preferred embodiments, so that the average liquid delivery rate of the anticoagulant is a desired predetermined fraction of the flow rate of blood to pump chambers 822 and/or 824 while they are being filled with blood from the patient. In other embodiments, it may be desirable to operate pump chamber 826 to provide an average liquid flow rate delivered from the pump chamber that is a predetermined fraction of the liquid flow rate of pump chamber 822 and/or 824 during a liquid delivery stroke. In yet other embodiments, pump chamber 826 may be operated so that the average liquid flow rate delivered from the chamber is a predetermined fraction of a liquid flow rate measured for a complete pump stroke (including fill and delivery) of pump chamber 822 and/or 824 or, in yet another embodiment, is a predetermined fraction of an average liquid flow rate (calculated over several pump stroke cycles) of pump chambers 822 and/or 824. It is also to be understood that instead of pump chamber 826 being operated to provide a liquid flow rate that is a predetermined fraction of a liquid flow rate provided by pump chambers 822 and/or 824, alternatively, pump chamber 822 could be operated to provide a liquid flow rate which is a predetermined fraction of a liquid flow rate of pump chamber 824, or vice versa.

Figure 12B:
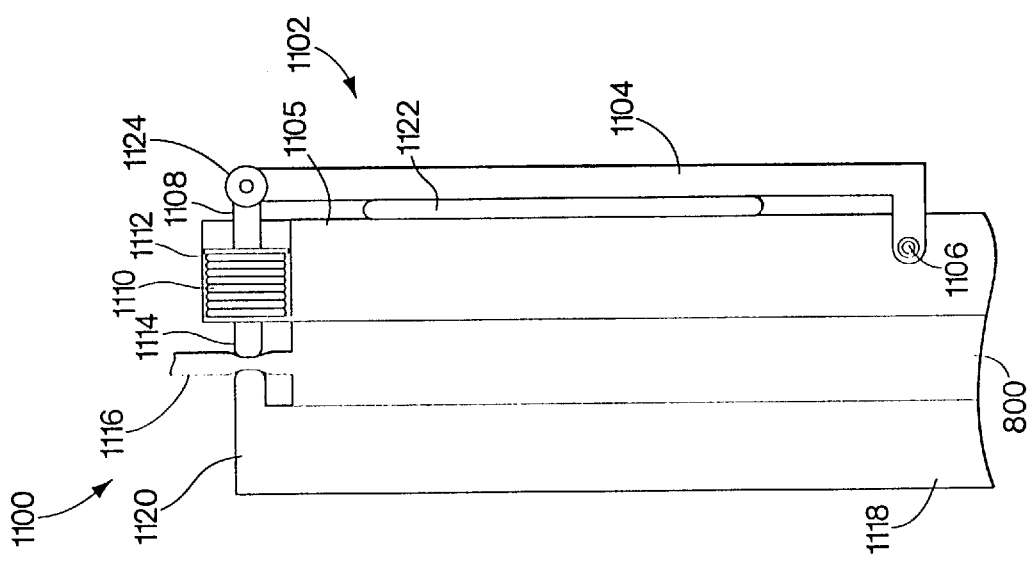
FIG. 12b is a schematic illustration of the occluder mechanism of FIG. 12a in a closed position.
Figure 12A:
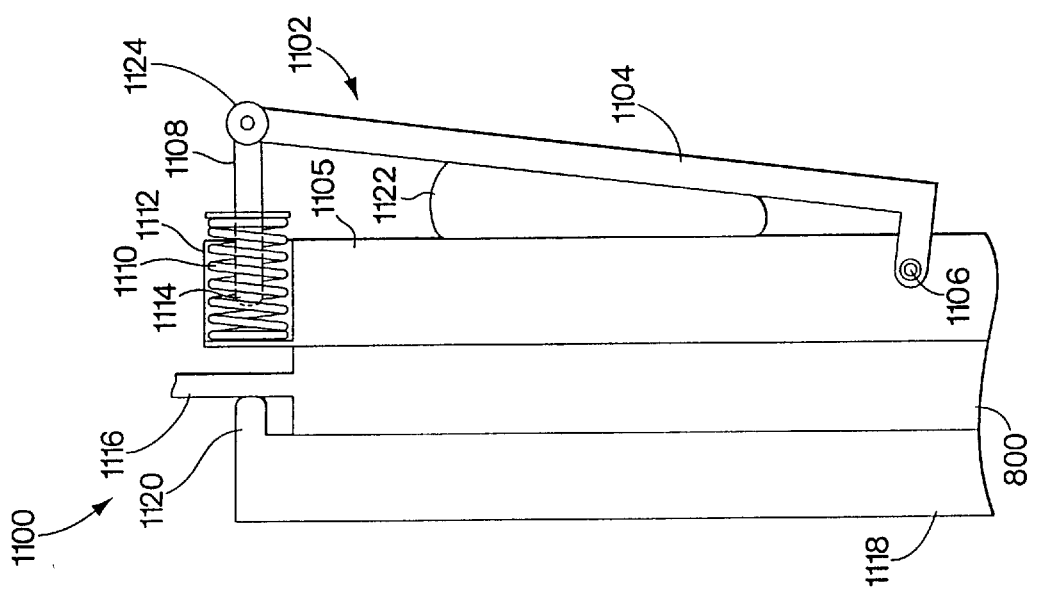
FIG. 12a is a schematic illustration of an occluder mechanism in an open position, according to one embodiment of the invention.

As discussed previously, preferred components of the pump housing component of the reusable system include an occluder bar and mechanism for actuating the bar to selectively occlude the tubing attached in fluid communication with a pumping cartridge. One embodiment of a pump housing component including an occluder bar and actuating mechanism is shown in FIGS. 12*a* and 12*b*. Pump housing component 1100 shown in FIGS. 12*a* and 12*b* includes a spring occluder bar 1102. In the illustrated embodiment, long arm 1104 is pivotally attached to the mating block 1105 of pump housing component 1100 at pivot 1106. As discussed previously in the context of FIG. 10, mating block 1105 will also contain depressions (not shown) forming control and valving chambers, etc. and will be constructed and arranged to mate to the pumping cassette. Occluder bar 1102 has an occluder end that is preferably at about a right angle with respect to the rest of the occluder bar when the occluder is in an occluding configuration as shown in FIG. 12b. The occluder end 1108, in the illustrated embodiment, attached to one end of a spring 1110 that is disposed in a spring housing 1112. The spring housing, in turn, is preferably rigidly attached to mating block 1105. Occluder end 1108 is able to move through the spring housing 1112 by compressing and expanding the spring 1110. The occluder end 1108 terminates at an occluder tip 1114 which is positioned adjacent to, and preferably approximately perpendicular to, fluid lines 1116 attached to the inlet/outlet ports of pump cassette 800.

As discussed previously, cassette 800 is held against the mating block 1105 on pump housing component 1100 cassette door 1118 disposed against the second side of the cassette and opposite the mating block. As shown in FIG. 10 previously, cassette door 1118 preferably includes a piston bladder (not shown) that provides additional mating force to the cassette to create a fluid-tight seal with the mating component. The cassette door 1118 preferably extends beyond cassette 800, thus forming an occluder backstop 1120 disposed adjacent to the fluid lines 1116 and opposite occluder tip 1114. In the illustrated embodiment, an occluder bladder 1122 is disposed between long arm 1104 and mating component 1105. Occluder bladder 1122 can be pressurized to unocclude tubes 1116 with any hydraulic fluid, but in a preferred embodiment the hydraulic fluid comprises air. The occluder bladder 1122 can be supplied with hydraulic fluid via a supply line (not shown), which line in turn can be connected to a pressure reservoir or a pump. The supply line also preferably includes a valve that can be selectively opened to deflate the bladder and occlude tubes 1116. In a preferred embodiment, the valve will fail open, for example if power to the system is interrupted. When occluder bladder 1122 is inflated, the bladder expands against long arm 1104 and displaces occluder tip 1114 away from occluder backstop 1120, thereby opening fluid lines 1116. As the occluder tip 1114 is displaced away from occluder backstop 1120, spring 1110 is compressed to a sufficient degree such that when released, the occluder tip preferably delivers at least a 10 lb closing force on each of the fluid lines 1116. In one preferred embodiment, the maximum displacement of the occluder tip 1114 upon actuation is about 0.25 inch.

Figure 12C:
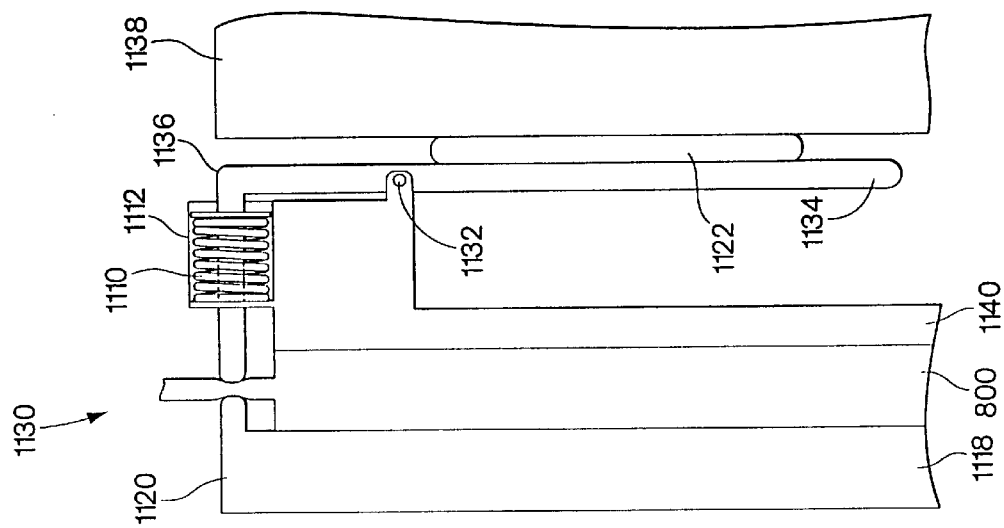
FIG. 12c is a schematic illustration of an occluder mechanism in an open position, according to one embodiment of the invention.
Figure 12D:
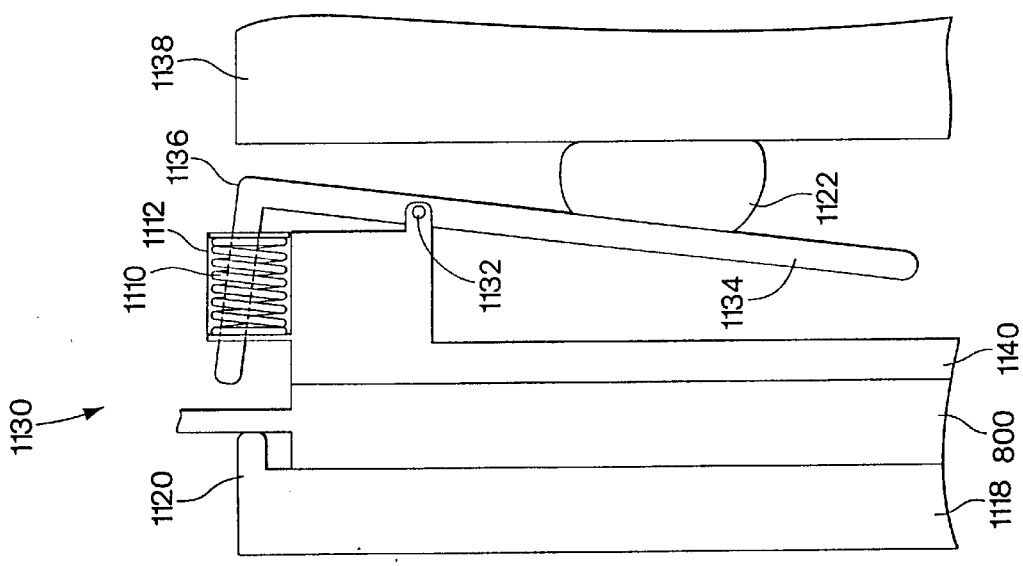
FIG. 12d is a schematic illustration of the occluder mechanism of FIG. 12c in a closed position.

In the embodiment illustrated in FIGS. 12a and 12b, pivot 1106 is located at the end of long arm 1104, opposite occluder end 1108 with occluder bladder 1122 disposed between long arm 1104 and mating block 1105. In an alternative embodiment 1130 shown in FIGS. 12c and 12d, the pivot 1132 can be placed on the long arm 1134 at an intermediate location along its length, preferably close to occluder end 1136, with the occluder bladder 1122 being disposed between long arm 1134 and an occluder frame 1138 that is located opposite and at a spaced distance from mating block 1140.

Referring again to FIGS. 12a and 12b, the illustrated embodiment also includes a hinge 1124 that is incorporated into occluder bar 1102 thereby allowing the occluder end 1108 to rotate about the hinge as the occluder bar is pivotally displaced during opening and occlusion of tubing 1116. Rotation of occluder end 1108 about hinge 1124 allows the occluder end to maintain a more parallel orientation with respect to spring 1110 in spring housing 1112, and thereby reduces the possibility of any spring hold-up during operation.

Figure 12E:
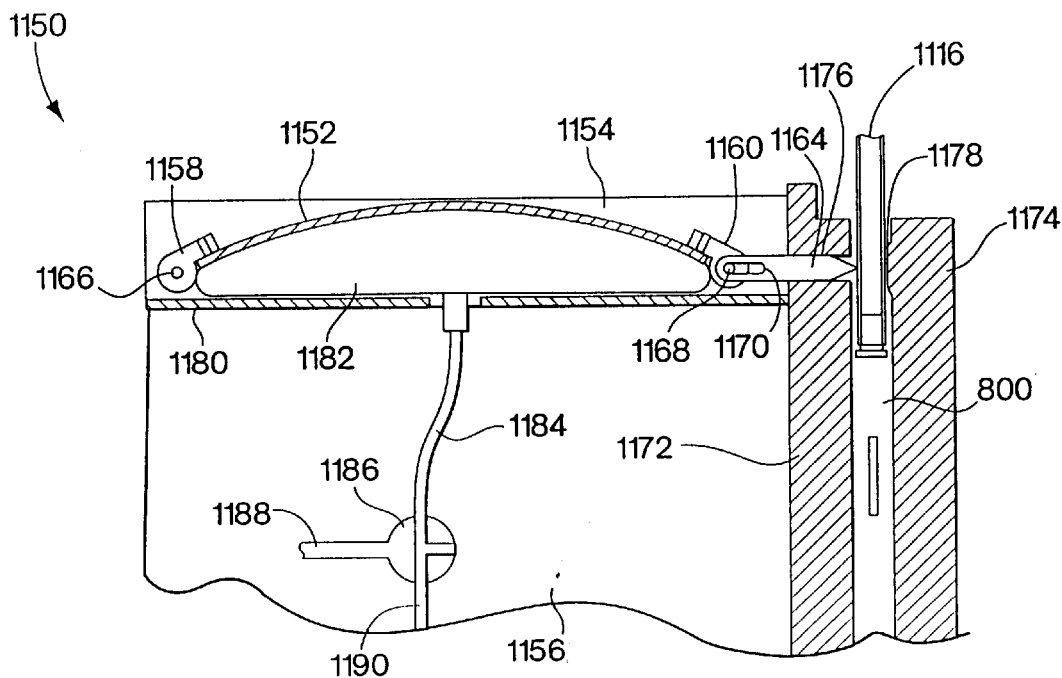
FIG. 12e is a schematic illustration of an occluder mechanism utilizing a spring plate, in an open position, according to one embodiment of the invention.
Figure 12F:
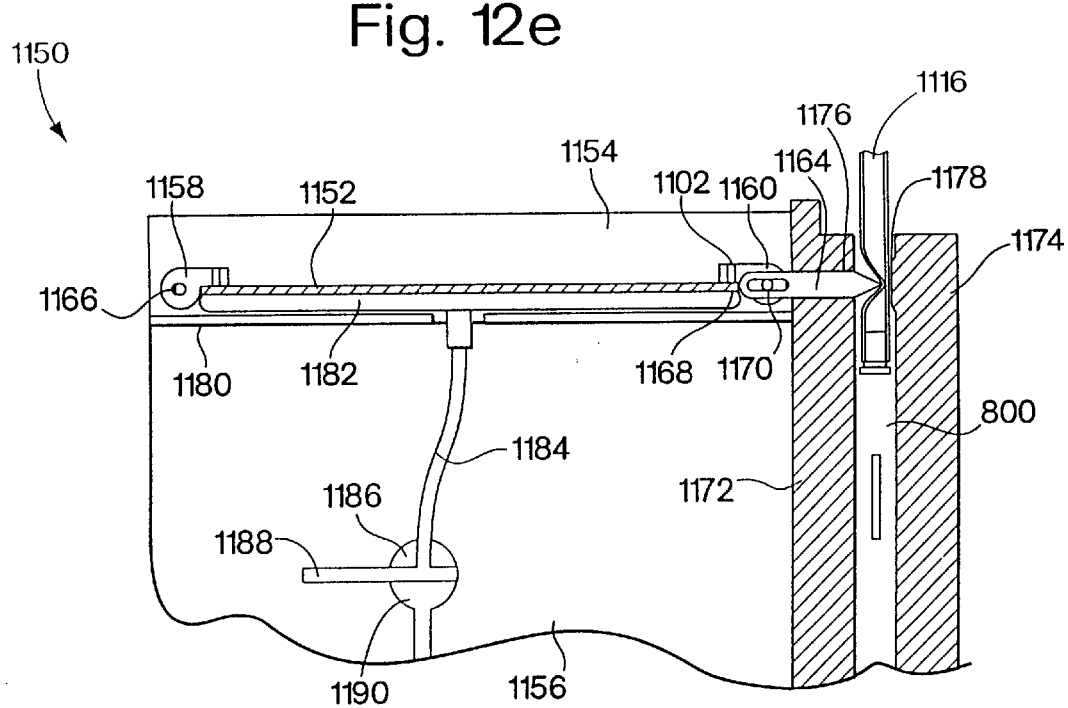
FIG. 12f is a schematic illustration of the occluder mechanism of FIG. 12e in a closed position.

A preferred arrangement of an occluder mechanism is shown in FIGS. 12e and 12f. Occluder mechanism 1150 eliminates the coil spring and spring housing of the previously illustrated embodiments by employing a novel spring plate 1152 mounted to an occluder frame 1154 attached to reusable component 1156. In the embodiment illustrated, the spring plate is connected to occluder frame 1154 by a pair of pivot pins 1166, 1168 which are, in turn, mounted on the occluder frame. Spring mounts 1158, 1160 are preferably firmly attached to spring plate 1152. In alternative embodiments, the spring plate can be attached directly to the occluder frame or attached to the occluder frame be any alternative means apparent to those of ordinary skill in the art.

The spring plate 1152 can be constructed from any material that is elastically resistant to bending forces and which has sufficient longitudinal stiffness (resistance to bending) to provide sufficient restoring force, in response to a bending displacement, to occlude a desired number of collapsible tubes. In the illustrated embodiment, the spring plate is essentially flat and in the shape of a sheet or plate. In alternative embodiments, any occluding member that is elastically resistant to bending forces and which has sufficient longitudinal stiffness (resistance to bending) to provide sufficient restoring force, in response to a bending displacement to occlude a desired number of collapsible tubes may be substituted for the spring plate. Such elongated members can have a wide variety of shapes as apparent to those of ordinary skill in the art, including, but not limited to cylindrical, prism-shaped, trapezoidal, square, or rectangular bars or beams, I-beams, elliptical beams, bowl-shaped surfaces, and others.

In one preferred embodiment, the spring plate 1152 is in the shape of an essentially rectangular sheet and is constructed of spring steel having a thickness that is preferably less than $\frac{1}{10}$ its length (the distance between pivot 1158 and 1160). While the particular dimensions of spring plate 1152 must be determined based on factors which will vary depending on the application, such as the modulus of elasticity of the material from which it is constructed, the shape and thickness of the occluding member the number of tubes to be occluded, the stiffness of the tubes, and other factors as apparent to those of ordinary skill in the art, in a particular preferred embodiment, the spring plate 1152 is constructed from spring steel with a thickness of about 0.035 in. The width (the dimension into the plane of the figures) of the spring plate 1152 is selected enable the plate to occlude all the fluid lines going into or out of cassette 800. The length of the spring plate 1152 can be determined by considering factors such as the required displacement of occluder blade 1164, the mechanical properties of the fluid lines, the yield point and elastic modulus of the spring plate material, and the thickness of the spring plate as mentioned above. Those of ordinary skill in the art can readily select proper materials and dimensions for spring plate 1152 based on the requirements of a particular application. In one exemplary embodiment where the pumping cartridge includes five fluid lines to be occluded, the spring plate is constructed from spring steel and has a thickness of 0.035 inch, a width of 4 inches, and a length of 6.1 inches.

In the illustrated embodiment, rear spring mount 1158 is pivotally attached to the occluder frame 1154 by a rear pivot pin 1166 located at a fixed point on the occluder frame. The spring mount 1158 can, in some embodiments, be a separate piece from the spring plate 1152, which piece is rigidly attached to the spring plate or, in other embodiments, the spring mount 1158 can be integrated into the spring plate, for example, by looping the edge of the spring plate to form a cylinder capable of accepting a pivot pin. The forward spring mount 1160 is attached to the occluder frame 1154 by a forward pivot pin 1168 that can slide in a direction parallel to the length of the spring plate 1152 in a pivot slot 1170 located on the occluder frame 1154. An occluder blade 1164 which moves as the spring plate 1152 is bent, is pivotally attached to the forward pivot pin 1168.

The force required to permit occluder blade 1164 to occlude tubing 1116 is provided by the longitudinal stiffness of spring plate 1152. Upon applying a force to the surface of spring plate 1152 in a direction essentially perpendicular to the surface of the plate (as shown in FIG. 12e), the column stability of the spring plate is disrupted resulting in a buckling of the spring plate causing it to bow and decreasing the longitudinal distance between pivot pins 1166 and 1168. This decrease in distance upon bowing of spring plate 1152 in turn creates a displacement of forward pivot pin 1168 within pivot slot 1170, which displacement causes withdraw of occluder blade 1164 from tubing 1116 thereby opening tubing 1116 to allow fluid in/out of pumping cartridge 800. In alternative embodiments, the force for bending need not be applied directly to a surface of the occluding member with a component of the force in the direction of bending as illustrated. In some alternative embodiments forces utilized for bending the occluding member may be applied to a surface of the member indirectly via components attached to the surface, force creating fields (e.g. electrostatic or magnetic fields), etc., or, alternatively, force may be applied to one or more ends of the occluding member in a direction essentially perpendicular to the bending direction in order to bend the occluding member.

In other alternative embodiments, occluder blade 1164 may not include the pivot pin and pivot slot, but may instead be rigidly attached to the spring plate 1152. In yet other embodiments, the occluder blade may be eliminated altogether with the edge of the spring plate or other occluding member positioned adjacent to the tubing so that the plate/member can open and occlude the tubing as it is during bending and relaxation respectively.

In the illustrated embodiment, occluder frame 1154 is mounted to mating block 1172. The mating block 1172 mates to the first face of a pumping cartridge 800. The pumping cartridge 800 is held in place by a door 1174 (mating block 1172 and door 1174 can include additional components (not shown), such as piston bladders, depressions for forming chambers, etc. as discussed previously). The mating block 1172 and door 1174 can extend beyond the pumping cartridge 800 as shown to allow the tubing 1116 to be occluded by occluder blade 1164. The mating block 1172 incorporates a slot 1176 through which the occluder blade 1164 can be displaced. The slot can be sized and positioned to enable occlusion of all of the fluid lines 1116 entering and exiting the pumping cartridge 800 when the occluder blade 1164 is displaced through the slot 1176 so that it occludes the fluid lines 1116 by pinching them against an extended portion 1178 of the door.

In the illustrated embodiment, a force actuator for applying a bending force to the spring plate comprises an inflatable occluder bladder 1182. The occluder frame 1154 includes a bladder support 1180 housing an inflatable occluder bladder 1182 disposed against the spring plate 1152. The occluder bladder 1182 may be inflated with any hydraulic fluid but in a preferred embodiment air is used as the hydraulic fluid. The inflatable occluder bladder 1182 can be supplied with air via an air line 1184 for either inflating or deflating the bladder. In a preferred embodiment, the air line 1184 can be connected to a three-way valve 1186 controlled by a processor, wherein the occluder bladder 1182 can be placed in fluid communication with either a vent line 1188 for deflating the occluder bladder or a pressure supply line 1190 for inflating the occluder bladder.

Figure 13:
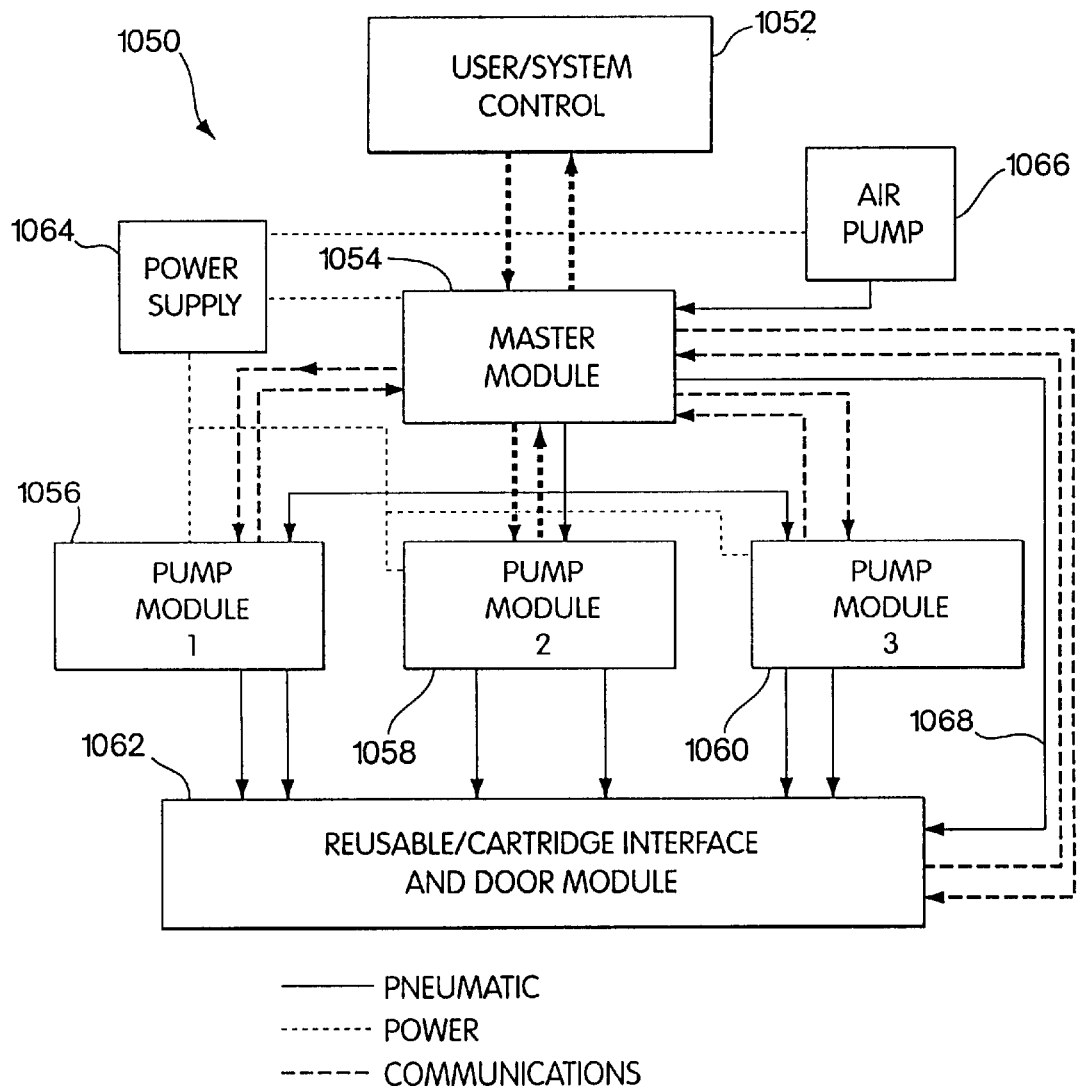
FIG. 13 is a schematic illustration of a flow diagram illustrating the overall system architecture and control configuration for a pumping system, according to one embodiment of the invention.

FIG. 13 illustrates one embodiment for the overall architecture and configuration of a reusable component, including a pumping system, for coupling to and operating a pumping cartridge 800 shown in FIG. 11a. Reusable component 1050 includes three levels of control and includes a variety of individual systems or modules for controlling and operating various components of pumping cartridge 800. Reusable system 1050 includes an overall system controller and user interface 1052 which sends commands to and receives inputs from a master pump system control module 1054. The controller/interface may be implemented using a microprocessor and associated software or using some other mechanism. Master module 1054, in turn, sends commands to and receives input from individual pump drive system modules 1056, 1058, 1060, as well as a door control module 1062. The master module 1054 may also include a microprocessor and appropriate software. Reusable system 1050 also includes a power supply 1064 for providing electrical power to the various modules, and an air pump 1066, which is utilized for providing pressurized measurement gas to the fluid supply tanks of the system. Air pump 1066 is pneumatically connected to master module 1054 which, in turn, is pneumatically connected to the individual pump modules and the door module.

Door module 1062 contains all necessary hardware and pneumatic connections to provide fluid-tight coupling between pumping cartridge 800 and a pump housing component of the reusable system. Door module 1062 also preferably contains a piston bladder and piston, which bladder is in pneumatic communication with master module 1054 via pneumatic line 1068. The configuration of door module 1062 can be similar to that shown previously in FIG. 10, with modifications made to accommodate the size, shape, and fluidic connections of pumping cartridge 800, as would be apparent to one of ordinary skill in the art. In addition, in preferred embodiments, door module 1062 also includes an occluder, which can be similar to occluder 864 shown in FIG. 11a, which is operated by supplying pressurized measurement gas to an occluder bladder (not shown) which forces the occluder against tubing in fluid communication with the various inlet and outlet ports of pumping cartridge 800 to collapse and occlude the tubing, the structure and function of such tubing occluders being known and understood in the art. Pneumatic line 1068 from master module 1054 also, in such embodiments, provides pressurized measurement gas to the occluder bladder.

Each of pump modules 1056, 1058, and 1060 are preferably similar in design, and each is dedicated to the operation of an individual pump chamber, and its associated valves, provided in pumping cartridge 800. For example, pump module 1 (1056) can be configured to operate pump chamber 822, and its associated valves, pump module 2 (1058) can be configured to operate pump chamber 824, and its associated valves, and pump module 3 (1060) can be configured to operate pump chamber 826, and its associated valves. Each pump module is in pneumatic communication with door module 1062, in order to supply measurement gas to the various control and valve actuating chambers in the pump housing component, which are disposed adjacent to the pump chambers and valving chambers of pumping cartridge 800, when the system is in operation.

In a preferred embodiment, each of the pump modules is configured in a similar fashion as pump drive system 502 shown previously in FIG. 8, except that pump 516, positive pressure tank 508, and negative pressure tank 512 are not contained in the pump module as suggested in FIG. 8 but, instead, in reusable system 1050, pump 516 is replaced by air pump 1066, and the pressure tanks are resident in master module 1054 and are shared by the individual pump modules. Each pump module preferably includes valves, pressure transducers, and a reference chamber dedicated to its respective pump chamber. Each pump module also preferably contains additional pneumatic valves to selectively provide pressurized measurement gas to actuate the various valving chambers associated with its respective pump chamber. In addition, each pump module preferably contains a dedicated microprocessor for controlling the operation of the individual pump chamber and performing the various calculations associated with the operation of the pump chamber, as discussed previously.

Each of the microprocessors included in the various pump modules is preferably configured to communicate with a microprocessor in master module 1054. Master module 1054 is preferably configured to control the pressure within the positive and negative pressure fluid supply tanks preferably included therein, as well as within the piston bladder and occluder bladder in door module 1062. The microprocessor included in master module 1054 preferably acts as the primary communications interface between the user interface and system control module 1052 and the individual pump control modules 1056, 1058, and 1060.

Master module 1054 is preferably configured to handle all of the input/output communications with the user interface/system control module 1052. The commands input to master module 1054 from module 1052 can be processed by the microprocessor of master module 1054 and in turn can be translated by the microprocessor into appropriate commands for input to the microprocessors that are resident in individual pump modules 1056, 1058, and 1060. In preferred embodiments, overall system control module 1052 includes the majority of application-specific programming and provides for communication between the reusable system and a user of the system. Upon receipt of a command from system control module 1052 by master module 1054, the master module is preferably configured to: (1) determine which valves of the system are to be opened or closed; (2) determine which pump module/door module/master module contains the valves; and (3) issue an appropriate command to open or close such valves. All valve mapping (i.e., physical location of the various valves in the system) that is unique to the operation of the particular pumping cartridge being utilized, is preferably resident in the microprocessor of master module 1054.

Also, in preferred embodiments, embedded application programming for each of the microprocessors in the various pump modules may be similar. In some preferred embodiments, there is no application-specific programming resident in pump modules 1056, 1058, and 1060. In preferred embodiments, pump modules receive commands from master module 1054 and are configured to determine which commands from master module 1054 to act on and which to ignore based upon whether the specific valves or components which are the subject of the command are resident in the particular pump module.

It should be appreciated that the overall system architecture described in FIG. 13 for reusable system 1050 is purely exemplary, and that those of ordinary skill in the art will readily envision a wide variety of other ways to select components and configure and control the system and various components thereof, each of which configurations is considered within the scope of the present invention.

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, or method described herein. In addition, any combination of two or more such features, systems, or methods, provided that such features, systems, or methods are not mutually inconsistent, is included within the scope of the present invention.

What is claimed is:

1. A pumping cartridge comprising:
   a first liquid flow path;
   a second liquid flow path; and
   a bypass valve in fluid communication with the first liquid flow path and the second fluid flow path, said bypass valve constructed and arranged to selectively permit liquid flow through
   said first liquid flow path while restricting liquid flow through said second liquid flow path,
   said second liquid flow path while restricting liquid flow through said first liquid flow path, and
   to prevent liquid flow through both said first liquid flow path and said second liquid flow path.

2. The pumping cartridge of claim 1, wherein the pumping cartridge is disposable and is constructed and arranged to be coupled to a reusable component.

3. The pumping cartridge of claim 1, wherein the pumping cartridge comprises a first substantially rigid component and at least one flexible membrane disposed on the first component, the first component and the flexible membrane defining a bypass valving chamber forming the bypass valve.

4. The pumping cartridge of claim 3, wherein the bypass valving chamber includes three ports, two of which ports are occludable by the flexible membrane.

5. The pumping cartridge of claim 4, wherein the first liquid flow path enters the bypass valving chamber through a first port and exits the bypass valving chamber through a third occludable port, and wherein the second liquid flow path enters the bypass valving chamber through a second occludable port and exits the bypass valving chamber through the first port.

6. A pumping cartridge comprising:
   a first component;
   at least one membrane disposed on the first component, the first component and the membrane defining a bypass valving chamber, said bypass valving chamber including three ports, two of which ports are occludable by said flexible membrane;
   a first fluid flow path entering the bypass valving chamber through a first port and exiting the bypass valving chamber through a third occludable port; and
   a second fluid flow path entering the bypass valving chamber through a second occludable port and exiting the bypass valving chamber through said first port.

7. The pumping cartridge of claim 6, wherein the membrane is flexible.

8. The pumping cartridge of claim 6, wherein the membrane is elastic.

9. The pumping cartridge of claim 6, wherein the pumping cartridge is disposable and is constructed and arranged to be coupled to a reusable component.

10. The pumping cartridge of claim 9, wherein the first component is formed of a substantially rigid material.

11. The pumping cartridge of claim 10, wherein said first component has a depression therein, which depression in combination with the membrane forms the bypass valving chamber.

12. The pumping cartridge of claim 11, wherein the first component has a first side and a second side, the first side including the depression which in combination with the membrane forms the bypass valving chamber, and said second side including at least one groove or channel therein providing a liquid flow path.

13. The pumping cartridge of claim 12, wherein the first side of the first component includes at least one groove or channel providing a liquid flow path.

14. The pumping cartridge of claim 13, wherein the second side of the first component includes a membrane disposed thereon, which in combination with the first component provides at least one liquid flow path.

15. The pumping cartridge of claim 12, wherein the second occludable port and the third occludable port comprise holes within the first component, which holes are each located on a member that protrudes from a base of said depression.

16. The pumping cartridge of claim 15, wherein the first port is non-occludable and comprises a hole within the first component formed within the base of said depression.

17. The pumping cartridge of claim 6, wherein the bypass valving chamber includes two adjacent subchambers, the subchambers including a partition therebetween that forms a fluid-tight seal with the membrane when the pump chamber is coupled to the reusable component, which partition includes an opening therein allowing unrestricted fluid communication between the adjacent subchambers.

18. The pumping cartridge of claim 6, wherein the first port is in fluid communication with a line connecting the pumping cartridge to a body of a patient, the second occludable port is in fluid communication with a filter element included within the pumping cartridge, and the third occludable port is in fluid communication with an inlet valve or an outlet valve of at least one pump chamber included within the pumping cartridge, when the pumping cartridge is in operation.

19. A reusable system constructed and arranged for operative association with a removable pumping cartridge, which pumping cartridge providing at least two fluid flow paths therein and including a bypass valving chamber in fluid communication with a first fluid flow path and a second fluid flow path, the system including:
   a pump housing component constructed and arranged to couple to said pumping cartridge; and
   a valve actuator adapted to actuate said bypass valving chamber to selectively permit fluid flow through
      said first fluid flow path while restricting fluid flow through said second fluid flow path,
      said second fluid flow path while restricting fluid flow through said first fluid flow path, and
      to prevent fluid flow through both said first fluid flow path and said second fluid flow paths, wherein
      said actuator is disposed within said pump housing adjacent to and in operative association with said bypass valving chamber when said pumping cartridge is coupled to said pump housing.

20. The reusable system of claim 19, wherein the pump chamber includes a first component, and at least one flexible membrane disposed on the first component, the first component and the flexible membrane defining the bypass valving chamber, and wherein the valve actuator includes a force applicator, said force applicator constructed and arranged to alternatively (i) apply a force to at least a portion of said flexible membrane to restrict liquid flow through said first liquid flow path in said pump cartridge, (ii) apply a force to at least a portion of said flexible membrane to restrict liquid flow through said second liquid flow path in said pump cartridge, and (iii) apply a force to at least a portion of said flexible membrane to restrict liquid flow through both said first and said second liquid flow paths.

21. A reusable system constructed and arranged for operative association with a removable pumping cartridge, which pumping cartridge providing at least two liquid flow paths therein and including a first component, and at least one membrane disposed on the first component, where the first component and the membrane define a bypass valving chamber, said reusable system comprising:
   a pump housing component constructed and arranged for operative association with said pumping cartridge by coupling to the pumping cartridge;
   a valve actuator to actuate said bypass valving chamber, said actuator disposed adjacent to and in operative association with said bypass valving chamber when said pumping cartridge is coupled to said pump housing; and
   a force applicator forming at least a part of said valve actuator, said force applicator constructed and arranged to alternatively (i) apply a force to at least a portion of said membrane to restrict liquid flow through a first liquid flow path through said bypass valving chamber while permitting liquid flow through a second liquid flow path through said bypass valving chamber, (ii) apply a force to at least a portion of said membrane to restrict liquid flow through said second liquid flow path through said bypass valving chamber while permitting liquid flow through said first liquid flow path through said bypass valving chamber, and (iii) apply a force to at least a portion of said membrane to restrict liquid flow through both said first and said second liquid flow paths.

22. The reusable system of claim 21, wherein the pump housing component includes an interface constructed and arranged for creating a fluid-tight seal with the pumping cartridge upon coupling.

23. The reusable system of claim 22, wherein the interface includes at least one depression in contact with and adjacent to the bypass valving chamber upon coupling of the pumping cartridge and the reusable component, said at least one depression forming a valve actuating chamber in contact with and adjacent to the bypass valving chamber.

24. The reusable system of claim 23, wherein the force applicator comprises a fluid supply system in fluid communication with the valve actuating chamber, the fluid supply system being constructed and arranged to pressurize the valve actuating chamber thereby applying a force to the membrane.

25. The reusable system of claim 21, further comprising a processor configured to control the operation of the valve actuator.

26. A method for directing flow in a pumping cartridge, said pumping cartridge including a bypass valving chamber, having three ports therein and two liquid flow paths therethrough, where at least a portion of which bypass valving chamber is formed from a membrane, the method comprising:

occluding a first port disposed in said bypass valving chamber with said membrane to restrict a flow of liquid through said bypass valving chamber along a first flow path while permitting liquid flow through said bypass valving chamber along a second liquid flow path;

occluding a second port disposed in said bypass valving chamber with said membrane to restrict a flow of liquid through said bypass valving chamber along said second flow path while permitting liquid flow through said bypass valving chamber along said first liquid flow path; and occluding both said first and said second ports disposed in said bypass valving chamber with said membrane to restrict a flow of liquid along both said first and said second flow paths.

27. The method of claim 26, wherein said membrane is flexible.

28. The method of claim 26, where the occluding steps comprise applying a force to the membrane causing the membrane to make a sealing contact with a port.

29. The method of claim 28, wherein the force is applied to the membrane by bringing a fluid having a pressure greater than a pressure within the bypass valving chamber into contact with the membrane.

30. The method of claim 26, further comprising the step of coupling the pumping cartridge in operative association with a reusable component.

31. The method of claim 26, wherein during the occluding steps, the ports are occluded so as to essentially prevent a flow of liquid through the ports.

32. The method of claim 26, wherein occluding the first port prevents a flow of liquid from a pump chamber, included within the pumping cartridge, through a filter element, included within the pumping cartridge, and to a body of a patient.

33. The method of claim 32, wherein occluding the second port prevents a flow of liquid from a body of a patient and to a pump chamber included within the pumping cartridge.

* * * * *

UNITED STATES PATENT AND TRADEMARK OFFICE
CERTIFICATE OF CORRECTION

PATENT NO. : 6,416,293 B1
DATED : July 9, 2002
INVENTOR(S) : Clement D. Bouchard et al.

It is certified that error appears in the above-identified patent and that said Letters Patent is hereby corrected as shown below:

Title page,
Item [75], Inventors: "Lawrence B. Gray" should be "Larry B. Gray"
Item [73], Assignee: "Deka" should be "DEKA"

Column 51,
Line 63, please change "paths" to -- path --

Signed and Sealed this

Twenty-fifth Day of February, 2003

JAMES E. ROGAN
*Director of the United States Patent and Trademark Office*